(12) United States Patent
Mantovani et al.

(10) Patent No.: US 11,254,739 B2
(45) Date of Patent: Feb. 22, 2022

(54) ANTI-HUMAN MIGRATION STIMULATING FACTOR (MSF) AND USES THEREOF

(71) Applicant: HUMANITAS MIRASOLE S.P.A., Rozzano (IT)

(72) Inventors: Alberto Mantovani, Rozzano (IT); Barbara Bottazzi, Rozzano (IT); Ilaria Laface, Rozzano (IT); Antonio Inforzato, Rozzano (IT); Tamara Gulic, Rozzano (IT)

(73) Assignee: HUMANITAS MIRASOLE S.P.A., Rozzano (IT)

( * ) Notice: Subject to any disclaimer, the term of this patent is extended or adjusted under 35 U.S.C. 154(b) by 0 days.

(21) Appl. No.: 16/648,333

(22) PCT Filed: Sep. 19, 2018

(86) PCT No.: PCT/EP2018/075363
§ 371 (c)(1),
(2) Date: Mar. 18, 2020

(87) PCT Pub. No.: WO2019/057780
PCT Pub. Date: Mar. 28, 2019

(65) Prior Publication Data
US 2020/0283515 A1    Sep. 10, 2020

(30) Foreign Application Priority Data
Sep. 19, 2017  (IT) .................. 102017000104736

(51) Int. Cl.
C07K 16/24       (2006.01)
G01N 33/68       (2006.01)

(52) U.S. Cl.
CPC ......... C07K 16/24 (2013.01); G01N 33/6878 (2013.01); C07K 2317/34 (2013.01); C07K 2317/55 (2013.01); G01N 2800/122 (2013.01); G01N 2800/24 (2013.01); G01N 2800/50 (2013.01); G01N 2800/52 (2013.01)

(58) Field of Classification Search
None
See application file for complete search history.

(56) References Cited

FOREIGN PATENT DOCUMENTS

| WO | 9000567 A1 | 1/1990 |
|----|-----------|--------|
| WO | 9931233 A1 | 6/1999 |

OTHER PUBLICATIONS

Schor et al. Migration-stimulating factor: a genetically truncated onco-fetal fibronectin isoform expressed by carcinoma and tumor-associated stromal cells, Cancer Research, 63, 8827-8836, 2003. (Year: 2003).*
Lloyd et al., Protein Engineering, Design & Selection, 22:159-168, 2009. (Year: 2009).*
Schor et al., "Migration-Stimulating Factor: A Genetically Truncated Onco-Fetal Fibronectin Isoform Expressed by Carcinoma and Tumor-Associated Stromal Cells", Cancer Research, 2003, pp. 8827-8836.
Perrier et al., "Migration Stimulating Factor (MSF): A Novel Biomarker of Breast Cancer Progression", Translational Medicine, 2012, vol. 1, No. S1, pp. 1-7.
Solinas et al., "Tumor-Conditioned Macrophages Secrete Migration-Stimulating Factor: A New Marker for M2-Polarization, Influencing Tumor Cell Motility", The Journal of Immunology, 2010, vol. 185, No. 1, pp. 642-652.
International Search Report and Written Opinion for Corresponding International Application No. PCT/EP2018/075363 (10 Pages) (dated Dec. 17, 2018).

* cited by examiner

*Primary Examiner* — Elly-Gerald Stoica
(74) *Attorney, Agent, or Firm* — Lucas & Mercanti, LLP

(57) ABSTRACT

The present invention refers to an antibody able to recognize and bind to an epitope comprised in a sequence of human Migration Stimulating Factor (MSF), and that doesn't recognize and bind human Fibronectin 1 (hFn1) and to uses in diagnostic methods and therapy.

Figure 1:
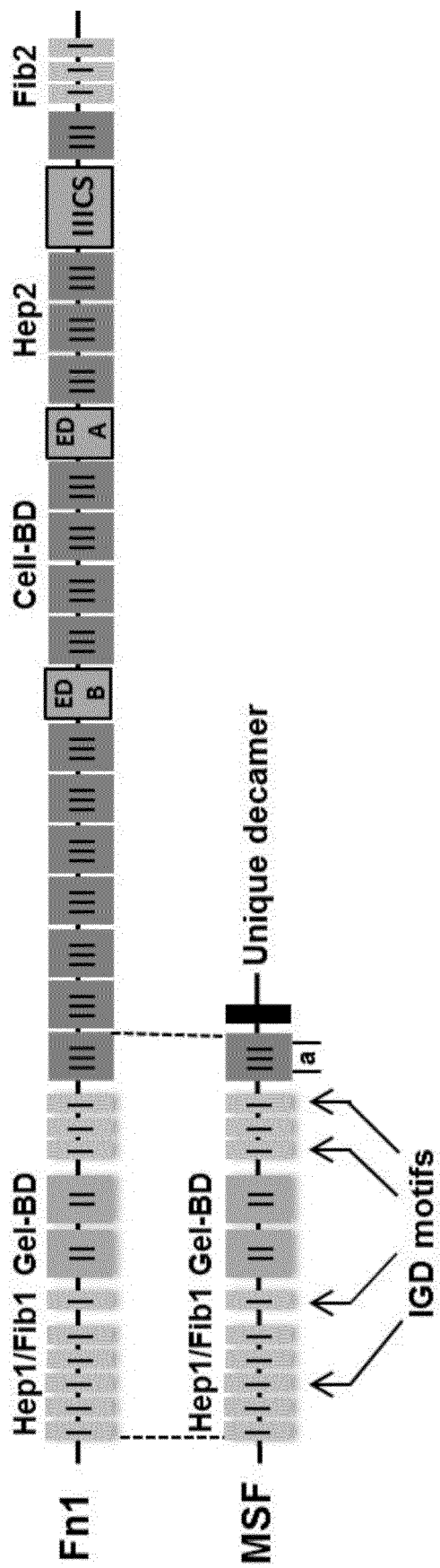

16 Claims, 13 Drawing Sheets
Specification includes a Sequence Listing.

| coating with peptide | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 0,252 | 0,234 | 0,203 | 0,221 | 0,178 | 0,172 | 0,185 | 0,244 | 0,262 | 0,281 | 0,174 | 0,185 |
| B | 0,2 | 0,206 | 0,224 | 0,186 | 0,168 | 0,184 | 0,186 | 0,244 | 0,171 | 0,202 | 0,142 | 0,173 |
| C | 0,343 | 0,222 | 0,198 | 0,204 | 0,194 | 0,174 | 0,184 | 0,189 | 0,189 | 0,196 | 0,158 | 0,18 |
| D | 0,307 | 0,201 | 0,178 | 0,217 | 0,167 | 0,148 | 0,161 | 0,166 | 0,184 | 0,256 | 0,151 | 0,185 |
| E | 0,191 | 0,208 | 0,215 | 0,253 | 0,166 | 0,143 | 0,179 | 0,176 | 0,177 | 0,209 | 0,156 | 0,158 |
| F | 0,176 | 0,223 | 0,178 | 0,22 | 0,183 | 0,16 | 0,163 | 0,183 | 0,18 | 0,2 | 0,148 | 0,174 |
| G | 0,181 | 0,205 | 0,189 | 0,215 | 0,503 | 0,178 | 0,174 | 0,206 | 0,187 | 0,209 | 0,139 | 0,19 |
| H | 0,271 | 0,255 | 0,233 | 0,201 | 0,181 | 0,228 | 0,199 | 0,209 | 0,248 | 0,251 | 0,169 | 0,212 |

| coating with supernatant from CHO-3E6 | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 0,186 | 0,242 | 0,164 | 0,197 | 0,194 | 0,203 | 0,191 | 0,176 | 0,188 | 0,186 | 0,18 | 0,216 |
| B | 0,183 | 0,203 | 0,18 | 0,168 | 0,184 | 0,198 | 0,167 | 1,208 | 0,167 | 0,173 | 0,179 | 0,23 |
| C | 0,187 | 0,215 | 0,19 | 0,215 | 0,197 | 0,184 | 0,195 | 0,169 | 0,164 | 0,181 | 0,188 | 0,194 |
| D | 0,204 | 0,204 | 0,189 | 0,163 | 0,187 | 0,191 | 0,204 | 0,22 | 0,182 | 0,189 | 0,193 | 0,236 |
| E | 0,168 | 0,225 | 0,203 | 0,183 | 0,19 | 0,242 | 0,175 | 0,186 | 0,193 | 0,159 | 0,183 | 0,236 |
| F | 0,223 | 0,205 | 0,187 | 0,188 | 0,223 | 0,187 | 0,216 | 0,188 | 0,171 | 0,16 | 0,174 | 0,237 |
| G | 0,243 | 0,217 | 0,183 | 0,193 | 1,759 | 0,222 | 0,21 | 0,197 | 0,168 | 0,179 | 0,157 | 0,233 |
| H | 0,218 | 0,215 | 0,197 | 0,185 | 0,214 | 0,211 | 0,21 | 0,214 | 0,205 | 0,213 | 0,223 | 0,253 |

Fig. 5

Plate 1: coating with supernatant from CHO-3E6

|   | 1 | 2 | 3 | 4 | 5 | 6 | 7 | 8 | 9 | 10 | 11 | 12 |
|---|---|---|---|---|---|---|---|---|---|----|----|----|
| A | 0,042 | 0,055 | 0,942 | 0,056 | 0,059 | 0,082 | 0,058 | 0,06 | 0,107 | 0,059 | 0,069 | 0,058 |
| B | 0,042 | 0,052 | 0,05 | 0,052 | 0,349 | 1,177 | 0,574 | 0,185 | 0,05 | 0,049 | 0,886 | 0,827 |
| C | 0,643 | 0,049 | 0,049 | 0,051 | 1,036 | 0,051 | 0,053 | 0,053 | 0,053 | 0,101 | 0,053 | 0,052 |
| D | 0,854 | 1,553 | 0,051 | 0,318 | 0,051 | 0,052 | 1,151 | 0,195 | 0,058 | 1,005 | 0,95 | 0,056 |
| E | 0,143 | 0,051 | 0,11 | 0,068 | 0,06 | 0,063 | 0,082 | 1,46 | 0,055 | 1,175 | 0,052 | 0,057 |
| F | 0,122 | 0,05 | 0,051 | 0,059 | 0,051 | 0,059 | 1,444 | 0,053 | 0,052 | 0,049 | 0,051 | 0,067 |
| G | 0,048 | 0,049 | 0,05 | 0,053 | 1,235 | 0,826 | 0,049 | 0,051 | 0,836 | 0,05 | 0,052 | 0,115 |
| H | 0,042 | 0,071 | 0,066 | 0,467 | 0,061 | 0,063 | 0,059 | 1,133 | 0,057 | 0,068 | 1,351 | 0,144 |

Plate 2: coating with supernatant from CHO-3E6

|   | 1 | 2 | 3 | 4 | 5 | 6 | 7 | 8 | 9 | 10 | 11 | 12 |
|---|---|---|---|---|---|---|---|---|---|----|----|----|
| A | 0,043 | 0,076 | 0,058 | 0,796 | 0,059 | 0,06 | 0,056 | 0,336 | 0,052 | 0,05 | 0,052 | 0,093 |
| B | 0,043 | 0,054 | 0,077 | 0,092 | 0,14 | 0,048 | 0,048 | 1,171 | 1,012 | 1,169 | 0,078 | 0,06 |
| C | 0,814 | 0,659 | 0,162 | 0,056 | 1,093 | 0,051 | 0,05 | 0,052 | 0,05 | 0,054 | 0,048 | 0,058 |
| D | 0,626 | 0,049 | 0,049 | 0,05 | 0,335 | 0,051 | 0,077 | 0,05 | 0,051 | 0,049 | 0,048 | 0,058 |
| E | 0,107 | 0,05 | 0,06 | 0,052 | 1,322 | 0,052 | 1,083 | 0,049 | 0,048 | 1,252 | 0,049 | 0,056 |
| F | 0,103 | 0,05 | 0,049 | 0,05 | 0,05 | 0,053 | 0,051 | 0,049 | 0,05 | 0,049 | 0,049 | 0,058 |
| G | 0,042 | 0,048 | 0,05 | 1,157 | 0,053 | 1,022 | 0,056 | 0,054 | 0,051 | 0,049 | 0,05 | 0,07 |
| H | 0,042 | 0,75 | 0,979 | 0,055 | 0,873 | 0,056 | 0,846 | 0,053 | 0,056 | 0,062 | 0,081 | 0,629 |

Plate 1: coating with peptide

|   | 1 | 2 | 3 | 4 | 5 | 6 | 7 | 8 | 9 | 10 | 11 | 12 |
|---|---|---|---|---|---|---|---|---|---|----|----|----|
| A | 0,044 | 0,269 | 0,306 | 0,194 | 0,212 | 0,224 | 0,194 | 0,245 | 0,272 | 0,215 | 0,253 | 0,243 |
| B | 0,048 | 0,252 | 0,212 | 0,198 | 0,28 | 0,321 | 0,208 | 0,194 | 0,2 | 0,204 | 0,322 | 0,292 |
| C | 1,794 | 0,177 | 0,265 | 0,205 | 0,357 | 0,167 | 0,248 | 0,248 | 0,194 | 0,199 | 0,25 | 0,182 |
| D | 1,49 | 0,458 | 0,252 | 0,295 | 0,271 | 0,199 | 0,336 | 0,197 | 0,205 | 0,339 | 0,347 | 0,214 |
| E | 0,298 | 0,216 | 0,215 | 0,197 | 0,282 | 0,191 | 0,15 | 0,447 | 0,241 | 0,377 | 0,305 | 0,153 |
| F | 0,241 | 0,222 | 0,199 | 0,246 | 0,256 | 0,203 | 0,536 | 0,191 | 0,244 | 0,265 | 0,256 | 0,192 |
| G | 0,042 | 0,219 | 0,246 | 0,182 | 0,405 | 0,241 | 0,194 | 0,241 | 0,249 | 0,239 | 0,273 | 0,196 |
| H | 0,042 | 0,203 | 0,216 | 0,209 | 0,259 | 0,219 | 0,237 | 0,338 | 0,244 | 0,245 | 0,423 | 0,197 |

Plate 2: coating with peptide

|   | 1 | 2 | 3 | 4 | 5 | 6 | 7 | 8 | 9 | 10 | 11 | 12 |
|---|---|---|---|---|---|---|---|---|---|----|----|----|
| A | 0,044 | 0,36 | 0,336 | 0,361 | 0,24 | 0,277 | 0,274 | 0,294 | 0,231 | 0,34 | 0,32 | 0,388 |
| B | 0,049 | 0,274 | 0,269 | 0,257 | 0,268 | 0,282 | 0,268 | 0,494 | 0,372 | 0,46 | 0,249 | 0,294 |
| C | 1,999 | 0,31 | 0,232 | 0,202 | 0,61 | 0,235 | 0,259 | 0,243 | 0,235 | 0,271 | 0,218 | 0,302 |
| D | 1,992 | 0,261 | 0,285 | 0,268 | 0,295 | 0,207 | 0,248 | 0,291 | 0,256 | 0,274 | 0,254 | 0,323 |
| E | 0,307 | 0,253 | 0,229 | 0,227 | 0,49 | 0,227 | 0,375 | 0,299 | 0,23 | 0,579 | 0,259 | 0,273 |
| F | 0,288 | 0,249 | 0,253 | 0,243 | 0,284 | 0,253 | 0,254 | 0,262 | 0,231 | 0,232 | 0,262 | 0,259 |
| G | 0,044 | 0,316 | 0,243 | 0,638 | 0,361 | 0,526 | 0,289 | 0,238 | 0,304 | 0,243 | 0,34 | 0,327 |
| H | 0,043 | 0,329 | 0,445 | 0,198 | 0,316 | 0,269 | 0,291 | 0,207 | 0,26 | 0,235 | 0,193 | 0,344 |

Fig. 6

ANTI-HUMAN MIGRATION STIMULATING FACTOR (MSF) AND USES THEREOF

CROSS-REFERENCE TO RELATED APPLICATIONS

This application is a 371 of PCT/EP2018/075363, filed Sep. 19, 2018, which claims the benefit of Italian Patent Application No. 102017000104736, filed Sep. 19, 2017.

TECHNICAL FIELD OF THE INVENTION

The present invention relates to anti-MSF (Migration Stimulating Factor) antibodies, to their medical use and to their use in diagnostic or prognostic methods of inflammatory disorders, particularly of tumours.

PRIOR ART

Plasticity is a hallmark of macrophages: exposed to cytokines or microbial products they acquire specific and distinct phenotypes. M1 and M2 polarized macrophages are the extremes of a continuum of functional states [1]. While M1 macrophages mediate resistance to intracellular pathogens and tumors, M2 polarized macrophages exert immunoregulatory properties and orchestrate tissue repair and remodeling. In addition, M2 macrophages play a role in several inflammatory disorders, such as asthma and allergic diseases, and in resistance to parasites [2]. In cancer, tumor associated macrophages (TAMs) are the most abundant host inflammatory cells and are essential constituents of the tumor microenvironment [3-5]. TAMs exert dual roles: on one side, as expected, they can elicit antitumor responses, but in most cases, they orchestrate key steps required for cancer occurrence and progression [6-8]. Exposed to tumor-derived products, TAMs acquire an M2-like phenotype and promote tumor proliferation and progression, angiogenesis and lymphangiogenesis, inhibiting adaptive immunity. The role of macrophages in tumor growth has been demonstrated in experimental models. In humans, CD68+ or CD163+ TAMs infiltrating solid tumors, such as breast and pancreatic cancer, correlate with poor outcome [9-11]. Similarly, increased number of TAMs is strongly associated with shortened progression-free survival in patients with Classic Hodgkin's Lymphoma [12]. Targeting of TAMs is a key property of selected anticancer compounds, such as Trabectedin, an EMA and FDA approved antitumor agent [13]. Antibodies or single molecules targeting the macrophage colony stimulating factor (M-CSF or CSF-1) pathway, a major regulator of migration, differentiation, and survival of macrophages and their precursors, are undergoing clinical assessment per se or in concert with checkpoint blockade inhibitors [14]. Thus, preclinical and clinical data indicate that TAMs are a potential biomarker for risk stratification of cancer patients and provide a proof of principle for TAM directed therapies [7,15-17]. From what outlined above, it is apparent that suitable biomarkers are needed to identify TAMs within the tumor mass and to characterize M2 polarized macrophages as a therapeutic target. Gene profiling of M1 and M2 polarized macrophages as well as M2-like TAMs revealed a series of genes selectively expressed by M2 polarized cells [18]. One of these molecules is a truncated form of human Fibronectin 1 (hFn1) called Migration Stimulating Factor (MSF), [18,19] (FIG. 1). DNA and protein sequences for human Fn1 (SEQ ID No: 1, NCBI accession number AB191261.1 for DNA; SEQ ID No: 2, NCBI accession number BAD52437.1 for protein) and MSF (SEQ ID No: 3, NCBI accession number AJ535086.1 for DNA; SEQ ID No: 4, NCBI accession number CAH60958.1 for protein) are reported below. The cDNA of human MSF is identical to the 5' end of human fibronectin cDNA, up to and including exon III-1a, and terminates with a unique 195-nucleotide sequence at the 3' end. The expression of MSF is controlled at both transcriptional and posttranscriptional levels by a two-step mechanism. The primary MSF transcript is initially generated from the fibronectin gene by read through of the intron that separates exons III-1a and III-1b, followed by intra-intronic cleavage to produce a 5.9-kb MSF pre-mRNA (transcriptional level). This precursor is further cleaved to make a 2.1-kb mature MSF mRNA, which contains a 30-bp in-frame coding sequence, contiguous to exon III-1a (post-transcriptional level). The mature mRNA is rapidly exported to the cytoplasm, where it is translated into a 70-kDa protein identical to the N terminus of full-length fibronectin (up to and including the amino-acid sequence coded by exon III-1a), with the addition of an MSF-unique (intron-coded) 10 amino-acid long C terminus (FIG. 1). MSF is an oncofetal molecule produced during the fetal life but not by normal adult cells. Different reports however have described production of MSF by cancer-associated fibroblasts and by cancer cells. In this regard, inventors have documented the production of MSF in M2-polarized and tumor associated macrophages (TAMs, which have an M2-like phenotype and promote tumor proliferation and progression, angiogenesis and lymphangiogenesis, and inhibit adaptive immunity) [18]. WO9000567 refers to migration stimulating factor-1 which is a polypeptide capable of stimulating migration of normal adult fibroblasts which do not themselves produce the polypeptide and having an apparent molecular weight of 70 kD by polyacrylamide gel electrophoresis, which is cationic at physiological pH, is precipitated from aqueous solution by ammonium sulphate at 10% saturation or less, which is stable in solution at pH 2 but not at pH 10, is denatured at 56 DEG C. and is susceptible to trypsin and alkylation/reduction and which binds heparin. Other migration stimulating factors are similar but anionic. They are produced by foetal or foetal-like fibroblasts from cancer patients (but not normal adult skin fibroblasts) and their production may be used as a diagnostic or prognostic indicator of various cancers. Present inventors' observation of MSF production by M2-polarized macrophages prompted them to investigate whether MSF can be used as diagnostic and prognostic marker. Generation of a mouse monoclonal antibody (named mAb7.1) raised against a synthetic peptide spanning the aforementioned C-terminal tail of human MSF (i.e., VSIP-PRNLGY [SEQ ID NO: 11]) has been documented [19, 24]. It has been previously reported that the antibody mAb7.1 recognizes rhMSF in a Dot Blot setting [19], however no data are available on applications of this antibody in ELISA. In addition, based on available evidence, use of this antibody is limited to Immunohystochemistry procedures [19,23,20]. Therefore, it is still felt the need of an antibody that is able to detect MSF, without binding fibronectin-1, in different experimental settings.

SUMMARY OF THE INVENTION

To this end, inventors generated a mouse monoclonal antibody (named 1G5.3) that selectively recognizes MSF and allows effective quantitation of the MSF levels in biological fluids from individuals with pathological conditions associated to M2 polarization of macrophages. This antibody was developed immunizing mice with recombinant human MSF (rhMSF), and specifically recognizes the unique 10 amino-acid long C-terminal tail of the protein (aa 648-657). Here, inventors show that, when compared to known antibody, as the above disclosed mAb7.1 antibody (also named mabVSI7.1 in Cancer Res. 2005 Dec. 1; 65(23): 10742-9), for recognition of rhMSF and its C-terminus (i.e., in the form of a biotinylated synthetic peptide, biot-VSIP-PRNLGY [SEQ ID NO: 11] [decapeptide specific of MSF (aa. 648-657 of SEQ ID NO:4) that contains a biotin moiety linked to the NH2-terminal via an aminohexanoic (Ahx) arm, biot-Ahx-VSIPPRNLGY) in Dot Blot and ELISA settings, only the antibody of the present invention recognizes the biot-VSIPPRNLGY (SEQ ID NO:11) peptide (i.e., the C-terminal unique tail of MSF) and rhMSF under typical ELISA conditions. Moreover, the antibody according to the invention recognizes biot-VSIPPRNLGY (SEQ ID NO:11) peptide and rhMSF in a dose-depending fashion, both in a conditioned medium and as a purified molecule. In addition, the purified antibody of the invention specifically detects rhMSF in Dot Blot experiments, which extends the range of applications of this antibody to Dot Blot. These results indicate that the antibody according to the invention is unique in its ability to recognize MSF in different experimental settings, most importantly in ELISA immunoassays designed to measure the MSF levels in biological fluids.

DETAILED DESCRIPTION OF INVENTION

The authors of the present invention have produced a monoclonal antibody, called 1G5.3, obtained by immunizing BALB/c mice with recombinant human MSF (rhMSF). The hybridoma clone secreting this antibody was selected based on specificity and selectivity of the antibody's binding to rhMSF by indirect ELISA. The antibody made by the selected hybridoma indeed does not recognize hFn1.

It is therefore an object of the present invention an antibody able to recognize and bind to an epitope comprised in the sequence VSIPPRNLGY (from aa 648 to aa. 657 of SEQ ID No: 4 [SEQ ID NO:11]) of human Migration Stimulating Factor (MSF), and that doesn't recognize and bind human Fibronectin 1 (hFn1).

Preferably, said epitope consists of the sequence VSIPPRNLGY (from aa. 648 to aa 657 of SEQ ID No: 4 (SEQ ID NO:11)) of human Migration Stimulating Factor (MSF).

Another object of the invention is an antibody able to recognize and bind to human Migration Stimulating Factor (MSF), and that doesn't recognize and bind human Fibronectin 1 (hFn1). Preferably, the antibody according to the invention is characterized in that it is obtained making use of the peptide of sequence VSIPPRNLGY (from aa. 648 to aa. 657 of SEQ ID No: 4 (SEQ ID NO:11)). In the peptide of sequence VSIPPRNLGY (SEQ ID NO:11) used to obtain the antibody of the invention a cysteine was preferably added at the COOH terminal (see SEQ ID NO:9) and, more preferably, the peptide was conjugated to Keyhole limpet hemocyanin (KLH). In a preferred embodiment, the antibody according to the invention is selected from the group consisting of IgG, IgM, IgA and IgE antibodies.

In a preferred embodiment the antibody according the invention is able to recognize and bind MSF in an immunoassay, preferably an enzyme-linked immunosorbent assay (ELISA).

Preferably the antibody according to the invention comprises:
a complementarity determining region 3 of the heavy chain (CDRH3) having at least 80% of identity to the amino acid sequence WDY (SEQ ID NO: 12) (aa. 120-122 of SEQ. ID No. 6) and/or
a complementarity determining region 3 of the light chain (CDRL3) having at least 80% of identity to the amino acid sequence QSYNLHT (SEQ ID NO: 15) (aa. 116-122 of SEQ. ID No. 8).

More preferably it comprises:
a complementarity determining region 3 of the heavy chain (CDRH3) comprising the sequence of SEQ. ID No. 12 and/or
a complementarity determining region 3 of the light chain (CDRL3) comprising the sequence of SEQ. ID No. 15.

Preferably, the antibody according the invention comprises:
a complementarity determining region 3 of the heavy chain (CDRH3) having at least 80% of identity to the amino acid sequence WDY (SEQ ID NO: 12) (aa. 120-122 of SEQ. ID No. 6), preferably said CDRH3 comprising the sequence of SEQ ID NO:12, and/or
a complementarity determining region 2 of the heavy chain (CDRH2) having at least 80% of identity to the amino acid sequence EIRMKSDNYATYYAESVKG (SEQ ID NO: 13) (aa. 69-87 of SEQ. ID No. 6), preferably said CDRH2 comprising the sequence of SEQ ID NO:13, and/or
a complementarity determining region 1 of the heavy chain (CDRH1) having at least 80% of identity to the amino acid sequence NDWMN (SEQ ID NO: 14) (aa. 50-54 of SEQ. ID No. 6), preferably said CDRH1 comprising the sequence of SEQ. ID No. 14, and/or
a complementarity determining region 3 of the light chain (CDRL3) having at least 80% of identity to the amino acid sequence QSYNLHT (SEQ ID NO: 15) (aa. 116-122 of SEQ. ID No. 8), preferably said CDRL3 comprising the sequence of SEQ. ID No. 15, and/or
a complementarity determining region 2 of the light chain (CDRL2) having at least 80% of identity to the amino acid sequence WASTRYS (SEQ ID NO: 16) (aa. 76-82 of SEQ. ID No. 8), preferably said CDRL2 comprising the SEQ. ID No. 16, and/or
a complementarity determining region 1 of the light chain (CDRL1) having at least 80% of identity to the amino acid sequence RSSHYLLNSRTRKNFLS (SEQ ID NO: 17) (aa. 44-60 of SEQ. ID No. 8), preferably said CDRL1 comprising the sequence of SEQ. ID No. 17.

Said complement determining region (CDR) peptide is preferably a CDR3 peptide comprising an amino acid sequence selected from the group consisting of: WDY (SEQ ID NO: 12) (aa. 120-122 of SEQ. ID No. 6) and QSYNLHT (SEQ ID NO: 15) (aa. 116-122 of SEQ. ID No. 8).

More preferably, the antibody according to the invention comprises:
a complementarity determining region 3 of the heavy chain (CDRH3) having at least 80% of identity to the amino acid sequence WDY (SEQ ID NO: 12) (aa. 120-122 of SEQ. ID No. 6), preferably said CDRH3 comprising the sequence of SEQ. ID No. 12 or
a complementarity determining region 3 of the light chain (CDRL3) having at least 80% of identity to the amino acid sequence QSYNLHT (SEQ ID NO: 15) (aa. 116-122 of SEQ ID No. 8), preferably said CDRL3 comprising the sequence of SEQ ID No. 15.

Even more preferably, the antibody according to the invention comprises:
a complementarity determining region 3 of the heavy chain (CDRH3) having at least 80% of identity to the amino acid sequence WDY (SEQ ID NO: 12) (aa. 120-122 of SEQ. ID No. 6), preferably said CDRH3 comprising the sequence of SEQ. ID No. 12, and a complementarity determining region 3 of the light chain (CDRL3) having at least 80% of identity to the amino acid sequence QSYNLHT (SEQ ID NO: 15) (aa. 116-122 of SEQ ID No. 8), preferably said CDRL3 comprising the sequence of SEQ ID No. 15.

The antibody according to the invention preferably comprises a variable region of the heavy chain comprising a sequence having at least 80% of identity to the amino acid sequence (SEQ ID NO: 18)
EVKIEESGGGLVQPGGSMKLSCVASGFTFSNDWMNWVRQSPEKGLEWVAE

IRMKSDNYATYYAESVKGRFTISRDDSKNSVYLQMNNLRAEDNGIYYCTS

WDYWGQGTTLTVSS (aa. 20-133 of SEQ ID No. 6)

and/or
a variable region of the light chain comprising a sequence having at least 80% of identity to the amino acid sequence (SEQ ID NO: 19)
DIVMSQSPSSLAVSTGEKVTMNCRSSHYLLNSRTRKNFLSWYQQKPGQSP

QLLIYWASTRYSGVPDRFTGSGSGTDFTLTISSVQAEDLAVYYCKQSYNL

HTFGGGTKLEIK (aa. 21-132 of SEQ ID No. 8).

More preferably the antibody according to the invention comprises:
the variable region of the heavy chain comprising the amino acid sequence:

(SEQ ID NO: 18)
EVKIEESGGGLVQPGGSMKLSCVASGFTFSNDWMNWVRQSPEKGLEWVAE

IRMKSDNYATYYAESVKGRFTISRDDSKNSVYLQMNNLRAEDNGIYYCTS

WDYWGQGTTLTVSS (aa. 20-133 of SEQ ID No. 6)

and/or
the variable region of the light chain comprising the amino acid sequence:

(SEQ ID NO: 19)
DIVMSQSPSSLAVSTGEKVTMNCRSSHYLLNSRTRKNFLSWYQQKPGQ

SPQLLIYWASTRYSGVPDRFTGSGSGTDFTLTISSVQAEDLAVYYCKQ

SYNLHTFGGGTKLEIK (aa. 21-132 of SEQ ID No. 8).

Even more preferably the antibody according to the invention comprises a sequence having at least 80% of identity to the amino acid sequence of SEQ ID NO:6 and/or SEQ ID NO:8. More preferably the antibody according to the invention comprises a heavy chain consisting essentially of the amino acid sequence of SEQ ID No. 6 and/or a light chain consisting essentially of the amino acid sequence of SEQ ID No. 8.

A further object of the invention is an antibody able to recognize and bind the epitope that is recognized by the antibody as defined above, and that doesn't recognize and bind human Fibronectin 1 (hFn1).

Preferably the antibody according to the invention is selected from the group consisting of monoclonal antibodies, chimeric antibodies, humanized antibodies, deimmunized, fully human antibody, single chain antibodies, bispecific antibodies, diabodies, scFv, Fab, F(ab)'2, and di-, oligo- or multimers thereof.

A further object of the invention is an in vitro or ex-vivo method for selectively detecting and/or measuring the amount of the protein MSF or fragments thereof comprising the step of detecting MSF or fragments thereof in an isolated biological sample obtained from the subject by means of a specific ligand which is able to recognize and bind to an epitope comprised in the sequence VSIPPRNLGY (SEQ ID NO: 11) (from aa. 648 to aa 657 of SEQ ID No. 4) of human Migration Stimulating Factor (MSF), and that doesn't recognize and bind human Fibronectin 1 (hFn1), preferably said ligand being an antibody, more preferably said antibody being the antibody as defined above.

Another object of the invention is an in vitro or ex vivo method for assessing the risk and/or for diagnosing and/or for prognosing and/or for monitoring the progression and/or for monitoring the efficacy of a therapeutic treatment and/or for the screening of a therapeutic treatment of cancer or of an inflammatory pathology, preferably asthma or allergies, in a subject comprising the steps of:
a) detecting or measuring the amount or the activity of the protein MSF or of fragments thereof or of the polynucleotide coding for said protein or of fragments thereof in an isolated biological sample obtained from the subject and
b) comparing with respect to a proper control.

Preferably in the in vitro or ex vivo method for assessing the risk and/or for diagnosing and/or for prognosing and/or for monitoring the progression and/or for monitoring the efficacy of a therapeutic treatment and/or for the screening of a therapeutic treatment of cancer or an inflammatory pathology as above defined, the detection and/or measurement of the amount of the protein MSF or of fragments thereof is carried out by means of a specific ligand which is able to recognize and bind to an epitope comprised in the sequence (VSIPPRNLGY (SEQ ID NO:11)) from aa. 648 to aa. 657 of SEQ ID No. 4 of human Migration Stimulating Factor (MSF), and that doesn't recognize and bind human Fibronectin 1 (hFn1), preferably said ligand being an antibody, more preferably said antibody is as defined above.

Said detection and/or measurement of the amount of the protein MSF or of fragments thereof is preferably carried out by an immunoassay, preferably an ELISA assay.

The in vitro or ex vivo method according to the invention preferably comprises the steps of:
a) contact and incubation of the biological sample with the above defined antibody thereby forming a MSF-antibody complex, if MSF is present;
b) separation of the biological sample from the MSF-antibody complex;
c) selective detection of MSF bound to the antibody and/or quantifying the amount of MSF bound to the antibody using detecting means for the antibody;
d) comparison of the result obtained in c) to a control result.

Preferably the antibody is immobilized to a solid support, more preferably the immobilized antibody being coated on a plate, preferably a microtiter plate.

The detecting means is preferably a detectable antibody. A detectable antibody is preferably directly detectable, optionally the detectable antibody is amplified by a fluorimetric reagent, further optionally wherein the detectable antibody is biotinylated, and the detection means is avidin or streptavidin-peroxidase and 3,3',5,5'-tetramethyl benzidine or the detectable antibody is conjugated to alkaline phosphatase, and the detection means is p-nitrophenyl phosphate and/or 4-methylumbelliferyl phosphate.

Said detection and/or measurement of the amount of the protein MSF or of fragments thereof is preferably carried out by an ELISA assay.

Another object of the invention is the use of the antibody as above defined for detecting and/or quantifying the protein MSF or fragment thereof in an isolated biological sample, preferably wherein the detection of MSF or fragment thereof allows to determinate the presence of M2 polarized macrophages and/or M2-like tumour associated macrophages in the subject. A further object of the invention is the antibody as defined above for medical use.

Another object of the invention is a molecule able to modulate the expression and/or function of MSF for use in the prevention and/or treatment of cancer or of an inflammatory pathology, preferably asthma or allergies, wherein said molecule is preferably able to selectively deplete M2 polarized macrophages and/or M2-like tumour associated macrophages, said molecule being preferably the antibody as defined above.

A further object of the invention is a pharmaceutical composition comprising at least one antibody as defined above and pharmaceutical acceptable excipients, preferably said composition being for use by parenteral administration, preferably intravenously.

Other objects of the invention are a nucleic acid molecule encoding the antibody as defined above, preferably comprising a nucleotide sequence essentially consisting of:

```
                                              (SEQ ID NO: 20)
GAAGTGAAAATTGAGGAGTCTGGAGGAGGCTTGGTGCAACCTGGAGGA

TCCATGAAACTCTCCTGTGTTGCCTCTGGATTCACTTTCAGTAACGAC

TGGATGAACTGGGTCCGCCAGTCTCCAGAGAAGGGGCTTGAGTGGGTT

GCTGAAATTAGAATGAAATCTGATAATTATGCAACATATTATGCGGAG

TCTGTGAAAGGGAGGTTCACCATCTCAAGAGATGATTCCAAAAATAGT

GTCTACCTGCAAATGAACAATTTAAGAGCTGAAGACAATGGCATTTAT

TACTGTACCAGTTGGGACTACTGGGGCCAAGGCACCACTCTCACAGTC

TCCTCA (nt. 58-399 of SEQ ID No.5)
and/or (SEQ ID NO: 21)
GACATTGTGATGTCACAGTCTCCATCCTCCCTGGCTGTGTCAACAGGA

GAGAAGGTCACTATGAACTGCAGATCCAGTCACTATCTGCTCAACAGT

AGAACCCGAAAGAACTTCTTGTCTTGGTACCAACAGAAACCAGGACAG

TCTCCTCAACTGCTGATCTACTGGGCATCCACTAGGTATTCTGGGGTC

CCTGATCGCTTCACAGGCAGTGGATCTGGGACAGATTTCACTCTCACC

ATCAGCAGTGTGCAGGCTGAAGACCTGGCAGTTTATTACTGCAAACAA

TCTTATAATCTTCACACGTTCGGAGGGGGGACCAAGTTGGAAATAA

AG (nt. 61-396 of SEQ ID No. 7),
``` an expression vector encoding the antibody as defined above, preferably comprising said nucleic acid or a host cell comprising said nucleic acid, or said expression vector.

Even more preferably the nucleic acid sequence according to the invention has at least 80% of identity to the sequence of SEQ ID NO:20 and/or SEQ ID NO:21. More preferably the nucleic acid sequence according to the invention consist essentially of SEQ ID No. 20 and/or SEQ ID No. 21. Even more preferably the nucleic acid sequence according to the invention consist essentially of SEQ ID No. 5 and/or SEQ ID No. 7.

Another object of the invention is a kit for detecting and/or quantifying protein MSF or fragments thereof in a biological sample comprising the antibody as defined above and optionally detecting and/or quantifying means for the complex antigen-antibody, and the use of said kit for carrying out the above defined methods.

Preferably the kit further comprises a solid support wherein the antibody is immobilized, said solid support being preferably a microtitration plate.

Further objects of the invention are the use of the above defined kit for carrying out the above defined method and the kit as above defined for use in a method for the diagnosis and/or for predicting the risk of development and/or for the prognosis and/or for monitoring the progression and/or for monitoring the efficacy of a therapeutic treatment and/or for the screening of a therapeutic treatment of a cancer or an inflammatory pathology in a biological sample of a subject.

Preferably the above defined method is an immunoassay, more preferably an ELISA, and/or it detects and/or quantifies the human MSF in the biological sample.

In the above methods, an amount or activity of said protein MSF or of fragments thereof or of said polynucleotide or of fragments thereof in the isolated biological sample obtained from the subject higher than the control amount or activity indicates that the subject is either at increased risk for developing or is affected by the disease.

Preferably the biological sample is isolated from a human subject, optionally wherein the human subject is a cancer patient or a patient with an inflammatory pathology and the measuring step a) further comprises a comparison with a standard curve to determine the level of MSF compared to a normal individual. Preferably the biological sample is tumor lysates, plasma, serum or urine. The in vitro method for monitoring the progression and/or for monitoring the efficacy of a therapeutic treatment of the disease, as defined above, preferably comprises the steps of:

a) measuring the alteration of the amount or the alteration of the activity of the protein MSF or of fragments thereof or of the polynucleotide coding for said protein or of fragments thereof in said isolated biological sample obtained from the subject and b) comparing the measured alteration of step a) with a proper control alteration.

Preferably, the in vitro method for assessing the risk and/or diagnosing and/or prognosing of cancer or of an inflammatory pathology, preferably asthma or allergies as above defined, comprises the steps of:

a) measuring the amount or the activity of the protein MSF or of fragments thereof or of the polynucleotide coding for said protein or fragments thereof in said isolated biological sample obtained from the subject and b) comparing the measured amount or activity of step a) with a proper control amount or activity, wherein an amount or activity of said protein MSF or of fragments thereof or of said polynucleotide or of fragments thereof in the isolated biological sample obtained from the subject higher than the control amount or activity indicates that the subject is either at increased risk for developing or is affected by cancer or an inflammatory pathology.

Preferably, the in vitro method for monitoring the progression and/or for monitoring the efficacy of a therapeutic treatment of cancer or of an inflammatory pathology, as above defined, comprises the steps of:

a) measuring the alteration of the amount or the alteration of the activity of the protein MSF or of fragments thereof or of the polynucleotide coding for said protein or fragments thereof in said isolated biological sample obtained from the subject and b) comparing the measured alteration of step a) with a proper control alteration.

In a preferred aspect of the invention, the step a) of the above defined methods is carried out by the method for detecting and/or measuring the amount of MSF protein or of fragments thereof as above defined. The antibody of the invention may be used to purify by Immuno-Affinity Chromatography (IAC) rhMSF secreted in the culture supernatant, e.g of cell lines transfected with DNA sequences coding for rhMSF, as indicated above, and/or the natural (non-recombinant) MSF protein expressed and secreted in vivo and in vitro, for example, by M2 macrophages, oncofetal fibroblasts and cancer cells The antibody of the invention may also be used in immunohistochemistry for recognizing MSF in human tissues, under both physiological and pathological conditions, with major regard to cancer In preferred embodiment, an amount of MSF, in the isolated biological sample obtained from the subject, higher than the control amount indicates that the subject is either affected by or is at increased risk for developing a cancer or an inflammatory pathology.

In an alternative embodiment of the method of the invention, an amount of MSF, in the isolated biological sample obtained from the subject, lower than the control amount indicates that the subject is going toward an amelioration of the pathology. In the present invention, a proper control may be selected from a value measured in a healthy patient, a patient affected by a non-inflammatory pathology or who is not affected by cancer, a patient affected by an inflammatory or a cancer pathology before a therapeutic treatment, a patient affected by an inflammatory pathology or cancer during the time course of a therapeutic treatment, a patient affected by an inflammatory pathology or cancer at various time points during the course of the disease. The isolated biological sample of the above defined methods is preferably plasma, blood, serum, tissue obtained by surgical resection, tissue obtained by biopsy, cells culture, cell supernatants, cell lysates, tissue samples, organs, bone marrow. It is also an object of the invention a method for the treatment and/or prevention of cancer or other inflammatory disorders comprising administering to a subject antibody according to the invention. A further object of the invention is an expression vector encoding the antibody as above defined, preferably comprising the nucleic acid as above defined. Another object of the invention is a host cell comprising the nucleic acid as above defined, or the vector as above defined, and a method to produce the antibody as above defined comprising the steps of culturing the above host cell and purifying the antibody from the cell culture. In other embodiments of the invention a device or kit is provided for the analysis of patient samples. Alternatively, the reagents can be provided as a kit comprising reagents in a suspension or suspendable form, e.g. reagents bound to beads suitable for flow cytometry, preferably magnetic beads coated with antibody capture, or customized dried antibody cocktails for Multicolor analysis and/or columns with sized filter cartridges, and/or combined with specific antibody filter (SAF) and the like. The instructions may comprise instructions for conducting an antibody-based flow cytometry assay. Detecting means are preferably means able to detect and/or measure the amount of MSF, e.g. means able to detect the complex antigen-antibody, as enzyme conjugated secondary antibodies, luminescent substrates, magnetic beads coated with antibody capture, customized dried antibody cocktails and/ or columns with size filter cartridges and/or combined with specific antibody filter (SAF). Preferably said kit further comprises a solid support wherein the antibody is immobilized. Preferably, the kit of the invention is an immunoassay kit, more preferably an ELISA kit. The means for detecting and/or quantifying the antigen-antibody complex may be means for detecting and/or quantifying the catalytic activity of MSF such as secondary antibodies conjugated to enzymes, luminescent substrates. These means are known in the art. The kit according to the invention can further comprise typical auxiliary components, such as buffers, carriers, dyes, etc. and/or instructions for use. The kit can further comprise control means for comparing the increase in the amount of MSF with an appropriate control value. The control value can be obtained, for example, with reference to known standards, either from a normal subject or a normal population. In the present invention, the "control result" can be the result obtained for a sample isolated from a healthy subject or from a patient affected by another disorder than cancer and inflammatory diseases.

In the case of a method for monitoring the progression of the cancer and inflammatory diseases, the control result could be the result of a sample isolated from the same subject at various points in time prior to the start-up of the therapy, at various points in time during the therapy, etc. In the case of a method for monitoring the efficacy of a therapy, the control sample can be a sample taken from the same subject prior to the start-up of the therapy or taken at various times during the therapy. By "monitoring the efficacy" it is meant monitoring the pharmacological profile of an agent. In the case of a method for screening a treatment of cancer and inflammatory diseases, the control sample can be a sample taken from an untreated subject or a subject treated with a substance to be tested or a subject treated with a reference treatment. Reference treatment for a specific cancer and inflammatory diseases is known to the skilled in the art. By "screening" it is meant assessing whether an agent has a biological or pharmacological activity on cancer and inflammatory diseases. In the present invention, the expression "detect" or "detection" refers to any use of any method of observation, assessment or quantification of the signals indicative of the antibody's presence in a sample or the absolute or relative amount of said antibody in a sample, for example by chemiluminescence, fluorimetry, spectrophotometry, etc. In the present invention, the expression "quantify" or "quantification" can be understood as measuring the amount or concentration or level of MSF or of the respective antibody, preferably with a semi-quantitative or quantitative method. The term "amount", as used in the description refers to but is not limited to the absolute or relative amount of proteins, and any other value or parameter associated with the latter or which can derive therefrom. Such values or parameters comprise signal intensity values obtained either for physical or chemical properties of the protein, obtained by direct measurement, for example, intensity values in an immunoassay, mass spectroscopy or nuclear magnetic resonance. Moreover, these values or parameters include the ones obtained by indirect measurement.

The above defined antibodies comprise human and animal monoclonal antibodies or fragments thereof, single chain antibodies and fragments thereof and miniantibodies, bispecific antibodies, diabodies, triabodies, or di-, oligo- or multimers thereof. Also included are peptidomimetics or peptides derived from the antibodies according to the invention, e.g. they comprise one or several CDR regions, preferably the CDR3 region. Further included are human monoclonal antibodies and peptide sequences which, based on a structure activity connection, are produced through an artificial modeling process (Greer J. et al., J. Med. Chem., 1994, Vol. 37, pp. 1035-1054). Preferably, the antibody is selected from the group consisting of an intact immunoglobulin (or antibody), a Fv, a scFv (single chain Fv fragment), a Fab, a F(ab')$_2$, an antibody-like domain, an antibody-mimetic domain, a single antibody domain, a multimeric antibody, a peptide or a proteolytic fragment containing the epitope binding region. The term "antibody" in the present invention is used in the most general sense, and encompasses various antibodies and antibody mimetic structures, including, but not limited to, monoclonal antibodies, polyclonal antibodies, multispecific antibodies (e.g., bispecific antibodies), human antibodies, humanized antibodies, deimmunized antibodies, chimeric antibodies, nanobodies, antibody derivatives, antibody fragments, anticalines, DARPins, affibody, affilins, affimers, affitines, alphabody, avimers, fynomers, minibodies and other binding domains, provided that they show desired binding activity for the antigen. Antigen-binding fragments of such antibodies may be produced by conventional techniques. Examples of such fragments include, but are not limited to, Fab, F(ab')$_2$, and Fv fragments. Antibody fragments and derivatives produced by genetic engineering techniques are also contemplated for use. Unless otherwise specified, the terms "antibody" and "monoclonal antibody" as used herein encompass both whole antibodies and antigen-binding fragments thereof. An "antibody fragment" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$^2$; diabody; linear antibodies; single-chain antibody molecules (e.g. scFv); and multispecific antibodies consisting of antibody fragments. Fv of VH and VL are also called "nanobodies". The term "mimetic antibody" refers to those organic compounds or binding domains that are not antibody derivatives but that can specifically bind to an antigen, in the same way of the antibodies. They include anticalines, DARPins, affibody, affilins, affimers, affitines, alphabody, avimers, fynomers, minibodies, and others. The term "chimeric" antibody refers to an antibody in which a portion of the heavy and/or light chain is derived from one specific source or species, while the remainder of the heavy and/or light chain is derived from a different source or species. The terms "full-length antibody," "intact antibody" and "whole antibody" are used herein interchangeably to refer to an antibody having a structure substantially similar to a native antibody structure or having heavy chains that contain a Fc region as defined herein. A "human antibody" is one that possesses an amino acid sequence which corresponds to that of an antibody produced by a human being or a human cell or derived from a non-human source that uses repertoires of human antibodies or other sequences encoding human antibodies. This definition of a human antibody specifically excludes a humanized antibody comprising non-human antigen-binding residues. In humans, the antibody isotypes are IgA, IgD, IgE, IgG and IgM. An antibody "humanized" refers to a chimeric antibody comprising amino acid residues from non-human hypervariable regions (HVR) and amino acid residues from the remaining human regions (FR: Framework Regions). In certain embodiments, a humanized antibody will comprise substantially at least an entire variable domain, and typically two, in which all or substantially all of the HVRs (for example, CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, for example, a non-human antibody, refers to an antibody subjected to humanization. An antibody "deimmunized" is an antibody with reduced immunogenicity based on the destruction of HLA binding, a basic requirement for the stimulation of T cells. The term "monoclonal antibody" as used herein refers to an antibody obtained from a population of substantially homogeneous antibodies, i.e., the individual antibodies comprising the population are identical and/or bind the same epitope, except for possible antibodies variants, for example, containing naturally occurring mutations or that are generated during the production of a monoclonal antibody preparation, such variants generally being present in lower amounts. In contrast to polyclonal antibody preparations, which typically include different antibodies directed against different determinants (epitopes), each monoclonal antibody of a monoclonal antibody preparation is directed against a single determinant on an antigen. Therefore, the modifier "monoclonal" indicates that the character of the antibody is obtained from a substantially homogeneous population of antibodies, and should not be interpreted as the need to produce the antibody by any particular method. For example, the monoclonal antibodies to be used according to the present invention can be produced by a variety of techniques, including, but not limited to, the hybridoma method, methods based on recombinant DNA, phage display methods, and methods that use transgenic animals containing all or part of human immunoglobulin loci. In the context of the present invention, an "antibody that binds to MSF and doesn't recognize Fn1" includes modifications of the antibody according to the present invention able to maintain the specificity mentioned above. These changes include, for example, the conjugation to effector molecules such as chemotherapeutic or cytotoxic agents, and/or detectable reporter portions.

Bispecific antibodies are macromolecular, heterobifunctional cross-linkers having two different binding specificities within one single molecule. In this group belong, e.g., bispecific (bs) IgGs, bs IgM-IgAs, bs IgA-dimers, bs (Fab') 2, bs(scFv)2, diabodies, and bs bis Fab Fc (Cao Y. and Suresh M. R., Bioconjugate Chem., 1998, Vol. 9, pp. 635-644).

By peptidomimetics, protein components of low molecular weight are understood which imitate the structure of a natural peptide component, or of templates which induce a specific structure formation in an adjacent peptide sequence (Kemp D S, Trends Biotechnol., 1990, pp. 249-255). The peptidomimetics may, e.g., be derived from the CDR3 domains. Methodical mutational analysis of a given peptide sequence, i.e. by alanine or glutamic acid scanning mutational analysis, allows for the identification of peptide residues critical for procoagulant activity. Another possibility to improve the activity of a certain peptide sequence is the use of peptide libraries combined with high throughput screening.

The term antibodies may also comprise agents which have been obtained by analysis of data relating to structure-activity relationships. These compounds may also be used as peptidomimetics (Grassy G. et al., Nature Biotechnol., 1998, Vol. 16, pp. 748-752; Greer J. et al., J. Med. Chem., 1994, Vol. 37, pp. 1035-1054).

The term antibody may also include proteins produced by expression of an altered, immunoglobulin-encoding region in a host cell, e.g. "technically modified antibodies" such as synthetic antibodies, chimeric or humanized antibodies, or mixtures thereof, or antibody fragments which partially or completely lack the constant region, e.g. Fv, Fab, Fab' or F(ab)'2 etc. In these technically modified antibodies, e.g., a part or parts of the light and/or heavy chain may be substituted. Such molecules may, e.g., comprise antibodies consisting of a humanized heavy chain and an unmodified light chain (or chimeric light chain), or vice versa. The terms Fv, Fc, Fd, Fab, Fab' or F(ab)'$_2$ are used as described in the prior art (Harlow E. and Lane D., in "Antibodies, A Laboratory Manual", Cold Spring Harbor Laboratory, 1988).

The present invention also comprises the use of Fab fragments or F(ab)'2 fragments which are derived from monoclonal antibodies (mAb), which are directed against MSF. Preferably, the heterologous framework regions and constant regions are selected from the human immunoglobulin classes and isotypes, such as IgG (subtypes 1 to 4), IgM, IgA and IgE. In the course of the immune response, a class switch of the immunoglobulins may occur, e.g. a switch from IgM to IgG; therein, the constant regions are exchanged, e.g. from µ to y. A class switch may also be caused in a directed manner by means of genetic engineering methods ("directed class switch recombination"), as is known from the prior art (Esser C. and Radbruch A., Annu. Rev. Immunol., 1990, Vol. 8, pp. 717-735). However, the antibodies according to the present invention need not comprise exclusively human sequences of the immunoglobulin proteins. In one particular embodiment, a humanized antibody comprises complement determining regions (CDRs) from murine monoclonal antibodies which are inserted in the framework regions of selected human antibody sequences. However, human CDR regions can also be used. Preferably, the variable regions in the human light and heavy chains are technically altered by one or more CDR exchanges. It is also possible to use all six CDRs or varying combinations of less than six CDRs. The term antibody may also comprise agents which have been obtained by analysis of data relating to structure-activity relationships. These compounds may also be used as peptidomimetics (Grassy G. et al., Nature Biotechnol., 1998, Vol. 16, pp. 748-752; Greer J. et al., J. Med. Chem., 1994, Vol. 37, pp. 1035-1054).

The antibodies of the present invention also include those for which binding characteristics have been improved by direct mutations, affinity maturation methods, phage display. The affinity or specificity can be modified or improved by mutations in any of the antibody CDRs of the present invention. The term "variable region" or "variable domain" refers to the domain of a heavy or light chain of antibody that is involved in the binding of the antibody to the antigen. The variable domains (or regions) of the heavy and light chain (VH and VL, respectively) of a native antibody generally have similar structures, each domain comprising four frameworks conserved regions (FR) and three hypervariable regions (HVR, see, for example, Kindt et al. Kuby Immunology, 6th ed., W.H. Freeman and Co., page 91, 2007). A single VH or VL domain can be sufficient to confer antigen binding specificity. Moreover, it is possible to isolate antibodies that bind to a specific antigen using a VH or VL domain from an antibody that binds the antigen to screen a library of complementary VL or VH domains, respectively (see, for example, Portolano et al., J. Immunol. 150:880-887, 1993; Clarkson et al., Nature 352:624-628, 1991).

In another aspect, the antibody or derivatives thereof comprises a variable domain sequence of the heavy chain (VH) and/or a variable domain sequence of the light chain (VL) having at least 80%, 85%, 90%, 91%, 92%, 93%, 94%, 95%, 96%, 97%, 98%, 99%, or 100% sequence identity to each of the CDRs comprised in the amino acid sequences of SEQ ID No: 6 or SEQ ID No: 8, respectively, as defined above. In certain embodiments, the VH sequence and/or the VL sequence having at least 80%, 85%, 90%, 91%, 92%, 93%, 94%, 95%, 96%, 97%, 98%, or 99% identity to aa. 20-133 of SEQ ID No. 6 or aa. 21-132 of SEQ ID No: 8, respectively, contains substitutions (e.g., conservative substitutions), insertions, or deletions as compared to the reference sequence, however, the anti-MSF antibody comprising this sequence maintains the ability to bind to the epitope. The antibody-like domain comprises binding proteins structurally related to antibodies, such as T cell receptors. The antibodies of the present invention also include functional equivalents that include polypeptides with amino acid sequences substantially identical to the amino acid sequence of the variable or hypervariable regions of the antibodies of the present invention.

In the present invention "at least 80% of identity" means that the identity may be at least 80%, 87% or 90% or 95% or 100% sequence identity to referred sequences. This applies to all the mentioned % of identity. Preferably, the % of identity relates to the full length of the referred sequence.

Sequences of the invention comprise amino acid sequences with at least 70, preferably at least 80%, and more preferably at least 90% identity or homology to the sequences described. "The percent (%) amino acid sequence identity" with respect to a reference polypeptide sequence is defined as the percentage of amino acid residues in a candidate sequence that are identical to the amino acid residues in the reference polypeptide sequence, after aligning the sequences and introducing gaps, if necessary, to achieve maximum percent sequence identity, and not considering any conservative substitutions as part of the sequence identity. The alignment in order to determine the percent of amino acid sequence identity can be achieved in various ways that are within the skill in the art, for instance, using publicly available computer software such as BLAST, BLAST-2, ALIGN or Megalign software (DNASTAR). Those skilled in the art can determine appropriate parameters for aligning sequences, including any algorithms needed to achieve maximal alignment over the full-length of the sequences being compared. The antibody of the invention may e.g. have a dissociation constant ($K_D$) of <100 nM, <10 nM, <1 nM, <0.1 nM, <0.01 nM, or <0.001 nM or less, e.g. from $10^{-8}$ M to $10^{-13}$ M, e.g., from $10^{-9}$ M to $10^{-13}$ M. Recombinant and/or biotechnological derivatives as well as fragments of the antibodies described above are included within the invention, provided that the binding activity of the antibodies and their functional specificity is maintained. The antibody as described above is used as a medicament, preferably for use in the treatment and/or prevention of cancer or inflammatory pathologies. The diseases that can be treated with the antibody of the invention are preferably tumour diseases, such as, for example, solid tumors (e.g. breast cancer, lung cancer, colorectal carcinoma, pancreatic carcinoma, e.g. pancreatic ductal adenocarcinoma (PDAC), glioma, prostate cancer, thyroid cancer, ovarian cancer, liver cancer, neuroblastoma, melanoma) and non-solid tumors (e.g. leukemia, multiple myeloma and lymphoma, chronic myeloproliferative neoplasms).

In the context of the present invention, in addition to cancers, the inflammatory pathologies include asthma, allergies, sepsis and infectious diseases; autoimmune diseases such as rheumatoid arthritis and autoinflammatory diseases such as inflammatory bowel disease; chronic degenerative diseases involving tissue remodeling and fibrosis such as idiopathic pulmonary fibrosis, liver chirrosis and chronic heart failure.

In the context of the present invention, the "cancer" or "tumour" includes primary and metastatic tumours, as well as refractory tumours, tumours expressing MSF, solid or non-solid tumours. Examples of solid tumours are: breast cancer, lung cancer, colorectal carcinoma, pancreatic carcinoma, e.g. pancreatic ductal adenocarcinoma, glioma, lymphoma, prostate cancer, thyroid cancer, ovarian cancer, liver cancer, neuroblastoma, melanoma. Examples of non-solid tumours are: leukemia, multiple myeloma and lymphoma, chronic myeloproliferative neoplasms A further aspect of the present invention is a nucleic acid encoding the antibody as defined above or hybridizing with the above nucleic acid, or consisting of a correspondent degenerated sequence. It is within the scope of the invention an expression vector encoding the antibody as defined above, preferably comprising the nucleic acid as defined above. It is within the scope of the invention a host cell comprising the nucleic acid as defined above, or the vector as defined above. The terms "host cell", "host cell line", and "host cell culture" are used interchangeably and refer to cells into which an exogenous nucleic acid has been introduced, including the progeny of such cells. The host cells include "transformants" and "transformed cells," which include the transformed primary cell and the progeny derived therefrom, without taking into account the number of steps. The progeny may be not completely identical in nucleic acid content to a parent cell, but may contain mutations. In the present invention, mutant progenies are included, which have the same function or biological activity as that for which they have been screened or selected in the originally transformed cell. The nucleic acids of the invention can be used to transform a suitable mammalian host cell. Mammalian cells available as expression hosts are well known and include, for example, CHO and BHK cells. Prokaryotic hosts include, for example, *E. coli, Pseudomonas, Bacillus*, etc. Antibodies of the invention can be fused to additional amino acid residues, such as tags that facilitate their isolation. The term "vector", as used in the present invention refers to a nucleic acid molecule capable of propagating another nucleic acid to which it is linked. The term includes the vector as a self-replicating nucleic acid structure as well as the vector incorporated into the genome of a host cell in which it was introduced. Certain vectors are capable of directing the expression of nucleic acids to which they are operably linked. In the present such vectors are referred to as "expression vectors." Any suitable expression vector can be used, for example prokaryotic cloning vectors such as plasmids from *E. coli*, such as colE1, pCR1, pBR322, pMB9, pUC. Expression vectors suitable for expression in mammalian cells include derivatives of SV-40, adenovirus, retrovirus-derived DNA sequences. The expression vectors useful in the present invention contain at least one expression control sequence that is operatively linked to the sequence or fragment of DNA that must be expressed. It is a further object of the invention a method of treatment and/or prevention of angiogenesis-related diseases, preferably tumour pathologies, as e.g. melanoma, glioblastoma, colorectal carcinoma, breast carcinoma, kidney carcinoma, ovary carcinoma, cervical carcinoma, non-small cell lung carcinoma and/or metastasis, retinopathies as diabetic retinopathy, neovascularization in age-related exudative macular degeneration, macular oedema induced by occlusion of retina artery, choroid neovascularization caused by pathologic myopia, comprising administering to a patient in need thereof a therapeutically effective amount of the antibody or a synthetic or recombinant fragment thereof as defined above. It is a further of the invention a pharmaceutical composition comprising at least the antibody or a synthetic or recombinant fragment thereof as defined above and pharmaceutical acceptable excipients, preferably said composition being for use by parenteral administration, in particular intravenously. The composition comprises an effective amount of the antibody and/or recombinant or synthetic antigen binding fragments thereof. The pharmaceutical compositions are conventional in this field and can be produced by the skilled in the art just based on the common general knowledge. The formulations useful in therapy as described herein may e.g. comprise the antibody as described above, in a concentration from about 0.1 mg/ml to about 100 mg/ml, preferably from 0.1 to 10 mg/ml, more preferably from 0.1 to 5 mg/ml. In other formulations, the antibody concentration may be lower, e.g. at least 100 pg/ml. The antibody of the invention is administered to the patient in one or more treatments. Depending on the type and severity of the disease, a dosage of e.g. about 1 mg/kg to 20 mg/kg of the antibody may be administered, for example in one or more administrations, or by continuous infusion. The antibodies of the present invention may be administered in combination with other therapeutic agents, in particular with antibodies able to neutralize other receptors involved in tumour growth or angiogenesis. Any method of administration may be used to administer the antibody of the present invention, in particular, for example, the administration may be oral, intravenous, intraperitoneal, subcutaneous, or intramuscular. The antibody according to the present invention may also be administered as a conjugate, which binds specifically to the receptor and releases toxic substances. In particular embodiments, the pharmaceutical composition of the present invention can be administered in the form of single dosage (for example, tablet, capsule, bolus, etc.). For pharmaceutical applications, the composition may be in the form of a solution, for example, of an injectable solution, emulsion, suspension, or the like. The vehicle can be any vehicle suitable from the pharmaceutical point of view. Preferably, the vehicle used is capable of increasing the entry effectiveness of the molecules into the target cell. In the pharmaceutical composition according to the invention, the antibody may be associated with other therapeutic agents, such as antagonists of other growth factor receptors involved in tumorigenesis or angiogenesis, such as VEGFR-2, EGFR, PDGFR, receptor kinase inhibitors, BRAF inhibitors, MEK inhibitors, immunomodulatory antibodies, anti-cancer agents, such as: bevacizumab, ramucirumab, aflibercept, sunitinib, pazopanib, sorafenib, cabozantinib, axitinib, regorafenib, nintedanib, lenvatinib, vemurafenib, dabrafenib, trametinib, chemotherapeutic agents such as methylating agents (temozolomide, dacarbazine), platinum compounds (cisplatin, carboplatin, oxaliplatin), taxanes (paclitaxel, nab-paclitaxel, docetaxel), fluoropyrimidines (5-fluorouracil, capecitabine), topoisomerase I inhibitors (irinotecan, topotecan), poly(ADP-ribose) polymerase inhibitors (PARP) (e.g., olaparib), etc. The pharmaceutical composition is chosen according to the demands of treatment. These pharmaceutical compositions according to the invention may be administered in the form of tablets, capsules, oral preparations, powders, granules, pills, liquid solutions for injection or infusion, suspensions, suppositories, preparations for inhalation. A reference for the formulations is the book by Remington ("Remington: The Science and Practice of Pharmacy", Lippincott Williams & Wilkins, 2000). The skilled in the art will choose the form of administration and the effective dosages, by selecting suitable diluents, adjuvants and/or excipients. The term "pharmaceutical composition" refers to a preparation that is in such a form as to permit to the biological activity of an active ingredient contained therein to be effective, and which contains no additional components which are unacceptably toxic to a subject to which the formulation may be administered. It is a further aspect of the invention a method for producing the antibody or a synthetic or recombinant fragment thereof as defined above, comprising the steps of culturing the host cell and purifying the antibody or a synthetic or recombinant fragment thereof from the cell culture.

In the context of the present invention the term "comprising" also includes the terms "having essentially" or "consisting essentially". In the present invention, the herein mentioned "protein(s)" also comprises the protein encoded by the corresponding orthologous or homologous genes, functional mutants, functional derivatives, functional fragments or analogues, isoform, splice variants thereof. In the present invention "functional" is intended for example as "maintaining their activity". As used herein "fragments" refers to polypeptides having preferably a length of at least 10 amino acids, more preferably at least 15, at least 17 amino acids or at least 20 amino acids, even more preferably at least 25 amino acids or at least 37 or 40 amino acids, and more preferably of at least 50, or 100, or 150 or 200 or 250 or 300 or 350 or 400 or 450 or 500 amino acids. "MSF fragment" as disclosed herein preferably comprises the sequence VSIPPRNLGY [from aa. 648 to aa. 657 of SEQ ID No: 4) (SEQ ID NO:11)) or fragments thereof.

The present invention will be described by means of non-limiting examples, referring to the following figures:

FIG. 1. Comparison of the domain structure of MSF and Fibronectin. MSF is a truncated isoform of hFn1 generated from the single-copy fibronectin gene by a read-through mechanism. The 70 kDa protein is identical to the N-terminus of hFn1 up to the amino acid sequence coded by exon III-1a with the addition of a unique 10 amino acids long peptide (VSIPPRNLGY (SEQ ID NO:11) [from aa. 648 to aa. 657 of SEQ ID No: 4 (NCBI Accession N. CAH60958.1]). Figure adapted from [20]. Functional domains in Fn1 and MSF: Hip1/Fib1: binding domains to heparin and fibrin; Gel-BD: binding domain to gelatin/collagen; Cell-BD: RGD-mediated binding to integrins; Hep2: high-affinity heparin binding domain; Fib2: C-terminal fibrin binding domain; IGD motifs: isoleucine-glycine-aspartate tripeptide motifs mediating the motogenic activity.

Figure 2:
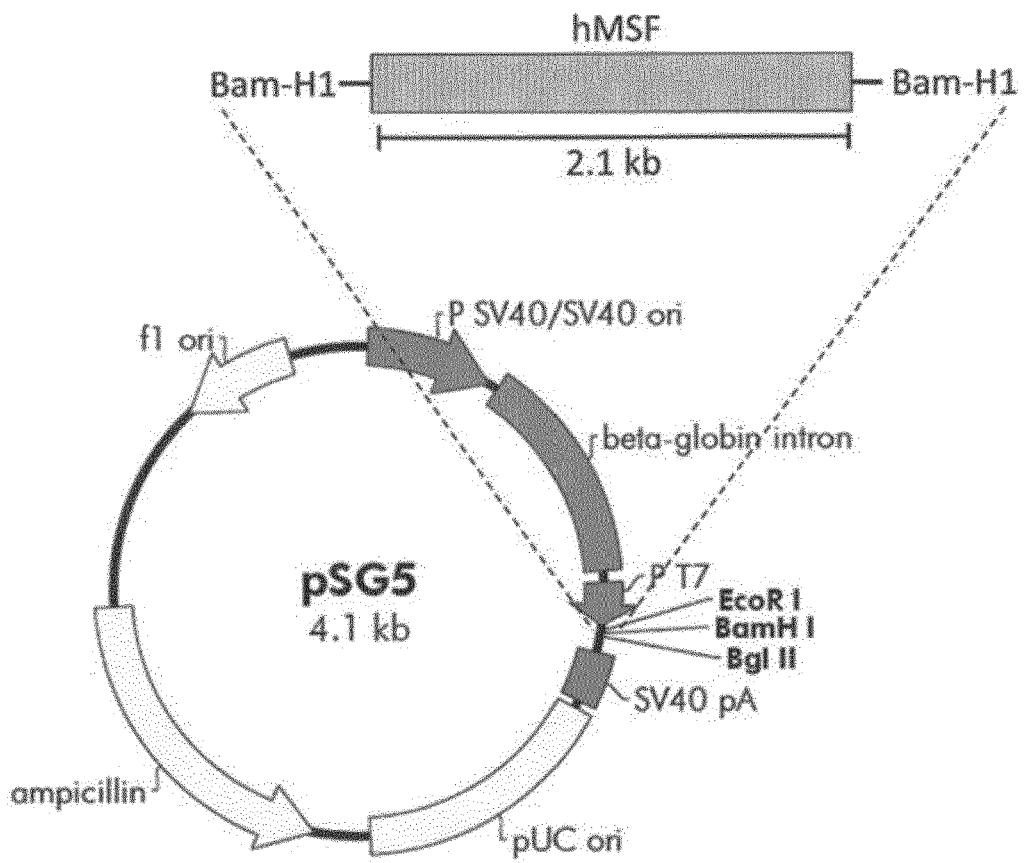

FIG. 2. Schematic representation of the expression vector used to transfect CHO cells and express recombinant human MSF. The complete cDNA sequence of human MSF has been sub-cloned in the BamH1 restriction site that is present in the vector.

Figure 3:
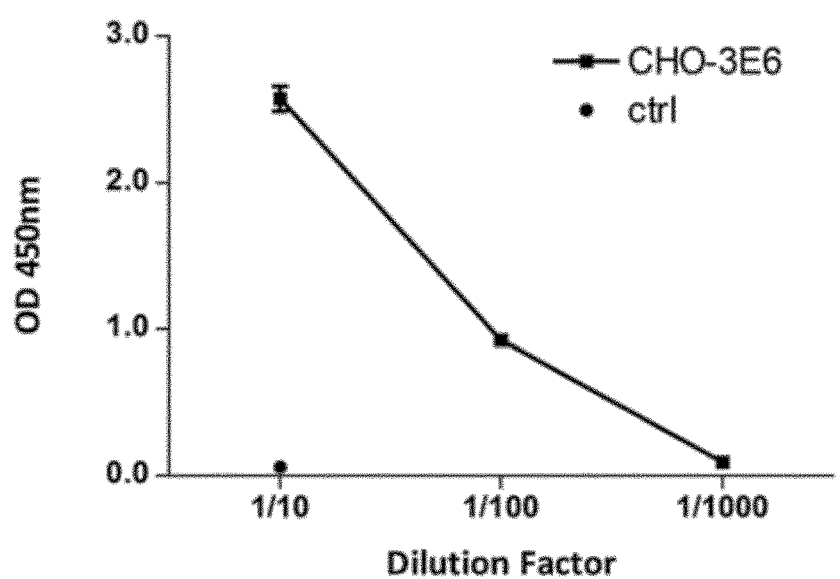

FIG. 3. Indirect ELISA on the conditioned medium from the rhMSF-expressing CHO-3E6 clone. Different dilutions of conditioned medium from the CHO-3E6 cell clone, which expresses rhMSF, were coated on plastic wells and bound MSF was revealed using a rabbit pAb.

Figure 4:
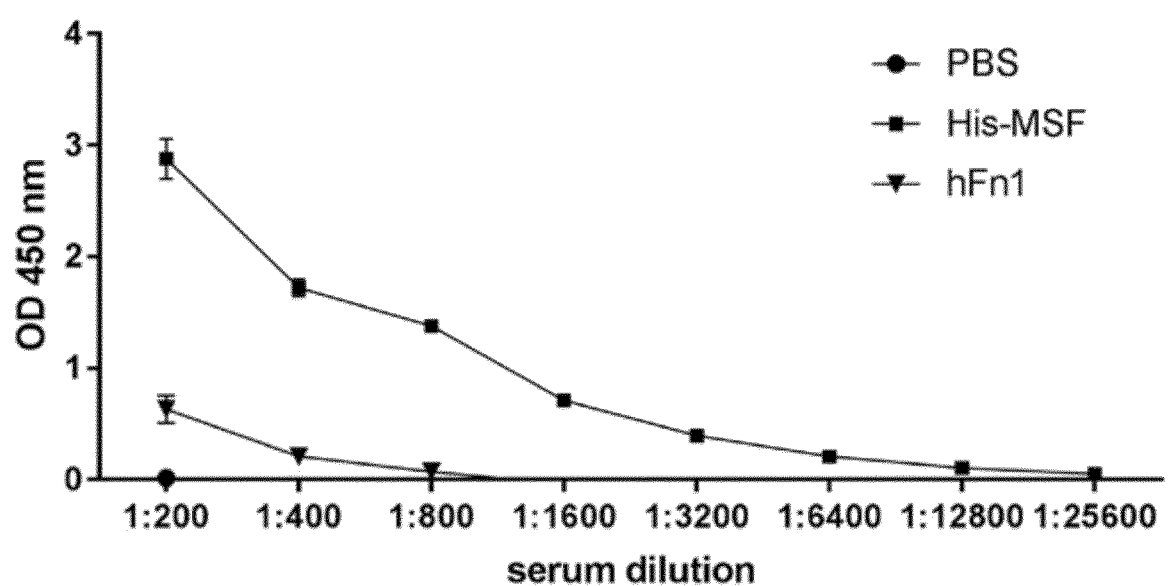

FIG. 4. Titration of serum from immunized mice. Serum was collected from an immunized mouse after several cycles of immunization, and analyzed by ELISA. Different dilutions of serum were applied to multi-wells plates coated with PBS, human Fibronectin 1 (hFn1) and His-MSF. After incubation with anti-mouse secondary antibody and addition of chromogenic substrate, absorbance at 450 nm was recorded. Reported absorbance values refer to mean values obtained in duplicate wells.

FIG. 5. Primary screening of hybridoma conditioned media by indirect ELISA. Conditioned media from hybridomas cultured in 96-wells plates were assessed by ELISA for recognition of human MSF. Briefly, 50 microliters of each medium were applied to multi-wells plates coated with the MSF VSIPPRNLGY (SEQ ID NO:11) (from aa 648 to aa. 657 of SEQ ID No: 4) unique decapeptide or conditioned medium from rhMSF-expressing CHO-3E6 cells, as indicated. After incubation with a suitable secondary antibody and addition of the chromogenic substrate, absorbance at 450 nm was recorded. Reported absorbance values refer to single wells.

FIG. 6. Secondary screening of hybridoma conditioned media by indirect ELISA. Selected hybridomas (from primary screening, see FIG. 5) were subcloned and cultured in 96-wells cell culture plates. Conditioned media were subsequently tested by indirect ELISA to detect antibodies recognizing human MSF. Briefly, 50 microliters of hybridoma culture supernatants were applied to multi-wells plates coated with the MSF VSIPPRNLGY (SEQ ID NO:11) (from aa 648 to aa. 657 of SEQ ID No: 4) unique decapeptide or conditioned medium from rhMSF-expressing CHO-3E6, as indicated. After incubation with a suitable secondary antibody and addition of a chromogenic substrate, absorbance at 450 nm was recorded and reported, as described in FIG. 5. Negative controls (buffer) are in wells 1 A & 1B (anti mouse IgG) and 1E & 1F (anti rabbit IgG); positive controls (peptide or supernatant from CHO-3E6) are in wells 1C & 1D (rabbit pAb).

Figure 7:
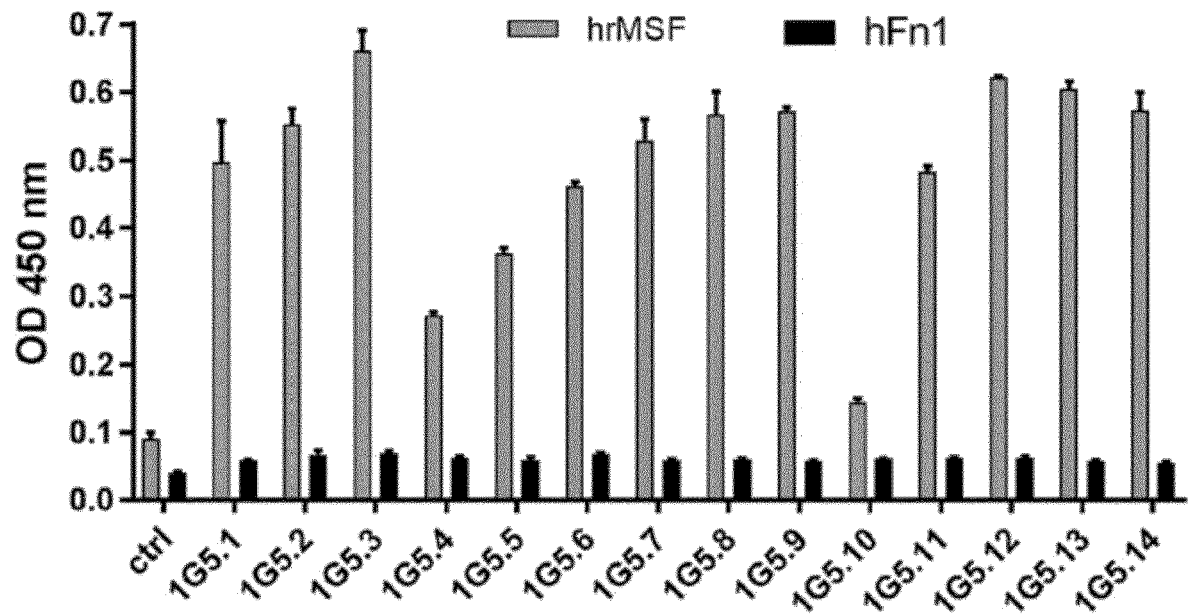

FIG. 7. Screening of fourteen clones (selected from secondary screening) following subcloning at 0.5 cells/well. 96-wells plates were coated with concentrated conditioned medium from rhMSF-expressing CHO-3ES (50 µl/well) or human hFn1 (1 µg/well). Each clone was tested in duplicate wells and data are expressed as mean OD measured at 450 nm±SD.

Figure 8:
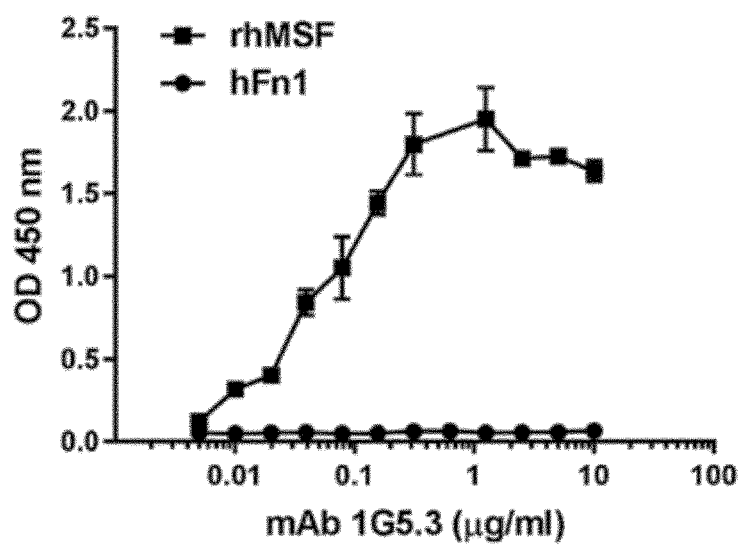

FIG. 8. Titration of the 1G5.3 monoclonal antibody by ELISA. Wells of a microtiter plate were coated with human rhMSF or hFn1 (0.5 µg/ml) and incubated with different dilutions of 1G5.3, ranging from 10 µg/ml to 0.005 ng/ml in duplicate wells. Data are expressed as OD measured at 450 nm (MEAN±SD).

Figure 9:
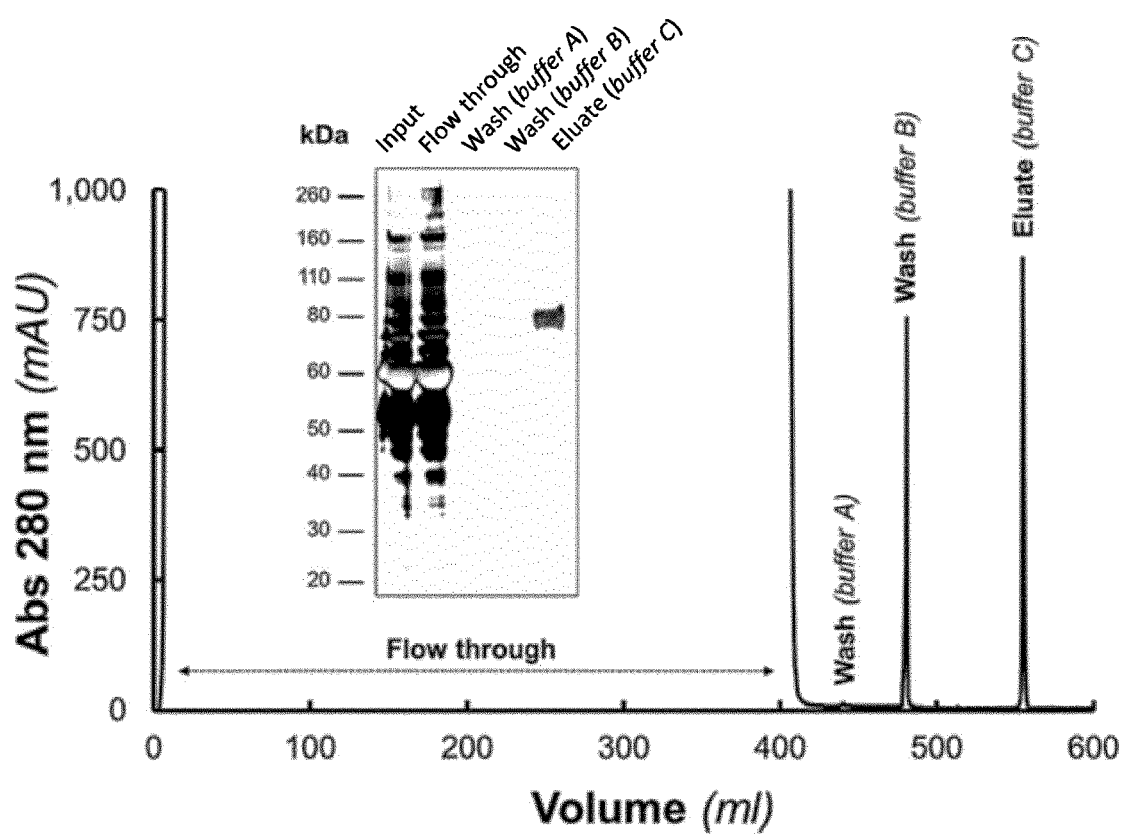

FIG. 9. IAC purification of recombinant human MSF. Chromatograms were recorded as UV absorbance at 280 nm. IAC fractions (input, flow through, wash, eluate) were run on 10% gels under denaturing and reducing conditions. A representative silver-stained gel is shown in the inset (13 µl/lane).

Figure 10:
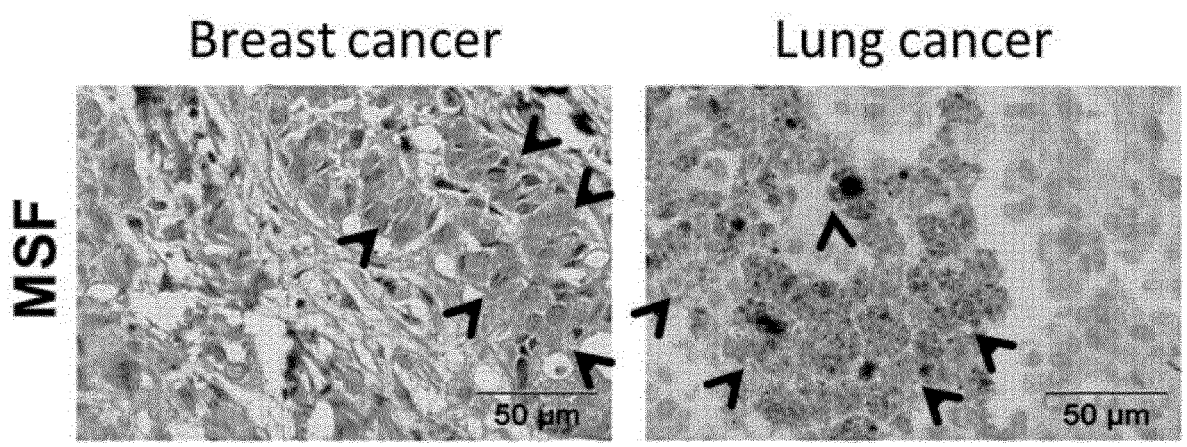

FIG. 10. Immunostaining of human cancer tissues with 1G5.3 antibody. Formalin-fixed paraffin-embedded sections of human breast and lung cancer tissues were stained with 1G5.3. Arrows indicate positive cells.

Figure 11:
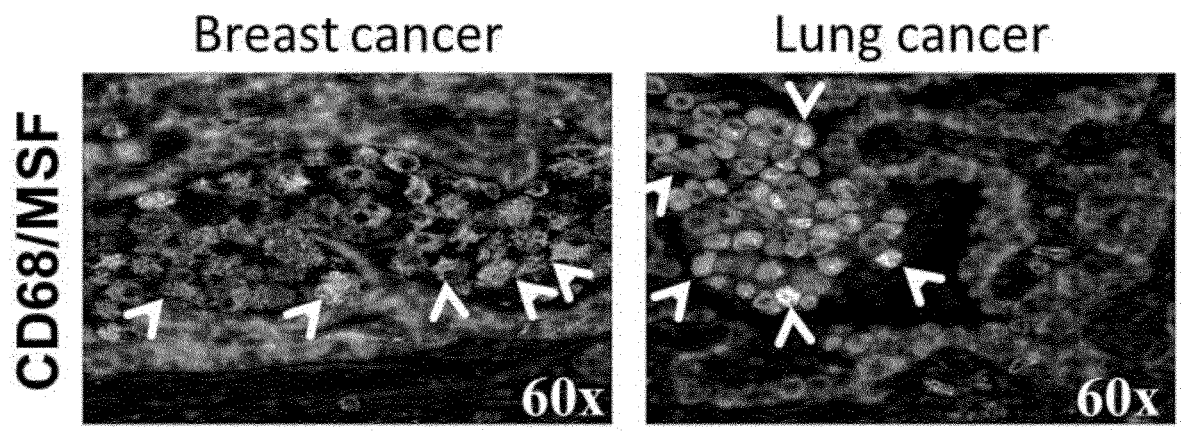

FIG. 11. Immunofluorescence staining of human cancer tissues. Tissue samples from breast and lung cancer were stained with CD68 and 1G5.3. Cells positive for the two markers are indicated by arrows.

Figure 12:
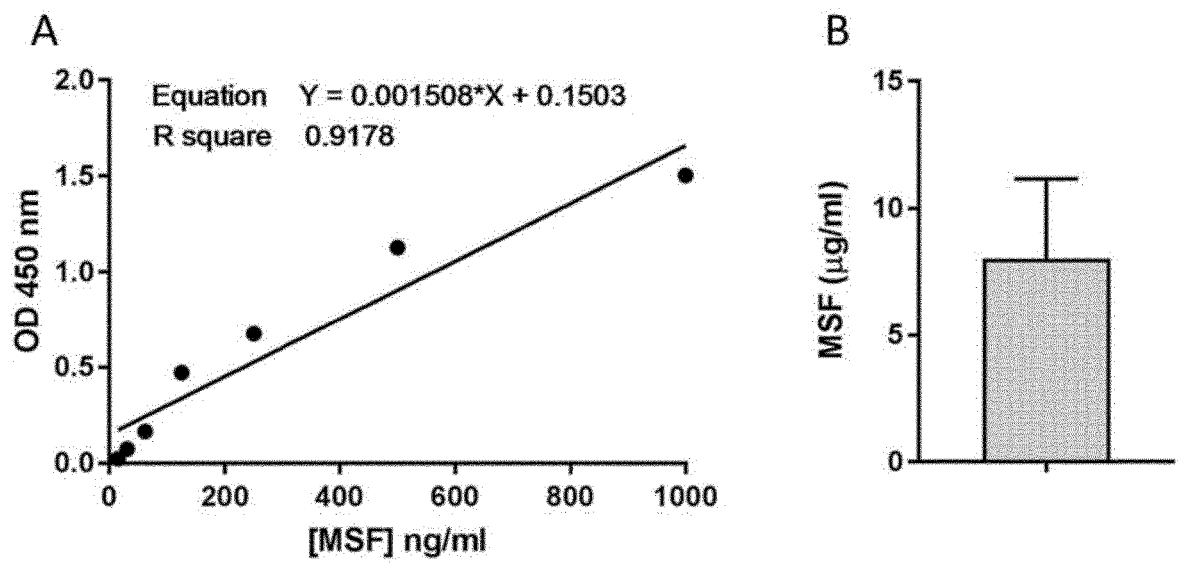

FIG. 12. Sandwich ELISA with 1G5.3 mAb. A) Standard curve performed with recombinant human MSF purified by immunoaffinity. B) MSF levels in supernatant from CHO-3E6 cells (8.0 µg/ml±3.1, mean±SEM, n=3).

Figure 13:
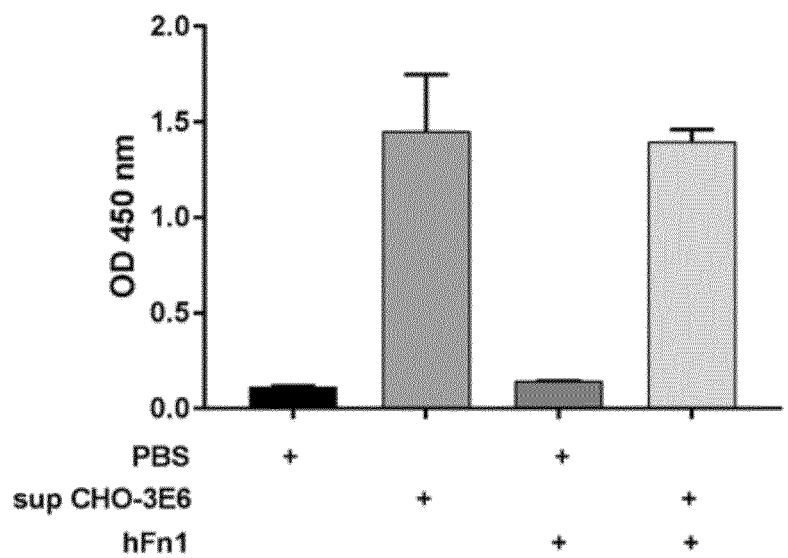

FIG. 13. Effect of a spike of hFn1 in the sandwich ELISA. 96-wells microtiter plates were coated with the 1G5.3 mAb, as described in FIG. 12. Buffer (PBS) or supernatant from CHO-3E6 was then added in the presence or in the absence of hFn1 (at 100 µg/ml), and bound MSF was revealed as described.

Figure 14:
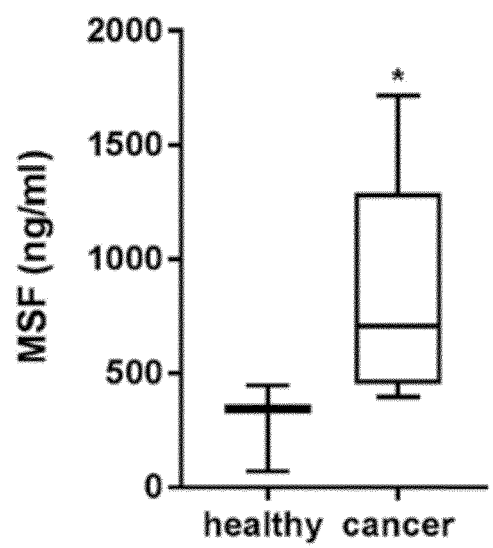

FIG. 14. MSF levels in human plasma. MSF levels in the blood of healthy individuals and cancer patients were measured with the sandwich ELISA based on 1G5.3 mAb. (*p=0.048, Mann Whitney test).

Figure 15:
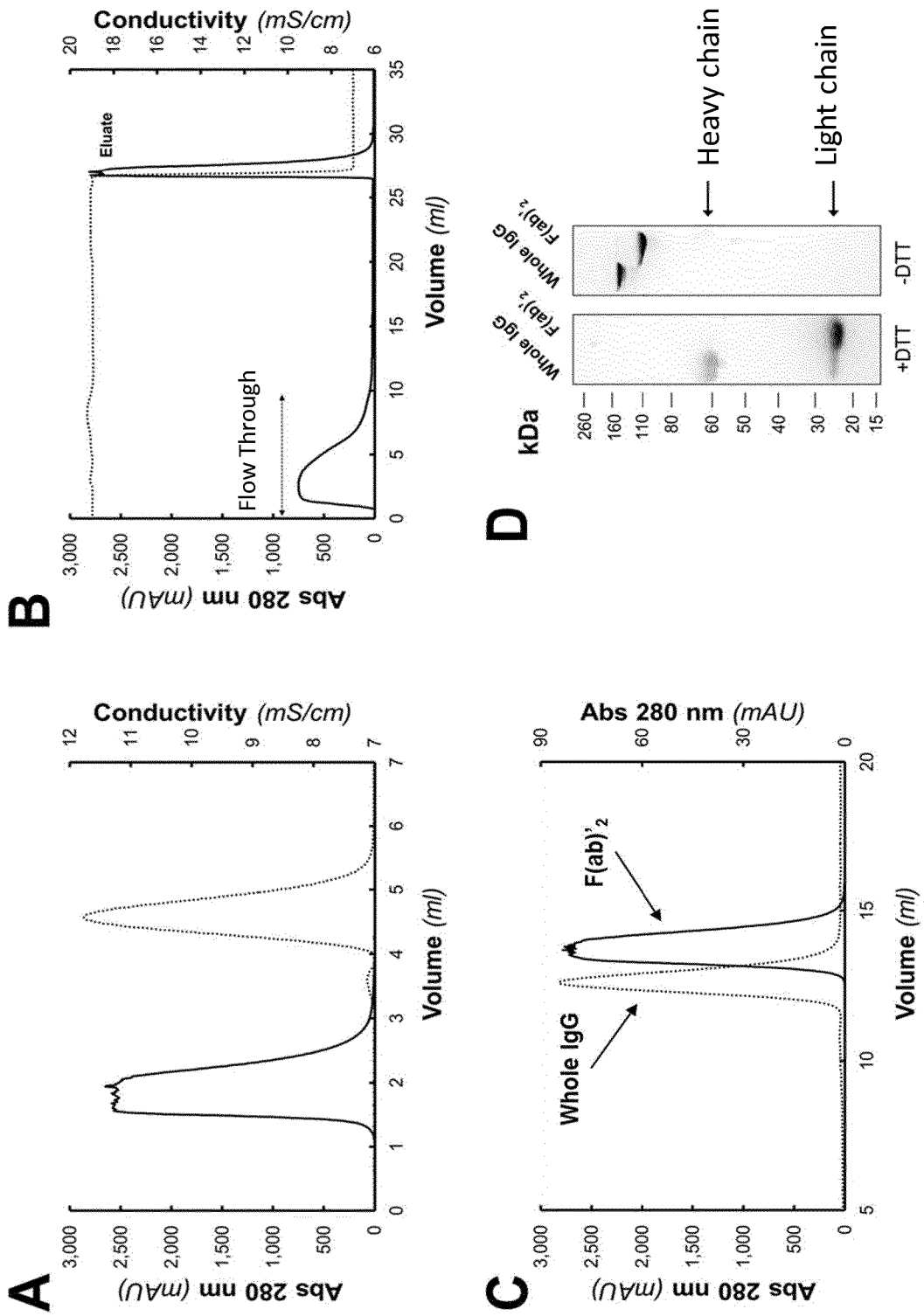

FIG. 15. Preparation and characterization of anti-human MSF 1G5.3 F(ab)'$_2$ fragment. A) The 1G5.3 antibody was concentrated on Vivaspin 6 10 kDa MWCO concentrators and buffer exchanged against 100 mM Sodium Citrate, pH 3.50 on a HiTrap Desalting 5 ml column prior to reaction with pepsin. Shown is an overlaid plot of UV absorbance at 280 nm (left axis and solid line, to monitor protein elution) and conductivity (right axis and dotted line, to monitor salt removal) from a representative SEC run. B) The buffer-exchanged material was incubated with pepsin then loaded onto an HiTrap MabSelect 1 ml column, equilibrated with PBS and eluted with 100 mM Sodium Citrate, pH 3.50. A typical chromatogram (UV absorbance at 280 nm, left axis and solid line; conductivity, right axis and dotted line) is reported. Unbound material (flow through), containing the Fc fragment, was discarded, and eluate, containing the F(ab)'2 fragment, was retained and subjected to further processing. C) Eluate from B was concentrated on Vivaspin 6 10 kDa MWCO concentrators and chromatographed on a Superdex 200 10/300 GL column equilibrated and eluted with PBS. Protein separation was monitored as UV absorbance at 280 nm (F(ab)'$_2$, left axis and solid line). A 100 µg aliquot of whole unprocessed 1G5.3 antibody was run under the same conditions (Whole IgG, right axis and dotted line). An overlay of chromatograms from both species is shown. D) Aliquots of whole 1G5.3 antibody and the corresponding F(ab)'2 fragments (from SEC in C) were separated on NuPAGE Novex Bis-Tris 10% gels under denaturing conditions in the presence and absence of dithiothreitol (+DTT and −DTT, respectively). Shown is a Coomassie-stained gel. Non-reduced whole 1G5.3 and F(ab)'$_2$ migrate at 150 and 110 kDa, respectively; under reducing conditions, 1G5.3 separates into two bands of 60 (heavy chain) and 25 (light chain) kDa, whereas F(ab)'2 gives a single band at 25 kDa. Data in A to D are representative of three independent experiments.

Figure 16:
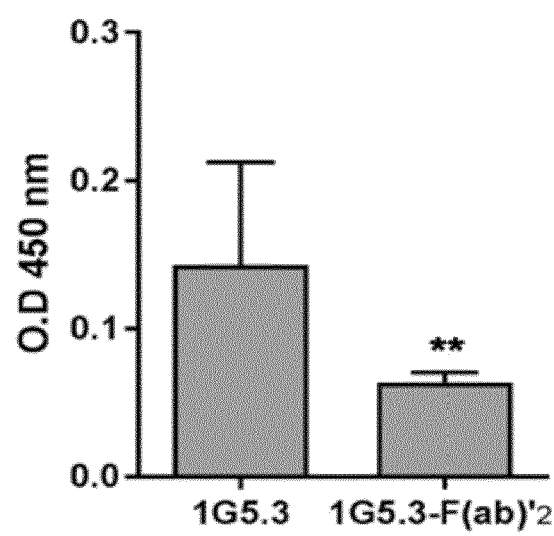

FIG. 16. Comparison of the background signal generated with the 1G5.3 mAb and the 1G5.3-F(ab)'2 fragment. Buffer was added to wells coated with 1G5.3 or 1G5.3-F(ab)'2 antibodies and developed as described in the text. (**p=0.022 Student's t test).

Figure 17:
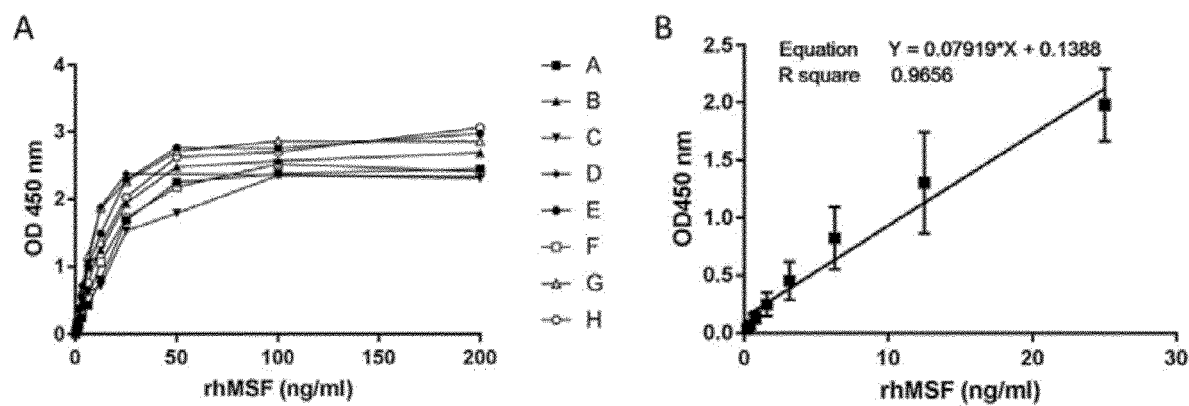

FIG. 17. Standard curves obtained with the 1G5.3-F(ab)'2 fragment in coating. A) 0.2-200 ng/ml of hrMSF were incubated on wells coated with 1G5.3-F(ab)'2. An overlay of eight standard curves from as many independent experiments is shown. B) Reported is a standard curve obtained from averaging the eight individual curves in panel A). Lower and upper limits of the dynamic linear range (suitable for MSF quantitation) are 0.4 and 25 ng/ml, respectively.

Figure 18:
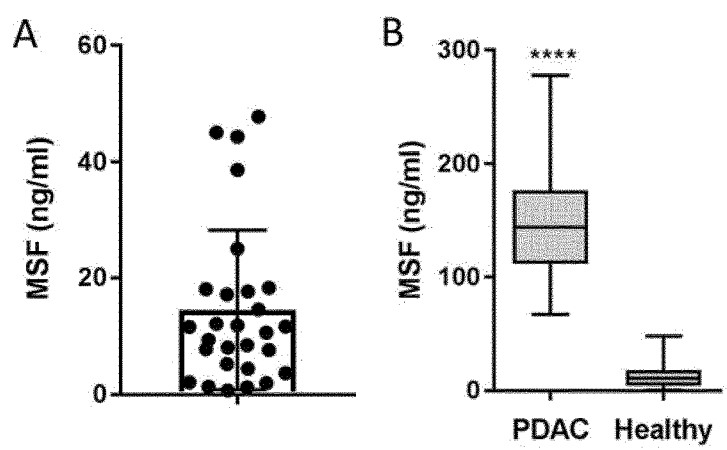

FIG. 18. MSF levels in healthy subjects and in patients with PDAC. MSF was measured by sandwich ELISA using 1G5.3-F(ab)'2 as a capturing antibody. A) Distribution of MSF levels in healthy subjects (n=28). B) comparison of MSF levels in patients with PDAC (n=33) as compared to those in healthy subjects. (****p<0.0001 Mann-Whitney test).

Figure 19:
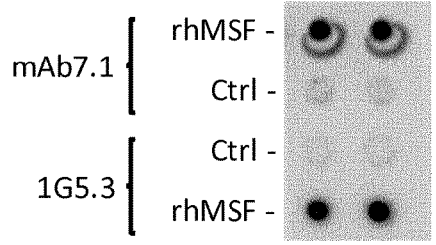

FIG. 19. Dot Blot analysis of the interaction with rhMSF of mAb7.1 and 1G5.3. Recombinant human MSF (rhMSF) was adsorbed onto nitrocellulose membranes (200 ng/well) using a Bio-Dot apparatus (Bio-Rad). Following blocking of uncoated sites, blots were probed with the conditioned medium from mAb7.1 hybridoma cultures (undiluted supernatant) or purified 1G5.3 monoclonal antibody (250 ng/ml). Empty wells (with no rhMSF) were taken as negative control (Ctrl). One blot is shown that is representative of two independent experiments.

Figure 20:
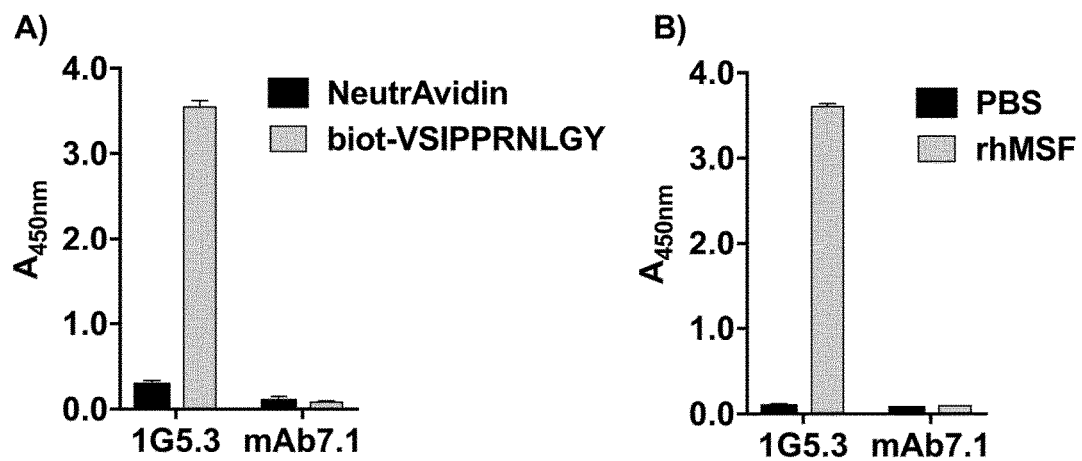

FIG. 20. Indirect ELISA analysis of the interaction of mAb7.1 and 1G5.3 with biot-VSIPPRNLGY and rhMSF. A) The biot-VSIPPRNLGY peptide (SEQ ID NO:11) (spanning the aa 648-657 sequence at the C-terminus of human MSF) was captured onto Maxisorb plates that had been coated with NeutrAvidin. Conditioned medium from mAb7.1 hybridoma cultures (undiluted) or purified 1G5.3 (10 ng/ml) were added, and bound antibodies were revealed with the appropriate HRP-conjugated secondary antibody, as described in Materials and Methods. B) Maxisorb plates were coated with rhMSF, and incubated with mAb7.1 hybridoma cultures or purified 1G5.3. Bound antibodies were revealed as described in A. Both in A and B results are expressed as absorbance at 450 nm (A450 nm, mean±SD). Wells containing NeutrAvidin (NeutrAvidin in A) or PBS−/− (PBS in B) only were taken as negative controls. Shown are plots from one out of two independent experiments, each performed in duplicate.

Figure 21:
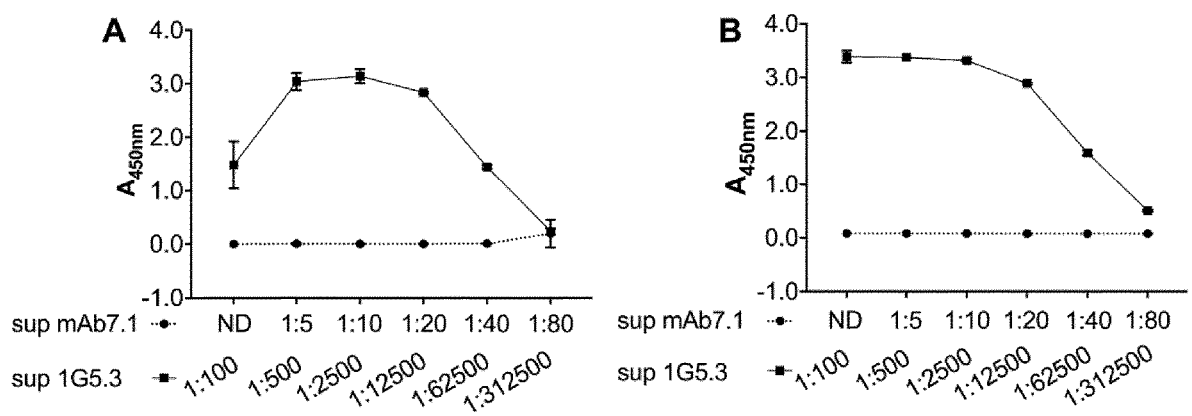

FIG. 21. Dose-dependency of the interaction of mAb7.1 and 1G5.3 with biot-VSIPPRNLGY (SEQ ID NO:11) and rhMSF. A) The biot-VSIPPRNLGY peptide (SEQ ID No:11) was captured onto Maxisorb plates that had been coated with NeutrAvidin as described in FIG. 20. Conditioned media from mAb7.1 or 1G5.3 hybridoma cell cultures were applied at the indicated dilutions. Bound antibodies were revealed with the appropriate HRP-conjugated secondary antibody, as described in Materials and Methods. B) Maxisorb plates were coated with rhMSF, and incubated with the conditioned medium from mAb7.1 or 1G5.3 hybridoma cell cultures at the indicated dilutions. Bound antibodies were revealed as described in A. Both in A and B results are expressed as absorbance at 450 nm (A450 nm, mean±SD), following subtraction of the background signal from empty wells (i.e., with NeutrAvidin or PBS−/− only). Shown are plots from one out of two independent experiments, each performed in duplicate.

EXAMPLE 1

Materials and Methods
Commercial Reagents and Cell Lines

Human Fibronectin 1 (hFn1) was from Calbiochem (Merck, Milan, Italy; Cat No: 341635). Fetal calf serum (FCS) with low endotoxin content was from Sigma Aldrich (Milan, Italy; Cat No: F7524); RPMI-1640, Dulbecco Modified Eagle's Medium (DMEM;) and trypsin used for cell culture were from LONZA (Euroclone, Milan, Italy; Cat No: BE12-167F; BE12-733F and BE17-161E respectively). Phosphate buffered saline (PBS) with calcium and magnesium (PBS+/+) was from Biosera (Biotecna, Milan, Italy; Cat No: XC-S2067), PBS without calcium and magnesium (PBS−/−Cat No: D8537) and geneticin (G418; Cat No: G8168) were from Sigma-Aldrich (Milan, Italy).

The synthetic peptide specific for human MSF (aa 648-657 of SEQ ID No: 4) was synthesized by PRIMM S.r.l. (Milan, Italy). A cysteine residue was added at the COOH-terminal of the ten amino acids long peptide (VSIPPRNLGYC [SEQ ID No: 9]). The peptide was conjugated to Keyhole limpet hemocyanin (KLH) (VSIPPRNLGYC-KLH) (SEQ ID NO:9).

A 105 amino acids long fragment of human MSF (His-MSF; from residue 553 to 657 of the C-terminal portion of MSF; mw 14.335 kDa, SEQ ID No: 10), including the specific MSF decapeptide VSIPPRNLGY (SEQ ID NO:11) at the C-terminus and a histidine tag at the N-terminus, has been obtained from PRIMM. The expression vector pSG5 (4,100 bp) was from Stratagene (La Jolla, Calif., USA);

pSV2neo, used to confer resistance to the selectable marker G418, was from ATCC (Manassas, Va., USA). Lipofectamine® 2000 (Invitrogen) was used to transfect CHO cells. CHO (Chinese hamster ovary) cells and SP2/0 myeloma cells were obtained from ATCC (Cat No ATCC CCL-61 and CRL 1581 respectively) and were cultured in Dulbecco Modified Eagle's Medium (DMEM) with L-Glutamine (Lonza, Cat No: BE17-605E/U1) and 10% (v/v) FCS.

Expression of Human Recombinant MSF

Recombinant human MSF (rhMSF) was expressed in CHO cells. The full length cDNA of human MSF (2,192 bp, accession n AJ535086.1, SEQ ID No: 3) was subcloned into the BamH1 site of a pSG5 vector (FIG. 2, pSG-MSF). The orientation of the cloned MSF was confirmed by sequencing. CHO cells were co-transfected with pSV2neo vector, conferring resistance to G418, using Lipofectamine® 2000 following the protocol indicated by the Manufacturer. Transfected clones were selected with 800 µg/ml G418 and analyzed for MSF production by indirect ELISA (see below) using a rabbit polyclonal antiserum produced in rabbits immunized with MSF decapeptide (see below). One of the positive clones was further subcloned by limiting dilution to obtain CHO-3E6 cells, producing high levels of human recombinant MSF.

Generation and Purification of Antibodies Against Human Recombinant MSF

Rabbit polyclonal antiserum (pAb) was generated immunizing rabbits with the synthetic 10 amino acids long peptide specific for human MSF wherein a cysteine was added at the COOH terminus (SEQ ID No: 9), conjugated to KLH as a carrier (VSIPPRNLGYC-KLH) (SEQ ID NO:9). Rabbits were challenged intraperitoneally (ip) with 300 µg of the MSF-specific peptide diluted in Complete Freund Adjuvant. Immunization was repeated at day 21, 28 and 35 with the peptide diluted in Incomplete Freund Adjuvant. Blood (40-50 ml/rabbit) from immunized rabbits was collected and tested by indirect ELISA against the immunogen (VSIPPRNLGYC-KLH) (SEQ ID NO:9) before the purification of specific antibodies by immunoaffinity on a CNBr-Sepharose column carrying the same immunogen.

Balb/c mice (BALB/cAnNCrl, Charles River, Calco, Italy) were immunized to obtain monoclonal antibodies against rhMSF. Briefly 200 µl of supernatant from CHO-3E6 cells expressing rhMSF were separated on 10% polyacrylamide gel under reducing and denaturing conditions in the discontinuous buffer system of Laemmli. The gel was stained with Colloidal Comassie (Bio-Safe™ Coomassie, Cat. No.: 161-0786, Bio-Rad) and the 70 kDa MSF band was excised and smashed in PBS. The suspension was used to immunize 8 weeks old male Balb/c mice. The procedure was repeated three times, three weeks apart. A fourth challenge was performed with purified His-MSF (20 µg/mice). Antibody titers were analyzed by indirect ELISA against His-MSF and Fn1, used as negative control (see below). Splenocytes from a responding mouse were fused with SP2/0 myeloma using polyethylene glycon 1550 (SERVA, Rome, Italy) following Manufacturer's standard procedures. Cells were seeded in 96 wells plates and selected using HAT medium (RPMI-1640 medium containing 10% FCS, 100 mg/mL streptomycin, 100 IU/mL penicillin, 100 mM hypoxanthine, 16 mM thymidine, and 400 mM aminopterin). After 2 weeks, culture supernatants were screened for antibody reactivity and specificity by indirect ELISA against the peptide and the supernatant of CHO-3E6 as source of human recombinant MSF. Cells from four different positive IgG producer wells were subcloned at 5 cells/well (two 96-wells plates for each clone). A second screening was performed by indirect ELISA against the MSF decapeptide and rhMSF contained in the supernatant of CHO-3E6 cells. Cells from two distinct IgG producer wells were further subcloned at 0.5 cells/well. The hybridomas obtained by this subclonig were tested by indirect ELISA against rhMSF contained in the supernatant of CHO-3E6 cells and Fn1. A total of 14 hybridomas were found able to recognize rhMSF contained in the culture supernatant of CHO-3E6 cells but not Fn1. Hybridoma 1G5.3 was selected for further development. The monoclonal antibody secreted from 1G5.3 hybridoma, identified from now on as 1G5.3, was purified from culture supernatant by Protein G-sepharose 4 Fast Flow column (GE Healthcare, Pittsburgh, Pa., Cat. No.: 17061801) following indications of the manufacturer. Briefly, a protein G-sepharose column (1 ml column volume) was equilibrated with PBS+/+ and loaded with culture supernatant diluted in the same buffer. The flow-through was applied again onto the column and the procedure was repeated 3 times. MSF-specific antibodies were then eluted using 0.1 M Glycine-HCl pH 2.8 and immediately buffered using 1.5 M Tris-HCl pH8.8. 1G5.3 isotype was determined using the Mouse Monoclonal Antibody Isotyping Test Kit (Bio-Rad, Cat.No.: MMT1). The type of light chain was determined by western blot using the rabbit mAb RM103 (Abcam, Cat. No.: 190484; anti-mouse Kappa light chain) and the rat mAb JC5-1 (Abcam, Cat. No.: 99622, anti-mouse lambda light chain).

Determination of 1G5.3 Sequence

Total RNA was isolated from the hybridoma cells following the technical manual of TRIzol® Reagent (Ambion. Cat. No.: 15596-026). Total RNA was then reverse-transcribed into cDNA using either isotype-specific anti-sense primers or universal primers following the technical manual of PrimeScript™ 1st Strand cDNA Synthesis Kit (Takara, Cat. No.: 6110A). Antibody fragments of VH, VL, CH and CL were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned and the consensus sequence was provided.

Preparation of F(Ab)'$_2$ Fragment

F(ab)'$_2$ fragment was generated from 1G5.3 [1G5.3-F(ab)'2] by enzymatic treatment. 8 ml (8 mg) aliquots of the 1G5.3 monoclonal antibody at 1 mg/ml in PBS (Sigma-Aldrich, Cat. No.: D1408), were concentrated to 1 ml on Vivaspin 6 PES 10 kDa MWCO concentrators (Sartorius Stedim, Goettingen, Germany, Cat. No.: VS0602), and buffer exchanged against 100 mM Sodium Citrate, pH 3.50 (Merck Millipore, Darmstadt, Germany, cat. N. 106448) on a HiTrap Desalting 5 ml column (GE Healthcare, Cat. No.: 17-1408-01) in two consecutive runs (500 µl/run). Protein-containing fractions (4 ml total volume) were pooled, and the antibody concentration was determined by UV absorbance at 280 nm using a value of 1.4 for the extinction coefficient of mouse IgG1 at 280 nm (expressed as absorbance of a 0.1% (w/v) solution at 280 nm).

To generate 1G5.3-F(ab)'$_2$ fragments, 5 µg pepsin (Sigma Aldrich, Cat. No.: P6887) were added per mg of antibody, and the resulting mixture was incubated at 37° C. for 16 h. The reaction was blocked adjusting the solution pH to 7.0 by addition of 650 µl 1M Tris-Cl, pH 8.80 (Merck Millipore, Cat. No.: 108382). The solution was then loaded onto an HiTrap MabSelect protein A 1 ml column (GE Healthcare), equilibrated with PBS and eluted with 100 mM Sodium Citrate, pH 3.50 at 1 ml/min. F(ab)'2-containing fractions were pooled (4 ml total volume) and concentrated to 600 µl on Vivaspin 6 PES 10 kDa MWCO concentrators. The concentrated material was chromatographed on a Superdex 200 10/300 GL column (GE Healthcare) equilibrated and eluted with PBS at 0.5 ml/min. Concentration of the F(ab)'2 fragments in the eluted fractions was measured as described above, and the SEC-purified material was stored at −20° C. until use. All chromatography runs were performed on a AKTA Purifier FPLC system (GE Healthcare); protein elution and salt separation were monitored as UV absorbance at 280 nm and conductivity (mS/cm), respectively. 3 µg aliquots of whole 1G5.3 antibody and the corresponding 1G5.3-F(ab)'2 fragments (from SEC) were separated on NuPAGE Novex Bis-Tris 10% gels (Thermo Fisher Scientific, Waltham, Mass.) under denaturing conditions in the presence and absence of dithiothreitol. Following electrophoresis, proteins were detected with the Bio-Safe Coomassie Stain (Bio-Rad, Hercules, Calif.).

Purification of Recombinant Human MSF

Recombinant human MSF was purified from the conditioned medium of CHO-3E6 by immunoaffinity chromatography (IAC). 400 ml of conditioned medium were loaded at 2.5 ml/min onto a 5 ml HiTrap NHS-activated HP column (GE Healthcare, Pittsburgh, Pa.) covalently coupled to 1G5.3 (2.8 mg 1G5.3/ml affinity medium), and equilibrated with buffer A (50 mM Tris-HCl, 150 mM NaCl, pH 7.00) on an AKTA Purifier FPLC system (GE Healthcare). The 1G5.3 column was extensively washed at 5 ml/min with buffer A followed by buffer B (50 mM Tris-HCl, 500 mM NaCl, pH 7.00), and bound rhMSF was eluted with buffer C (3.5 M MgCl2) in a total volume of 4 ml. Homogeneity of the eluted protein was assessed using an analytical Superdex 200 10/300 GL gel filtration column (GE Healthcare), equilibrated and eluted at 0.5 ml/min with buffer B on an AKTA Purifier FPLC system. In addition, aliquots of conditioned medium (input), unbound material (flow through) and eluted protein (eluate) from IAC were resolved on NuPAGE Novex Bis-Tris 10% gels (Thermo Fisher Scientific, Waltham, Mass.) under denaturing and reducing conditions (i.e., in the presence of dithiothreitol). Following electrophoresis, proteins were either revealed with the ProteoSilver Plus Silver Stain Kit (Sigma Aldrich, St. Louis, Mo.) and the Bio-Safe Coomassie Stain (Bio-Rad, Hercules, Calif.) or transferred to polyvinylidene difluoride (PVDF) membranes for subsequent immunodetection with either anti-human MSF or anti-hFn1 rabbit polyclonal antibodies, followed by anti-rabbit IgG horseradish peroxidase (HRP)-linked whole donkey antibody (GE Healthcare). Membranes were developed with Immobilon western HRP substrate (Merck Millipore, Darmstadt, Germany) and chemiluminescence recorded on a Chemidoc MP system (Bio-Rad). Throughout the purification process, total protein content was determined using a Bradford protein assay (Bio-Rad) and rhMSF specific titres were measured with an ELISA MSF assay made "in-house" as described below.

Immunohistochemical Analysis of on Human Tumour Sections.

Paraffin-embedded human tissue sections were cut and kept overnight at 37° C. Sections were dewaxed in Bioclear. Antigen unmasking was performed in a Decloaker Chamber in DIVA Buffer 1× (Biocare Medical Cat No: DV2004) for 3 minutes at 125° C. and 5 minutes at 90° C.

After blocking endogenous peroxidases with Peroxidized-1 (Biocare Medical Cat No: PX968) for 15 minutes, non-specific binding sites were blocked with Background Sniper solution (Biocare Medical Cat No: BS966) for 30 minutes. Human tissue samples were then incubated 1 h with 1G5.3 (1/150-1/300) to identify MSF, or with mouse monoclonal anti-human CD68 (Dako Cat No: M0876, clone PG-M1, 780 µg/ml for 1 h) to identify macrophages. Staining with CD68 does not require antigen unmasking. Immunostaining with 1G5.3 or with CD68 was revealed following incubation with rabbit anti-mouse MACH1 Polymer-HRP (Biocare Medical Cat No: MIU539) for 20 minutes. Then the reactions were developed with 3,3'-Diaminobenzidine tetrahydrochloride (Biocare Medical Cat No: DB801). Slides were counterstained for 3 min with haematoxylin solution.

Indirect ELISA

ELISA plates (Nunc Maxisorb immunoplates Cat. No.: 446612) were coated (O/N at 4° C.) with His-MSF (1-0.5 µg/well), supernatant from CHO-3E6 (50 µl) or hFn1 (1 µg/well), diluted in 15 mM Na carbonate buffer (pH9.6). After coating plates are washed three times with PBS+/+ and 0.05% Tween 20 (washing buffer), then non-specific interactions are blocked by incubation for 2 h at room temperature with 5% (w/v) dry milk in washing buffer. Wells were washed three times with washing buffer, then aliquots of rabbit polyclonal antiserum, supernatants from anti-MSF hybridomas or purified 1G5.3 diluted in washing buffer were added and incubated 1 h at room temperature. Anti-rabbit IgG or anti-mouse IgG labelled with horse-radish peroxidase (Cat No: GENA934 and GENA931 respectively, GE HEALTHCARE) were then added (1/2000 in washing buffer) and incubated 1 h at room temperature. Reaction was developed with 3,3',5,5'-tetramethylbenzidine (TMB; 1 Step™ ULTRA TMB-ELISA, Thermo Scientific, Rockford, Ill., USA; Cat No: 34019) and stopped with 2N $H_2SO_4$ before reading absorbance at 450 nm with an automated plate reader (Versamax microplate reader). Each sample was analyzed in triplicate and results are reported as mean OD450±SD or SEM, as indicated in figure legends. Baseline was obtained adding anti-MSF antibody on buffer-coated wells.

Sandwich ELISA

To measure MSF levels in biological fluids a sandwich ELISA has been developed. To this aim ELISA plates were incubated O/N at 4° C. with 250 ng/well of 1G5.3 or 500 ng/well of the 1G5.3-F(ab)'2 fragment diluted in PBS−/−, pH 7.0. After coating, plates were washed three times with 300 µl of washing buffer and then blocked with 5% dry milk for 2 h at 37° C. 100 µl of human plasma [informed consents were obtained] diluted 1/10 in washing buffer containing 2% Bovine Serum Albumin were then added and incubated for 1 h at room temperature. In the same plate a standard curve was generated using purified recombinant human MSF. After washing, plates were incubated with commercial biotinylated polyclonal Sheep IgG recognizing human hFn1 (0.25 µg/ml in washing buffer; R&D Cat No: BAF1918) for 1 h at room temperature. Finally, 100 µl of peroxidase-streptavidin (BioSpa Cat No: SB01-161) diluted 1/10000 in washing buffer were added and incubated 1 h at room temperature. Plates were then washed and incubated with 100 µl/well of the chromogenic substrate TMB before blocking with 2N H2SO4. Absorbance was read at 450 nm as described above. Linear regression was used to calculate MSF concentration in plasma samples from the standard curve made with recombinant MSF.

Results

This invention concerns the detection of human MSF as diagnostic and prognostic marker for M2 polarized macrophages involved in inflammatory pathologies such as asthma, allergies, and cancer. To this aim Inventors have developed the monoclonal antibody 1G5.3, recognizing specifically rhMSF. The antibody 1G5.3 can identify rhMSF by ELISA, can be used to purify rhMSF by immunoaffinity, and is effective in immunohistochemistry. Finally, and most important, 1G5.3 mAb has been efficiently used to develop a specific ELISA system for the measurement of human MSF levels in biological fluids. This assay is based on our particularly advantageous 1G5.3 antibody, antibody fragment or derivative thereof, which specifically recognize MSF, and on recombinant full length human MSF used as standard.

Production of Recombinant Human MSF

Recombinant human MSF was purified from the supernatant of CHO cells transfected with pSG-MSF. Approximately 300 clones derived from transfection of CHO cells with pSG-MSF and pSVneo were analyzed by indirect ELISA using initially a pAb developed immunizing rabbits with MSF specific peptide conjugated with KLH. Only six clones produced appreciable levels of rhMSF and were further subcloned by limiting dilution. FIG. 3 reports the results of an indirect ELISA showing the titration curve of supernatant collected from clone CHO-3E6, selected as source of the recombinant protein for further development.

Production and characterization of 1G5.3 mAb.

The monoclonal antibody 1G5.3 was developed immunizing mice with rhMSF, as detailed in the Material & Methods Section. The serum from immunized mice was analyzed by indirect ELISA using His-MSF as positive control and hFn1 as negative control. As shown in FIG. 4, the serum recognizes the 100 amino acids long fragment of human MSF (His-MSF), but not hFn1, at least in the experimental setting used herein.

The splenocytes from the responding mice were thus fused with SP2/0 myeloma and plated in 96-wells plates. A total of five plates were prepared. After two weeks, the fusion was tested by indirect ELISA: 100 µl of supernatant from each well of the five 96-wells plates were dispensed in wells of plates previously coated with the supernatant from CHO-3E6 cells as source of recombinant MSF or with the specific MSF decapeptide. FIG. 5 reports the results of one of the plates analyzed. From this primary screening Inventors selected four wells (G5 and B8 from plate 1 and A5 and D7 from plate 5) that were subcloned at 5 cells/well (2 plates for each clone). A secondary screening was performed with the supernatants from these plates by indirect ELISA on the peptide and on the supernatant from CHO-3E6 cells as source of recombinant MSF. FIG. 6 reports the screening of the two plates derived from clone G5. From this screening Inventors selected two clones, F7 from plate 1 and B8 from plate 2, both subcloned at 0.5 cells/well. Ten plates were obtained and supernatants were tested on microtiter plates coated with the peptide or supernatant from CHO-3E6 cells as source of rhMSF. From this analysis Inventors selected fourteen clones named 1G5.1, 1G5.2, 1G5.3 etc up to 1G5.14. The clones were grown in 6 wells plates and tested again for the capacity to recognize MSF in the supernatant of CHO-3E6 transfected cells and hFn1. As shown in FIG. 7, none of the clones was able to recognize hFn1 while they can recognize with different efficiencies MSF. Clone 1G5.3 was selected for further development.

mAb 1G5.3 was purified from culture supernatant of hybridoma cells by affinity chromatography on Protein-G sepharose. The hybridoma 1G5.3 expresses secreted antibodies of the subtype IgG1 heavy chain and kappa light chain. The purified antibody was finally analyzed in ELISA.

FIG. 8 reports the results of a titration curve of the purified monoclonal antibody 1G5.3 on plates coated with rhMSF or hFn1 (both at 500 ng/well). The results confirmed that mAb 1G5.3 does not recognize human hFn1.

DNA and Protein Sequences of 1G5.3

The DNA sequences of the heavy and light chains of 1G5.3 were obtained after subclonig of the two chains. The DNA sequence of Murine Heavy Chain of 1G5.3 is shown in SEQ ID No. 5 and the protein sequence is shown in SEQ ID No 6. The DNA sequence of the light chain of 1G5.3 is reported in SEQ ID No 7 while the protein sequence is shown in SEQ ID No 8.

Use of mAb 1G5.3 for the Purification of rhMSF rhMSF secreted in the culture supernatant by CHO-3E6 cells can be efficiently purified by Immuno-Affinity Chromatography (IAC). Conditioned media (input) from CHO-E6 cells was passed through an 1G5.3 column equilibrated and eluted as described in "Materials and Methods". Typical results of a purification session are shown in FIG. 9.

Use of mAb 1G5.3 in Immunohistochemistry

1G5.3 is effective in immunohistochemistry, recognizing MSF in human cancer tissues, as shown in FIG. 10. The protein is expressed by cancer cells as well as stromal cells in breast cancer tissues and by alveolar macrophages, as judged by morphology, in lung cancer tissues. Double immunofluorescence staining using the macrophage marker CD68 confirmed the expression by alveolar macrophages in lung cancer tissues and by a portion of macrophages in breast cancer specimens (FIG. 11)

Use of mAb 1G5.3 to Develop an Immunoassay for Measurement of MSF Levels in Biological Fluids To develop an immunoassay for the measurement of MSF levels in biological fluids Inventors tested 1G5.3 as capturing antibody. To generate the standard curve, 250 ng/well of mAb 1G5.3, diluted in carbonate buffer, were coated on plastic wells of ELISA microtiter plates. After blocking of non-specific sites, serial dilutions of rhMSF (range of concentrations from 1.5 to 1000 ng/ml) were dispensed in duplicate wells. Negative control is represented by wells coated with buffer alone. ELISA was performed as detailed in Material & Methods Section, and at the end of the procedure bound MSF was revealed by incubation with a commercial Sheep antiserum directed against hFn1. FIG. 12A reports a typical standard curve obtained following this procedure. Initially Inventors used this assay to measure MSF levels in the culture supernatant from CHO-3E6 cells. As shown in FIG. 12B, MSF concentration in supernatant from CHO-3E6 is approximately $8.0 \pm 3.1$ µg/ml (mean±SEM; three different lots of supernatant)

To confirm that, despite the use of an anti-hFn1 as detection antibody, the ELISA specifically recognize human MSF, up to 100 µg/ml of purified hFn1 were added in the assay. As shown in FIG. 13, hFn1 is not revealed in the sandwich ELISA developed and addition of hFn1 does not affect recognition of human MSF. This result confirmed the specificity of 1G5.3 in the recognition and capturing of human MSF but not hFn1. Inventors next tested this ELISA assay to evaluate MSF content in plasma samples from healthy subjects and cancer patients (informed consents were obtained). FIG. 14 reports the results obtained with the sandwich ELISA developed. MSF is measurable in plasma from healthy subjects as well as from cancer patients. In addition, as patients in FIG. 14, patients with cancer have higher levels of MSF compared to healthy subjects ($p=0.048$, Mann Whitney test).

Production of 1G5.3-F(Ab)'2 Fragment

The sandwich ELISA based on the use of our mAb 1G5.3 resulted to be effective in the measurement of MSF levels both in culture supernatants and in plasma samples. To increase the specificity of the ELISA, Inventors also tested the 1G5.3-F(ab)'2 obtained following treatment of the purified antibody with pepsin. To this aim, 1G5.3 antibody was concentrated on Vivaspin 6 concentrators (10 kDa MWCO) and buffer exchanged against 100 mM Sodium Citrate, pH 3.50 on a HiTrap Desalting 5 ml column prior to reaction with pepsin. FIG. 15A shows a typical profile after SEC separation of the protein before treatment with pepsin. The buffer-exchanged material was incubated with pepsin (37° C. for 14 h) and then loaded onto a HiTrap MabSelect column to separate Fc fragments, recovered in the unbound material (flow through), from F(ab)'2 fragments, eluted from the column with 100 mM Sodium Citrate (FIG. 15B). The F(ab)'2 fragments eluted from the column were subsequently concentrated on Vivaspin 6 and chromatographed on a Superdex 200 10/300 GL column equilibrated and eluted with PBS (FIG. 16C). A 100 μg aliquot of whole unprocessed 1G5.3 antibody was run under the same conditions (Whole IgG, right axis and dotted line, FIG. 15C). Aliquots of whole 1G5.3 antibody and the corresponding F(ab)'2 fragments (from SEC in C) were separated on NuPAGE Novex Bis-Tris 10% gels under denaturing conditions in the presence and absence of dithiothreitol (+DTT and −DTT, respectively). A representative gel stained with Coomassie is reported in FIG. 15D. Non-reduced 1G5.3 and 1G5.3-F(ab)'2 migrate at 150 and 110 kDa, respectively; under reducing conditions, 1G5.3 separates into two bands of 60 (heavy chain) and 25 (light chain) kDa, whereas 1G5.3-F(ab)'2 gives a single band at 25 kDa.

Use of 1G5.3-F(Ab)'2 Fragment to Develop an Immunoassay for Measurement of MSF Levels in Biological Fluids The 1G5.3-F(ab)'2 fragment was then tested in the sandwich ELISA following the same procedure outlined above. Inventors compared initially the background obtained with the two different antibodies coated on plastic wells. As shown in FIG. 16, using the 1G5.3-F(ab)'2 in coating resulted in a significant reduction of the background (p=0.022; Student's t test). This is particularly important to increase the lower limit of detection of the assay. To define the optimal range of concentrations of rhMSF for the standard curve, different amounts of protein (from 0.2 to 200 ng/ml) were incubated on 1G5.3-F(ab)'2 coated plates. The optimal range of concentrations for the standard curve with rhMSF resulted to be between 0.4 to 25 ng/ml, this resulting in an improvement of the sensitivity of the assay compared to the setting based on the 1G5.3 mAb (lower limit of detection was 1.5 ng/ml). FIG. 17A show the reproducibility of the standard curves obtained while FIG. 17B shows the mean standard curve generated. Inventors then measured MSF levels in a series of plasma collected from healthy donors and from patients with pancreatic ductal adenocarcinoma (PDAC) [informed consents have been obtained]. Healthy donors have a median MSF level of 11.11 ng/ml (Q1-Q3: 4.64-17.97; n=28; FIG. 18A) In PDAC patients median MSF levels are 143.7 ng/ml (Q1-Q3: 111,6-176,8; n=33; FIG. 18B), and are statistically different from levels in healthy subjects (p<0.0001 Mann-Whitney test). Overall the data illustrated herein suggest that 1G5.3 is a specific monoclonal antibody recognizing MSF, a molecule associated to M2 polarized macrophages. The antibody and its derivatives can efficiently quantify MSF levels in biological fluids from individuals with pathological conditions associated to M2 polarization of macrophages.

Clinical Applications

The monoclonal antibody developed can be used to identify M2 polarized macrophages, involved in different inflammatory pathologies, and M2-like tumor associated macrophages. In addition, the antibody will allow to develop an assay to evaluate circulating levels of the protein. The analysis of MSF expression can have a diagnostic and prognostic value in cancer patients as well as in other

EXAMPLE 2

Materials and Methods
Proteins and Peptides rhMSF was expressed in and purified from a CHO cell clone as described in example 1. A synthetic peptide specific for human MSF was synthetized by PRIMM S.r.l. (Milan, Italy) that contained a biotin moiety linked to the N-terminus via an aminohexanoic (Ahx) arm (biot-VSIPPRNLGY [biot-Ahx-VSIPPRNLGY] (SEQ ID NO: 11), aa 648-657).

Commercial Reagents

Fetal calf serum (FCS) with low endotoxin content was from Sigma Aldrich (Milan, Italy; Cat No: F7524); Dulbecco Modified Eagle's Medium (DMEM;) was from LONZA (Euroclone, Milan, Italy; Cat No: BE12-733F). Phosphate buffered saline (PBS) with calcium and magnesium (PBS+/+) was from Biosera (Biotecna, Milan, Italy; Cat No: XC-S2067), PBS without calcium and magnesium (PBS−/− Cat No: D8537) was from Sigma-Aldrich (Milan, Italy). All other Chemicals were from Sigma-Aldrich and of the highest purity available.

mAb7.1 Hybridoma Cultures

Cells were grown in DMEM containing 10% FCS. Conditioned media (supernatants) containing the secreted antibody were collected from approximately $6-8 \times 10^5$ cells/ml cultures and centrifuged at 2,000 rpm to remove cellular debris prior to Dot Blot and ELISA analysis. Ability of mAb7.1 to recognize rhMSF purified from CHO-3E6 cells or biot-VSIPPRNLGY (SEQ ID NO:11) peptide was assessed by indirect ELISA and Dot Blot analysis. In the same set of experiments supernatant from 1G5.3 hybridoma or purified 1G5.3 mAb were used for comparison.

Indirect ELISA on rhMSF

ELISA plates (Nunc Maxisorb immunoplates Cat. No.: 446612) were coated (O/N at 4° C.) with rhMSF (200 ng/well in 15 mM Na carbonate buffer, pH 9.60). Plates were then washed three times with PBS+/+ containing 0.05% (v/v) Tween 20 (washing buffer), and uncoated sites were blocked by incubation for 2 h at room temperature with 5% (w/v) dry milk in washing buffer. Wells were washed three times with washing buffer, then 100 μl aliquots of supernatants from the mAb7.1 hybridoma (either undiluted or diluted in washing buffer as indicated) or 1G5.3 hybridoma cultures (diluted in washing buffer as indicated), or purified 1G5.3 antibody (diluted in washing buffer; 10 ng/well) were added. Following 1 h incubation at room temperature and additional washing, 100 μl/well anti-mouse IgG antibody conjugated with horse-radish peroxidase (GE Healthcare, Pittsburgh, Pa., Cat. No.: GENA931) were added (1:2,000 dilution in washing buffer), and further incubation was allowed for 1 h at room temperature. After washing, bound antibodies were revealed by addition of 3,3'',5,5'-tetramethylbenzidine (TMB; 1 Step™ ULTRA TMB-ELISA, Thermo Scientific, Rockford, Ill., USA; Cat No: 34019), followed by 2N H2SO4. Plates were read on a VersaMax spectrophotometer (Molecular Devices, Sunnyvale, Calif.) and results were expressed as absorbance at 450 nm (A450 nm). Background absorbance from empty wells (i.e., without MSF)

was subtracted at each applied antibody dilution. Each sample was analyzed in duplicate and results were reported as mean±SD or SEM, as indicated in figure legends Indirect ELISA on the Biot-VSIPPRNLGY (SEQ ID NO:11) Peptide Nunc Maxisorb immunoplates were coated (O/N at 4° C.) with NeutrAvidin protein (1 µg/well; Thermo Scientific, Rockford, Ill., USA; Cat No: 31000) in PBS−/−. Biot-VSIPPRNLGY (SEQ ID NO:11) peptide (100 µl/well, 10 µg/ml in PBS+/+ containing 0.05% (v/v) Tween 20, washing buffer) was added and captured on the NeutrAvidin layer for 1 h at room temperature; this allowed N→C orientation of the peptide, thus mimicking its topological organization in the context of the MSF protein [19]. Uncoated sites were blocked by incubation for 2 h at room temperature with 2% (w/v) bovine serum albumin (BSA, Sigma Aldrich; Cat No: A7030) in PBS+/+. Wells were washed three times with washing buffer, then 50 µl aliquots of supernatants from the mAb7.1 hybridoma (either undiluted or diluted in washing buffer as indicated) or 1G5.3 hybridoma cultures (diluted in washing buffer as indicated), or purified 1G5.3 antibody (diluted in washing buffer, 10 ng/well) were added. Bound antibodies were revealed as described above, and results were expressed as absorbance at 450 nm (A450 nm). Each sample was analyzed in duplicate and results were reported as mean±SD.

Dot Blot Analysis

In addition to ELISA, the interaction with rhMSF of both 1G5.3 and mAb7.1 antibodies was assessed by Dot Blot, using a Bio-Dot apparatus (Bio-Rad, Hercules, Calif., USA; Cat No: 1620115) operated by a vacuum manifold according to the manufacturer's instructions. 100 µl aliquots of rhMSF (200 ng/well) in 15 mM Na carbonate buffer, pH 9.60 were passed through a 0.45 µm nitrocellulose membrane that had been pre-wetted with 100 µl/well 20 mM Tris-HCl, 500 mM NaCl, pH 7.50 (TBS). Uncoated sites were blocked by incubation for 1 h at room temperature with 2% (w/v) BSA in TBS (TBS-BSA). Wells were washed three times with 200 µl/well TBS containing 0.05% (v/v) Tween 20 (TBS-T), then 100 µl/well supernatants from the mAb7.1 hybridoma cultures (diluted 1:2 with TBS-BSA) or purified 1G5.3 antibody (250 ng/ml in TBS-BSA) were added. Following 30 min incubation at room temperature and additional washing, 100 µl/well anti-mouse IgG antibody conjugated with horse-radish peroxidase were added (1:3,000 dilution in TBS-BSA), and further incubation was allowed for 30 min at room temperature. After washing, bound antibodies were revealed using the Pierce™ ECL Western Blotting Substrate (Thermo Scientific; Cat. No.: 32106) and chemiluminescence was recorded on a ChemiDoc MP system (Bio-Rad). Acquired images were analyzed with the Image-Lab software (Bio-Rad).

Results

In initial experiments, inventors assessed recognition of the recombinant human MSF (rhMSF) by mAb7.1 (in the conditioned medium from cultures of the hybridoma cell clone that makes the antibody) and purified 1G5.3 in a Dot Blot setting. As shown in FIG. 19, both antibodies recognized the absorbed protein with low non-specific binding to empty wells. This is consistent with previous reports on the application of mAb7.1 in Dot Blot experiments [21, 24, 19]. Furthermore, these findings indicate that the 1G5.3 antibody is suitable for Dot Blot analyses. Inventors then extended comparative investigations to indirect ELISA, using Maxisorb plates that had been coated either with the biot-VSIPPRNLGY (SEQ ID NO:11) peptide (as a way to assess epitope binding) or rhMSF. As indicated in FIG. 20, purified 1G5.3 bound both biot-VSIPPRNLGY (SEQ ID NO:11) peptide and rhMSF, however mAb7.1 failed to recognize the unique MSF decapeptide and the intact protein (rhMSF) (FIGS. 20A and B, respectively). It is worth noting here that an as low concentration as 10 ng/ml was used for the purified 1G5.3 in these experiments, to rule out sensitivity issues. To further address this point inventors compared in the same setting serial dilutions of the conditioned media from 1G5.3 and mAb7.1 hybridomas that had been collected from cultures with similar cell counts and viabilities. As shown in FIG. 21, the supernatant from the 1G3.5 hybridoma proved effective at recognizing both the biot-VSIPPRNLGY peptide (SEQ ID NO:11) (panel A) and the recombinant MSF protein (panel B). In sharp contrast to this, the supernatant from the mAb7.1 hybridoma could not recognize either molecule, despite of it being applied at vastly smaller dilutions (i.e., higher concentrations) than that from 1G5.3.

CONCLUSIONS

It has been previously reported that mAb7.1 recognizes rhMSF in a Dot Blot setting [19, 24], however no data are available on applications of this antibody in ELISA. In addition, based on available evidence, use of this antibody is limited to Immunohystochemistry procedures [19, 23, 20]. Inventors herein observed that mAb7.1 bound rhMSF in Dot Blot experiments but failed to recognize the biot-VSIPPRNLGY peptide (i.e., the C-terminal unique tail of MSF, SEQ ID NO:11) and rhMSF when these were absorbed onto the plastic wells of Maxisorb plates, under typical ELISA conditions. Most importantly, the 1G5.3 antibody (both in a conditioned medium and as a purified molecule) recognized biot-VSIPPRNLGY (SEQ ID NO:11) peptide and rhMSF in a dose-depending fashion. In addition, the purified 1G5.3 specifically detected rhMSF in Dot Blot experiments, which extends the range of applications of this antibody to Dot Blot. These results indicate that mAb7.1 is not suitable for ELISA applications, and the 1G5.3 antibody is unique in its ability to recognize MSF in different experimental settings, most importantly in ELISA immunoassays designed to measure the MSF levels in biological fluids pathological conditions.

SEQUENCES

```
SEQ ID No: 1: mRNA for Fibronectin 1 [Homo sapiens], complete cds (7753 bp); GenBank
accession No AB191261.1
   1 gcccgcgccg gctgtgctgc acaggggag gagagggaac cccaggcgcg agcgggaaga 61 ggggacctgc agccacaact tctctggtcc tctgcatccc ttctgtccct ccacccgtcc 121 ccttcccac cctctggccc ccaccttctt ggaggcgaca accccggga ggcattagaa 181 gggatttttc ccgcaggttg cgaagggaag caaacttggt ggcaacttgc ctcccggtgc
```

-continued

```
 241 gggcgtctct cccccaccgt ctcaacatgc ttaggggtcc ggggcccggg ctgctgctgc 301 tggccgtcca gtgcctgggg acagcggtgc cctccacggg agcctcgaag agcaagaggc 361 aggctcagca aatggttcag ccccagtccc cggtggctgt cagtcaaagc aagcccggtt 421 gttatgacaa tggaaaacac tatcagataa atcaacagtg ggagcggacc tacctaggca 481 atgcgttggt ttgtacttgt tatggaggaa gccgaggttt aactgcgag agtaaacctg 541 aagctgaaga gacttgcttt gacaagtaca ctgggaacac ttaccgagtg ggtgacactt 601 atgagcgtcc taaagactcc atgatctggg actgtacctg catcgggct gggcgaggga 661 gaataagctg taccatcgca aaccgctgcc atgaaggggg tcagtcctac aagattggtg 721 acacctggag gagaccacat gagactggtg gttacatgtt agagtgtgtg tgtcttggta 781 atggaaaagg agaatggacc tgcaagccca tagctgagaa gtgttttgat catgctgctg 841 ggacttccta tgtggtcgga gaaacgtggg agaagcccta ccaaggctgg atgatggtag 901 attgtacttg cctgggagaa ggcagcggac gcatcacttg cacttctaga aatagatgca 961 acgatcagga cacaaggaca tcctatagaa ttggagacac ctggagcaag aaggataatc 1021 gaggaaacct gctccagtgc atctgcacag gcaacggccg aggagagtgg aagtgtgaga 1081 ggcacacctc tgtgcagacc acatcgagcg gatctggccc cttcaccgat gttcgtgcag 1141 ctgtttacca accgcagcct cacccccagc ctcctccta tggccactgt gtcacagaca 1201 gtggtgtggt ctactctgtg gggatgcagt ggctgaagac acaaggaaat aagcaaatgc 1261 tttgcacgtg cctgggcaac ggagtcagct gccaagagac agctgtaacc cagacttacg 1321 gtggcaactc aaatggagag ccatgtgtct taccattcac ctacaatggc aggacgttct 1381 actcctgcac cacagaaggg cgacaggacg gacatctttg gtgcagcaca acttcgaatt 1441 atgagcagga ccagaaatac tctttctgca cagaccacac tgttttggtt cagactcgag 1501 gaggaaattc caatggtgcc ttgtgccact tcccttcct atacaacaac cacaattaca 1561 ctgattgcac ttctgagggc agaagagaca acatgaagtg gtgtgggacc acacagaact 1621 atgatgccga ccagaagttt gggttctgcc ccatggctgc ccacgaggaa atctgcacaa 1681 ccaatgaagg ggtcatgtac cgcattggag atcagtggga taagcagcat gacatgggtc 1741 acatgatgag gtgcacgtgt gttgggaatg gtcgtgggga atggacatgc attgcctact 1801 cgcagcttcg agatcagtgc attgttgatg acatcactta caatgtgaac gacacattcc 1861 acaagcgtca tgaagagggg cacatgctga actgtacatg cttcggtcag ggtcggggca 1921 ggtggaagtg tgatcccgtc gaccaatgcc aggattcaga gactgggacg tttttatcaaa 1981 ttggagattc atgggagaag tatgtgcatg gtgtcagata ccagtgctac tgctatggcc 2041 gtggcattgg ggagtggcat tgccaacctt tacagaccta ccaagctca gtggtcctg 2101 tcgaagtatt tatcactgag actccgagtc agcccaactc ccacccatc cagtggaatg 2161 caccacagcc atctcacatt tccaagtaca ttctcaggtg agacctaaa aattctgtag 2221 gccgttggaa ggaagctacc ataccaggcc acttaaactc ctacaccatc aaaggcctga 2281 agcctggtgt ggtatacgag ggccagctca tcagcatcca gcagtacggc accaagaag 2341 tgactcgctt tgacttcacc accaccagca ccagcacacc tgtgaccagc aacaccgtga 2401 caggagagac gactcccttt tctcctcttg tggccacttc tgaatctgtg accgaaatca 2461 cagccagtag ctttgtggtc tcctgggtct cagcttccga caccgtgtcg ggattccggg 2521 tggaatatga gctgagtgag gagggagatg agccacagta cctggatctt ccaagcacag 2581 ccacttctgt gaacatccct gacctgcttc ctggccgaaa atacattgta aatgtctatc 2641 agatatctga ggatgggag cagagtttga tcctgtctac ttcacaaaca acagcgcctg
```

```
2701  atgcccctcc tgacccgact gtggaccaag ttgatgacac ctcaattgtt gttcgctgga
2761  gcagacccca ggctcccatc acagggtaca gaatagtcta ttcgccatca gtagaaggta
2821  gcagcacaga actcaacctt cctgaaactg caaactccgt caccctcagt gacttgcaac
2881  ctggtgttca gtataacatc actatctatg ctgtggaaga aaatcaagaa agtacacctg
2941  ttgtcattca acaagaaacc actggcaccc cacgctcaga tacagtgccc tctcccaggg
3001  acctgcagtt tgtggaagtg acagacgtga aggtcaccat catgtggaca ccgcctgaga
3061  gtgcagtgac cggctaccgt gtggatgtga tccccgtcaa cctgcctggc gagcacgggc
3121  agaggctgcc catcagcagg aacacctttg cagaagtcac cgggctgtcc cctgggtca
3181  cctattactt caaagtcttt gcagtgagcc atgggaggga gcaagcct ctgactgctc
3241  aacagacaac caaactggat gctcccacta acctccagtt tgtcaatgaa actgattcta
3301  ctgtcctggt gagatggact ccacctcggg cccagataac aggataccga ctgaccgtgg
3361  gccttacccg aagaggccag cccaggcagt acaatgtggg tccctctgtc tccaagtacc
3421  ccctgaggaa tctgcagcct gcatctgagt acaccgtatc cctcgtggcc ataaagggca
3481  accaagagag ccccaaagcc actggagtct ttaccacact gcagcctggg agctctattc
3541  caccttacaa caccgaggtg actgagacca ccattgtgat cacatggacg cctgctccaa
3601  gaattggttt taagctgggt gtacgaccaa gccaggagg agaggcacca cgagaagtga
3661  cttcagactc aggaagcatc gttgtgtccg gcttgactcc aggagtagaa tacgtctaca
3721  ccatccaagt cctgagagat ggacaggaaa gagatgcgcc aattgtaaac aaagtggtga
3781  caccattgtc tccaccaaca aacttgcatc tggaggcaaa ccctgacact ggagtgctca
3841  cagtctcctg ggagaggagc accacccccag acattactgg ttatagaatt accacaaccc
3901  ctacaaacgg ccagcaggga aattctttgg aagaagtggt ccatgctgat cagagctcct
3961  gcacttttga taacctgagt cccggcctgg agtacaatgt cagtgtttac actgtcaagg
4021  atgacaagga aagtgtccct atctctgata ccatcatccc agctgttcct cctcccactg
4081  acctgcgatt caccaacatt ggtccagaca ccatgcgtgt cacctgggct ccacccccat
4141  ccattgattt aaccaacttc ctggtgcgtt actcacctgt gaaaaatgag gaagatgttg
4201  cagagttgtc aatttctcct tcagacaatg cagtggtctt aacaaatctc ctgcctggta
4261  cagaatatgt agtgagtgtc tccagtgtct acgaacaaca tgagagcaca cctcttagag
4321  gaagacagaa acaggtctt gattccccaa ctggcattga cttttctgat attactgcca
4381  actcttttac tgtgcactgg attgctcctc gagccaccat cactggctac aggatccgcc
4441  atcatcccga gcacttcagt gggagacctc gagaagatcg ggtgccccac tctcggaatt
4501  ccatcaccct caccaacctc actccaggca cagagtatgt ggtcagcatc gttgctctta
4561  atggcagaga ggaaagtccc ttattgattg ccaacaatc aacagtttct gatgttccga
4621  gggacctgga agttgttgct gcgaccccca ccagcctact gatcagctgg gatgctcctg
4681  ctgtcacagt gagatattac aggatcactt acggagaaac aggaggaaat agccctgtcc
4741  aggagttcac tgtgcctggg agcaagtcta cagctaccat cagcggcctt aaacctggag
4801  ttgattatac catcactgtg tatgctgtca ctggccgtgg agacagcccc gcaagcagca
4861  agccaatttc cattaattac cgaacagaaa ttgacaaacc atcccagatg caagtgaccg
4921  atgttcagga caacagcatt agtgtcaagt ggctgccttc aagttcccct gttactggtt
4981  acagagtaac caccactccc aaaaatggac caggaccaac aaaaactaaa actgcaggtc
5041  cagatcaaac agaaatgact attgaaggct tgcagcccac agtggagtat gtggttagtg
```

-continued

```
5101 tctatgctca gaatccaagc ggagagagtc agcctctggt tcagactgca gtaaccacta
5161 ttcctgcacc aactgacctg aagttcactc aggtcacacc cacaagcctg agcgcccagt
5221 ggacaccacc caatgttcag ctcactggat atcgagtgcg ggtgacccccc aaggagaaga
5281 ccggaccaat gaaagaaatc aaccttgctc ctgacagctc atccgtggtt gtatcaggac
5341 ttatggtggc caccaaatat gaagtgagtg tctatgctct taaggacact tgacaagca
5401 gaccagctca gggagttgtc accactctgg agaatgtcag cccaccaaga agggctcgtg
5461 tgacagatgc tactgagacc accatcacca ttagctggag aaccaagact gagacgatca
5521 ctggcttcca agttgatgcc gttccagcca atggccagac tccaatccag agaaccatca
5581 agccagatgt cagaagctac accatcacag gtttacaacc aggcactgac tacaagatct
5641 acctgtacac cttgaatgac aatgctcgga gctcccctgt ggtcatcgac gcctccactg
5701 ccattgatgc accatccaac ctgcgtttcc tggccaccac acccaattcc ttgctggtat
5761 catggcagcc gccacgtgcc aggattaccg gctacatcat caagtatgag aagcctgggt
5821 ctcctcccag agaagtggtc cctcggcccc gccctggtgt cacagaggct actattactg
5881 gcctggaacc gggaaccgaa tatacaattt atgtcattgc cctgaagaat aatcagaaga
5941 gcgagcccct gattggaagg aaaaagacag acgagcttcc ccaactggta acccttccac
6001 accccaatct tcatggacca gagatcttgg atgttccttc cacagttcaa aagacccctt
6061 tcgtcaccca ccctgggtat gacactggaa atggtattca gcttcctggc acttctggtc
6121 agcaacccag tgttgggcaa caaatgatct ttgaggaaca tggttttagg cggaccacac
6181 cgcccacaac ggccaccccc ataaggcata ggccaagacc atcccgccg aatgtaggac
6241 aagaagctct ctctcagaca accatctcat gggcccccatt ccaggacact tctgagtaca
6301 tcatttcatg tcatcctgtt ggcactgatg aagaaccctt acagttcagg gttcctggaa
6361 cttctaccag tgccactctg acaggcctca ccagaggtgc cacctacaac atcatagtgg
6421 aggcactgaa agaccagcag aggcataagg ttcgggaaga ggttgttacc gtgggcaact
6481 ctgtcaacga aggcttgaac caacctacgg atgactcgtg ctttgacccc tacacagttt
6541 cccattatgc cgttggagat gagtgggaac gaatgtctga atcaggcttt aaactgttgt
6601 gccagtgctt aggctttgga agtggtcatt tcagatgtga ttcatctaga tggtgccatg
6661 acaatggtgt gaactacaag attggagaga agtgggaccg tcaggagaa atggccaga
6721 tgatgagctg cacatgtctt gggaacggaa aaggagaatt caagtgtgac cctcatgagg
6781 caacgtgtta cgatgatggg aagacatacc acgtaggaga acagtggcag aaggaatatc
6841 tcggtgccat ttgctcctgc acatgctttg gaggccagcg gggctggcgc tgtgacaact
6901 gccgcagacc tgggggtgaa cccagtcccg aaggcactac tggccagtcc tacaaccagt
6961 attctcagag ataccatcag agaacaaaca ctaatgttaa ttgcccaatt gagtgcttca
7021 tgcctttaga tgtacaggct gacagagaag attcccgaga gtaaatcatc tttccaatcc
7081 agaggaacaa gcatgtctct ctgccaagat ccatctaaac tggagtgatg ttagcagacc
7141 cagcttagag ttcttctttc tttcttaagc cctttgctct ggaggaagtt ctccagcttc
7201 agctcaactc acagcttctc caagcatcac cctgggagtt tcctgagggt tttctcataa
7261 atgagggctg cacattgcct gttctgcttc gaagtattca ataccgctca gtattttaaa
7321 tgaagtgatt ctaagatttg gtttgggatc aataggaaag catatgcagc caaccaagat
7381 gcaaatgttt tgaaatgata tgaccaaaat tttaagtagg aaagtcaccc aaacacttct
7441 gctttcactt aagtgtctgg cccgcaatac tgtaggaaca agcatgatct tgttactgtg
7501 atattttaaa tatccacagt actcacttt tccaaatgat cctagtaatt gcctagaaat
```

-continued

```
7561 atctttctct tacctgttat ttatcaattt ttcccagtat ttttatacgg aaaaaattgt 7621 attgaaaaca cttagtatgc agttgataag aggaatttgg tataattatg gtgggtgatt 7681 atttttata ctgtatgtgc caaagcttta ctactgtgga aagacaactg ttttaataaa 7741 agatttacat tcc
```

SEQ ID No: 2: protein sequence for Fibronectin 1 [Homo sapiens] (2265 aa), GenBank accession No BAD52437.1

```
   1 MLRGPGPGLL LLAVQCLGTA VPSTGASKSK RQAQQMVQPQ SPVAVSQSKP GCYDNGKHYQ

61 INQQWERTYL GNALVCTCYG GSRGFNCESK PEAEETCFDK YTGNTYRVGD TYERPKDSMI

121 WDCTCIGAGR GRISCTIANR CHEGGQSYKI GDTWRRPHET GGYMLECVCL GNGKGEWTCK

181 PIAEKCFDHA AGTSYVVGET WEKPYQGWMM VDCTCLGEGS GRITCTSRNR CNDQDTRTSY

241 RIGDTWSKKD NRGNLLQCIC TGNGRGEWKC ERHTSVQTTS SGSGPFTDVR AAVYQPQPHP

301 QPPPYGHCVT DSGVVYSVGM QWLKTQGNKQ MLCTCLGNGV SCQETAVTQT YGGNSNGEPC

361 VLPFTYNGRT FYSCTTEGRQ DGHLWCSTTS NYEQDQKYSF CTDHTVLVQT RGGNSNGALC

421 HFPFLYNNHN YTDCTSEGRR DNMKWCGTTQ NYDADQKFGF CPMAAHEEIC TTNEGVMYRI

481 GDQWDKQHDM GHMMRCTCVG NGRGEWTCIA YSQLRDQCIV DDITYNVNDT FHKRHEEGHM

541 LNCTCFGQGR GRWKCDPVDQ CQDSETGTFY QIGDSWEKYV HGVRYQCYCY GRGIGEWHCQ

601 PLQTYPSSSG PVEVFITETP SQPNSHPIQW NAPQPSHISK YILRWRPKNS VGRWKEATIP

661 GHLNSYTIKG LKPGVVYEGQ LISIQQYGHQ EVTRFDFTTT STSTPVTSNT VTGETTPFSP

721 LVATSESVTE ITASSFVVSW VSASDTVSGF RVEYELSEEG DEPQYLDLPS TATSVNIPDL

781 LPGRKYIVNV YQISEDGEQS LILSTSQTTA PDAPPDPTVD QVDDTSIVVR WSRPQAPITG

841 YRIVYSPSVE GSSTELNLPE TANSVTLSDL QPGVQYNITI YAVEENQEST PVVIQQETTG

901 TPRSDTVPSP RDLQFVEVTD VKVTIMWTPP ESAVTGYRVD VIPVNLPGEH GQRLPISRNT

961 FAEVTGLSPG VTYYFKVFAV SHGRESKPLT AQQTTKLDAP TNLQFVNETD STVLRWTPP

1021 RAQITGYRLT VGLTRRGQPR QYNVGPSVSK YPLRNLQPAS EYTVSLVAIK GNQESPKATG

1081 VFTTLQPGSS IPPYNTEVTE TTIVITWTPA PRIGFKLGVR PSQGGEAPRE VTSDSGSIVV

1141 SGLTPGVEYV YTIQVLRDGQ ERDAPIVNKV VTPLSPPTNL HLEANPDTGV LTVSWERSTT

1201 PDITGYRITT TPTNGQQGNS LEEVVHADQS SCTFDNLSPG LEYNVSVYTV KDDKESVPIS

1261 DTIIPAVPPP TDLRFTNIGP DTMRVTWAPP PSIDLTNFLV RYSPVKNEED VAELSISPSD

1321 NAVVLTNLLP GTEYVVSVSS VYEQHESTPL RGRQKTGLDS PTGIDFSDIT ANSFTVHWIA

1381 PRATITGYRI RHHPEHFSGR PREDRVPHSR NSITLTNLTP GTEYVVSIVA LNGREESPLL

1441 IGQQSTVSDV PRDLEVVAAT PTSLLISWDA PAVTVRYYRI TYGETGGNSP VQEFTVPGSK

1501 STATISGLKP GVDYTITVYA VTGRGDSPAS SKPISINYRT EIDKPSQMQV TDVQDNSISV

1561 KWLPSSSPVT GYRVTTTPKN GPGPTKTKTA GPDQTEMTIE GLQPTVEYVV SVYAQNPSGE

1621 SQPLVQTAVT TIPAPTDLKF TQVTPTSLSA QWTPPNVQLT GYRVRVTPKE KTGPMKEINL

1681 APDSSSVVVS GLMVATKYEV SVYALKDTLT SRPAQGVVTT LENVSPPRRA RVTDATETTI

1741 TISWRTKTET ITGFQVDAVP ANGQTPIQRT IKPDVRSYTI TGLQPGTDYK IYLYTLNDNA

1801 RSSPVVIDAS TAIDAPSNLR FLATTPNSLL VSWQPPRARI TGYIIKYEKP GSPPREVVPR

1861 PRPGVTEATI TGLEPGTEYT IYVIALKNNQ KSEPLIGRKK TDELPQLVTL PHPNLHGPEI

1921 LDVPSTVQKT PFVTHPGYDT GNGIQLPGTS GQQPSVGQQM IFEEHGFRRT TPPTTATPIR

1981 HRPRPYPPNV GQEALSQTTI SWAPFQDTSE YIISCHPVGT DEEPLQFRVP GTSTSATLTG

2041 LTRGATYNII VEALKDQQRH KVREEVVTVG NSVNEGLNQP TDDSCFDPYT VSHYAVGDEW
```

2101 ERMSESGFKL LCQCLGFGSG HFRCDSSRWC HDNGVNYKIG EKWDRQGENG QMMSCTCLGN

2161 GKGEFKCDPH EATCYDDGKT YHVGEQWQKE YLGAICSCTC FGGQRGWRCD NCRRPGGEPS

2221 PEGTTGQSYN QYSQRYHQRT NTNVNCPIEC FMPLDVQADR EDSRE

SEQ ID No: 3: mRNA for Migration Stimulating Factor [Homo sapiens] (2192 bp);
GenBank accession No AJ535086.1

```
   1 caaacttggt ggcaacttgc ctcccggtgc gggcgtctct cccccaccgt ctcaacatgc
  61 ttagggggtcc ggggcccggg ctgctgctgc tggccgtcca gtgcctgggg acagcggtgc
 121 cctccacggg agcctcgaag agcaagaggc aggctcagca aatggttcag ccccagtccc
 181 cggtggctgt cagtcaaagc aagcccggtt gttatgacaa tggaaaacac tatcagataa
 241 atcaacagtg ggagcggacc tacctaggca atgcgttggt ttgtacttgt tatggaggaa
 301 gccgaggttt taactgcgag agtaaacctg aagctgaaga gacttgcttt gacaagtaca
 361 ctgggaacac ttaccgagtg ggtgacactt atgagcgtcc taaagactcc atgatctggg
 421 actgtacctg catcggggct gggcgaggga aataagctg taccatcgca aaccgctgcc
 481 atgaagggg tcagtcctac aagattggtg acacctggag agaccacat gagactggtg
 541 gttacatgtt agagtgtgtg tgtcttggta tggaaaagg agaatggacc tgcaagccca
 601 tagctgagaa gtgttttgat catgctgctg ggacttccta tgtggtcgga gaaacgtggg
 661 agaagcccta ccaaggctgg atgatggtag attgtacttg cctgggagaa ggcagcggac
 721 gcatcacttg cacttctaga aatagatgca acgatcagga cacaaggaca tcctatagaa
 781 ttggagacac ctggcgcaag aaggataatc gaggaaacct gctccagtgc atctgcacag
 841 gcaacgccg aggagagtgg aagtgtgaga ggcacacctc tgtgcagacc atcgagcg
 901 gatctggccc cttcaccgat gttcgtgcag ctgtttacca accgcagcct cacccccagc
 961 ctcctcccta tggccactgt gtcacagaca gtggtgtggt ctactctgtg gggatgcagt
1021 ggctgaagac acaaggaaat aagcaaatgc tttgcacgtg cctgggcaac ggagtcagct
1081 gccaagagac agctgtaacc cagacttacg gtggcaactc aaatggagag ccatgtgtct
1141 taccattcac ctacaatggc aggacgttct actcctgcac cacagaaggg cgacaggacg
1201 gacatctttg gtgcagcaca acttcgaatt atgagcagga ccagaaatac tctttctgca
1261 cagaccacac tgttttggtt cagactcgag gaggaaattc caatggtgcc ttgtgccact
1321 tccccttcct atacaacaac cacaattaca ctgattgcac ttctgagggc agaagagaca
1381 acatgaagtg gtgtgggacc acacagaact atgatgccga ccagaagttt gggttctgcc
1441 ccatggctgc ccacgaggaa atctgcacaa ccaatgaagg ggtcatgtac cgcattggag
1501 atcagtggga taagcagcat gacatgggtc acatgatgag gtgcacgtgt gttgggaatg
1561 gtcgtgggga atggacatgc attgcctact cgcagcttcg agatcagtgc attgttgatg
1621 acatcactta caatgtgaac gacacattcc acaagcgtca tgaagagggg cacatgctga
1681 actgtacatg cttcggtcag ggtcggggca ggtggaagtg tgatcccgtc gaccaatgcc
1741 aggattcaga gactgggacg ttttatcaaa ttggagatta tgggagaag tatgtgcatg
1801 gtgtcagata ccagtgctac tgctatggcc gtggcattgg ggagtggcat tgccaacctt
1861 tacagaccta tccaagctca gtggtcctg tcgaagtatt tatcactgag actccgagtc
1921 agcccaactc ccaccccatc cagtggaatg caccacagcc atctcacatt tccaagtaca
1981 ttctcaggtg gagacctgtg agtatcccac ccagaaacct tggatactga gtctcctaat
2041 cttatcaatt ctgatggttt cttttttttcc cagcttttga gccaacaact ctgattaact
2101 attcctatag catttactat atttgtttag tgaacaaaca atatgtggtc aattaaattg
2161 acttgtagac tgaaaaaaaa aaaaaaaaaa aa
```

SEQ ID No: 4: protein sequence for Migration Stimulating Factor [Homo sapiens] (657 aa);
GenBank n° CAH60958.1

```
  1 MLRGPGPGLL LLAVQCLGTA VPSTGASKSK RQAQQMVQPQ SPVAVSQSKP GCYDNGKHYQ
 61 INQQWERTYL GNALVCTCYG GSRGFNCESK PEAEETCFDK YTGNTYRVGD TYERPKDSMI
121 WDCTCIGAGR GRISCTIANR CHEGGQSYKI GDTWRRPHET GGYMLECVCL GNGKGEWTCK
181 PIAEKCFDHA AGTSYVVGET WEKPYQGWMM VDCTCLGEGS GRITCTSRNR CNDQDTRTSY
241 RIGDTWRKKD NRGNLLQCIC TGNGRGEWKC ERHTSVQTTS SGSGPFTDVR AAVYQPQPHP
301 QPPPYGHCVT DSGVVYSVGM QWLKTQGNKQ MLCTCLGNGV SCQETAVTQT YGGNSNGEPC
361 VLPFTYNGRT FYSCTTEGRQ DGHLWCSTTS NYEQDQKYSF CTDHTVLVQT RGGNSNGALC
421 HFPFLYNNHN YTDCTSEGRR DNMKWCGTTQ NYDADQKFGF CPMAAHEEIC TTNEGVMYRI
481 GDQWDKQHDM GHMMRCTCVG NGRGEWTCIA YSQLRDQCIV DDITYNVNDT FHKRHEEGHM
541 LNCTCFGQGR GRWKCDPVDQ CQDSETGTFY QIGDSWEKYV HGVRYQCYCY GRGIGEWHCQ
601 PLQTYPSSSG PVEVFITETP SQPNSHPIQW NAPQPSHISK YILRWRPVSI PPRNLGY
```

DNA and protein sequences of 1G5.3:
SEQ ID No: 5: DNA sequence of 1G5.3 Heavy chain (1374 bp)
Leader sequence-FR1-CDR1-FR2-CDR2-FR3-CDR3-FR4-Constant region-Stop codon

ATGTACTTGGGACTGAACTGTGTATTCATAGTTTTTCTCTTAAAAGGTGTCCAGAGTGAAGTGAAAA

TTGAGGAGTCTGGAGGAGGCTTGGTGCAACCTGGAGGATCCATGAAACTCTCCTGTGTTGCCTCTGG

ATTCACTTTCAGTAACGACTGGATGAACTGGGTCCGCCAGTCTCCAGAGAAGGGGCTTGAGTGGGTT

GCTGAAATTAGAATGAAATCTGATAATTATGCAACATATTATGCGGAGTCTGTGAAAGGGAGGTTCA

CCATCTCAAGAGATGATTCCAAAAATAGTGTCTACCTGCAAATGAACAATTTAAGAGCTGAAGACAA

TGGCATTTATTACTGTACCAGTTGGGACTACTGGGGCCAAGGCACCACTCTCACAGTCTCCTCAGCC

AAAACGACACCCCCATCTGTCTATCCACTGGCCCCTGGATCTGCTGCCCAAACTAACTCCATGGTGA

CCCTGGGATGCCTGGTCAAGGGCTATTTCCCTGAGCCAGTGACAGTGACCTGGAACTCTGGATCCCT

GTCCAGCGGTGTGCACACCTTCCCAGCTGTCCTGCAGTCTGACCTCTACACTCTGAGCAGCTCAGTG

ACTGTCCCCTCCAGCACCTGGCCCAGCGAGACCGTCACCTGCAACGTTGCCCACCCGGCCAGCAGCA

CCAAGGTGGACAAGAAAATTGTGCCCAGGGATTGTGGTTGTAAGCCTTGCATATGTACAGTCCCAGA

AGTATCATCTGTCTTCATCTTCCCCCCAAAGCCCAAGGATGTGCTCACCATTACTCTGACTCCTAAG

GTCACGTGTGTTGTGGTAGACATCAGCAAGGATGATCCCGAGGTCCAGTTCAGCTGGTTTGTAGATG

ATGTGGAGGTGCACACAGCTCAGACGCAACCCCGGGAGGAGCAGTTCAACAGCACTTTCCGCTCAGT

CAGTGAACTTCCCATCATGCACCAGGACTGGCTCAATGGCAAGGAGTTCAAATGCAGGGTCAACAGT

GCAGCTTTCCCTGCCCCCATCGAGAAACCATCTCCAAAACCAAAGGCAGACCGAAGGCTCCACAGG

TGTACACCATTCCACCTCCCAAGGAGCAGATGGCCAAGGATAAAGTCAGTCTGACCTGCATGATAAC

AGACTTCTTCCCTGAAGACATTACTGTGGAGTGGCAGTGGAATGGGCAGCCAGCGGAGAACTACAAG

AACACTCAGCCCATCATGGACACAGATGGCTCTTACTTCGTCTACAGCAAGCTCAATGTGCAGAAGA

GCAACTGGGAGGCAGGAAATACTTTCACCTGCTCTGTGTTACATGAGGGCCTGCACAACCACCATAC

TGAGAAGAGCCTCTCCCACTCTCCTGGTAAATGA

SEQ ID No: 6: Protein sequence of 1G5.3 Heavy chain (457 aa):
Leader sequence-FR1-CDR1-FR2-CDR2-FR3-CDR3-FR4-Constant region-Stop codon

MYLGLNCVFIVFLLKGVQSEVKIEESGGGLVQPGGSMKLSCVASGFTFSNDWMNWVRQSPEKGLEWV

AEIRMKSDNYATYYAESVKGRFTISRDDSKNSVYLQMNNLRAEDNGIYYCTSWDYWGQGTTLTVSSA

KTTPPSVYPLAPGSAAQTNSMVTLGCLVKGYFPEPVTVTWNSGSLSSGVHTFPAVLQSDLYTLSSSV

TVPSSTWPSETVTCNVAHPASSTKVDKKIVPRDCGCKPCICTVPEVSSVFIFPPKPKDVLTITLTPK

VTCVVVDISKDDPEVQFSWFVDDVEVHTAQTQPREEQFNSTFRSVSELPIMHQDWLNGKEFKCRVNS

AAFPAPIEKTISKTKGRPKAPQVYTIPPPKEQMAKDKVSLTCMITDFFPEDITVEWQWNGQPAENYK

TQPIMDTDGSYFVYSKLNVQKSNWEAGNTFTCSVLHEGLHNHHTEKSLSHSPGK

SEQ ID No: 7: DNA sequence of 1G5.3 Light chain (720 bp):
Leader sequence-FR1-CDR1-FR2-CDR2-FR3-CDR3-FR4-Constant region-Stop codon
ATGGATTCACAGGCCCAGGTTCTTATATTGCTGCTGCTATGGGTATCTGGTACCTGTGGGGACATTG

TGATGTCACAGTCTCCATCCTCCCTGGCTGTGTCAACAGGAGAGAAGGTCACTATGAACTGCAGATC

CAGTCACTATCTGCTCAACAGTAGAACCCGAAAGAACTTCTTGTCTTGGTACCAACAGAAACCAGGA

CAGTCTCCTCAACTGCTGATCTACTGGGCATCCACTAGGTATTCTGGGGTCCCTGATCGCTTCACAG

GCAGTGGATCTGGGACAGATTTCACTCTCACCATCAGCAGTGTGCAGGCTGAAGACCTGGCAGTTTA

TTACTGCAAACAATCTTATAATCTTCACACGTTCGGAGGGGGGACCAAGTTGGAAATAAAGCGGGCT

GATGCTGCACCAACTGTATCCATCTTCCCACCATCCAGTGAGCAGTTAACATCTGGAGGTGCCTCAG

TCGTGTGCTTCTTGAACAACTTCTACCCCAAAGACATCAATGTCAAGTGGAAGATTGATGGCAGTGA

ACGACAAAATGGCGTCCTGAACAGTTGGACTGATCAGGACAGCAAAGACAGCACCTACAGCATGAGC

AGCACCCTCACGTTGACCAAGGACGAGTATGAACGACATAACAGCTATACCTGTGAGGCCACTCACA

AGACATCAACTTCACCCATTGTCAAGAGCTTCAACAGGAATGAGTGTTAG

SEQ ID No: 8: Protein sequence of 1G5.3 light chain (239 aa):
Leader sequence-FR1-CDR1-FR2-CDR2-FR3-CDR3-FR4-Constant region-Stop codon
MDSQAQVLILLLLWVSGTCGDIVMSQSPSSLAVSTGEKVTMNCRSSHYLLNSRTRKNFLSWYQQKPG

QSPQLLIYWASTRYSGVPDRFTGSGSGTDFTLTISSVQAEDLAVYYCKQSYNLHTFGGGTKLEIKRA

DAAPTVSIFPPSSEQLTSGGASVVCFLNNFYPKDINVKWKIDGSERQNGVLNSWTDQDSKDSTYSMS

STLTLTKDEYERHNSYTCEATHKTSTSPIVKSFNRNEC

SEQ ID No: 9: Decapeptide specific of MSF (aa 648-657 of SEQ ID No 4) wherein a
cysteine is added at the COOH-terminal
VSIPPRNLGYC SEQ ID No: 10: His-MSF (aa 553-657of SEQ ID No 4 plus His Tag; 123 aa)
MGSDKIHHHH HHHHHHGVWK CDPVDQCQDS ETGTFYQIGD SWEKYVHGVR

YQCYCYGRGI GEWHCQPLQT YPSSSGPVEV FITETPSQPN SHPIQWNAPQ

PSHISKYILR WRPVSIPPRN LGY

SEQ ID No: 11: Decapeptide specific of MSF (aa 648-657 of SEQ ID No 4)
VSIPPRNLGY

REFERENCES

1. Murray P J, Allen J E, Biswas S K, Fisher E A, Gilroy D W, Goerdt S, Gordon S, Hamilton J A, Ivashkiv L B, Lawrence T, et al.: Macrophage activation and polarization: nomenclature and experimental guidelines. *Immunity* 2014, 41:14-20.
2. Gordon S, Martinez F O: Alternative activation of macrophages: mechanism and functions. *Immunity* 2010, 32:593-604.
3. Mantovani A, Allavena P, Sica A, Balkwill F: Cancer-related inflammation. *Nature* 2008, 454:436-444.
4. Hanahan D, Weinberg R A: Hallmarks of cancer: the next generation. *Cell* 2011, 144:646-674.
5. Coussens L M, Zitvogel L, Palucka A K: Neutralizing tumor-promoting chronic inflammation: a magic bullet? *Science* 2013, 339:286-291.
6. Mantovani A, Bottazzi B, Colotta F, Sozzani S, Ruco L: The origin and function of tumor-associated macrophages. *Immunol Today* 1992, 13:265-270.

7. Noy R, Pollard J W: Tumor-associated macrophages: from mechanisms to therapy. *Immunity* 2014, 41:49-61.
8. De Palma M, Lewis C E: Macrophage regulation of tumor responses to anticancer therapies. *Cancer Cell* 2013, 23:277-286.
9. Shabo I, Stal O, Olsson H, Dore S, Svanvik J: Breast cancer expression of CD163, a macrophage scavenger receptor, is related to early distant recurrence and reduced patient survival. *International Journal of Cancer* 2008, 123:780-786.
10. Kurahara H, Shinchi H, Mataki Y, Maemura K, Noma H, Kubo F, Sakoda M, Ueno S, Natsugoe S, Takao S: Significance of M2-polarized tumor-associated macrophage in pancreatic cancer. *Journal of Surgical Research* 2011, 167:e211-219.
11. DeNardo D G, Brennan D J, Rexhepaj E, Ruffell B, Shiao S L, Madden S F, Gallagher W M, Wadhwani N, Keil S D, Junaid S A, et al.: Leukocyte complexity predicts breast cancer survival and functionally regulates response to chemotherapy. *Cancer Discov* 2011, 1:54-67.
12. Steidl C, Lee T, Shah S P, Farinha P, Han G, Nayar T, Delaney A, Jones S J, Iqbal J, Weisenburger D D, et al.: Tumor-associated macrophages and survival in classic Hodgkin's lymphoma. *N Engl J Med* 2010, 362:875-885.
13. Germano G, Frapolli R, Belgiovine C, Anselmo A, Pesce S, Liguori M, Erba E, Uboldi S, Zucchetti M, Pasqualini F, et al.: Role of macrophage targeting in the antitumor activity of trabectedin. *Cancer Cell* 2013, 23:249-262.
14. Ries C H, Cannarile M A, Hoves S, Benz J, Wartha K, Runza V, Rey-Giraud F, Pradel L P, Feuerhake F, Klaman I, et al.: Targeting tumor-associated macrophages with anti-CSF-1R antibody reveals a strategy for cancer therapy. *Cancer Cell* 2014, 25:846-859.
15. Wynn T A, Chawla A, Pollard J W: Macrophage biology in development, homeostasis and disease. *Nature* 2013, 496:445-455.
16. Quail D F, Joyce J A: Microenvironmental regulation of tumor progression and metastasis. *Nature Medicine* 2013, 19:1423-1437.
17. Mantovani A, Allavena P: The interaction of anticancer therapies with tumor-associated macrophages. *Journal of Experimental Medicine* 2015, 212:435-445.
18. Solinas G, Schiarea S, Liguori M, Fabbri M, Pesce S, Zammataro L, Pasqualini F, Nebuloni M, Chiabrando C, Mantovani A, et al.: Tumor-conditioned macrophages secrete migration-stimulating factor: a new marker for m2-polarization, influencing tumor cell motility. *J Immunol* 2010, 185:642-652.
19. Schor S L, Ellis I R, Jones S J, Baillie R, Seneviratne K, Clausen J, Motegi K, Vojtesek B, Kankova K, Furrie E, et al.: Migration-stimulating factor: a genetically truncated onco-fetal fibronectin isoform expressed by carcinoma and tumor-associated stromal cells. *Cancer Res* 2003, 63:8827-8836.
20. Schor A M and Schor S L: Angiogenesis and tumour progression: migration-stimulating factor as a novel target for clinical intervention. *Eye* 2010, 24:450-458.
21. Grey A M, Schor A M, Rushton G, Ellis I, Schor S L: Purification of the migration stimulating factor produced by fetal and breast cancer patient fibroblasts. Proc Natl Acad Sci USA 1989, 86:2438-2442.
22. Schor S L, Grey A M, Ellis I, Schor A M, Coles B, Murphy R: Migration stimulating factor (MSF): its structure, mode of action and possible function in health and disease. Symp Soc Exp Biol 1993, 47:235-251.
23. Aljorani L E, Bankfalvi A, Carey F A, Harada K, Ohe G, Jones S J, Ellis I R, Schor S L, Schor A M: Migration-stimulating factor as a novel biomarker in salivary gland tumours. J Oral Pathol Med 2011, 40:747-754.
24. Kay R A, Ellis I R, Jones S J, Perrier S, Florence M M, Schor A M, Schor S L: The expression of migration stimulating factor, a potent oncofetal cytokine, is uniquely controlled by 3'-untranslated region-dependent nuclear sequestration of its precursor messenger RNA. Cancer Res. 2005 Dec. 1; 65(23):10742-9.

SEQUENCE LISTING

```
<160> NUMBER OF SEQ ID NOS: 21

<210> SEQ ID NO 1
<211> LENGTH: 7753
<212> TYPE: DNA
<213> ORGANISM: Homo sapiens

<400> SEQUENCE: 1
gcccgcgccg gctgtgctgc acaggggag gagagggaac cccagcgcg agcgggaaga      60 ggggacctgc agccacaact tctctggtcc tctgcatccc ttctgtccct ccacccgtcc    120
ccttccccac cctctggccc ccaccttctt ggaggcgaca accccggga ggcattagaa     180 gggattttc ccgcaggttg cgaagggaag caaacttggt ggcaacttgc ctcccggtgc     240
gggcgtctct cccccaccgt ctcaacatgc ttaggggtcc ggggcccggg ctgctgctgc    300
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
gttatgacaa tggaaaacac tatcagataa atcaacagtg ggagcggacc tacctaggca    480
atgcgttggt ttgtacttgt tatggaggaa gccgaggttt taactgcgag agtaaacctg    540
aagctgaaga gacttgcttt gacaagtaca ctgggaacac ttaccgagtg ggtgacactt    600
atgagcgtcc taaagactcc atgatctggg actgtacctg catcggggct gggcgaggga    660
```

```
gaataagctg taccatcgca aaccgctgcc atgaaggggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgacg gatctggccc cttcaccgat gttcgtgcag    1140
ctgtttacca accgcagcct caccccagc ctcctcccta tggccactgt gtcacagaca    1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatggagag ccatgtgtct taccattcac ctacaatggc aggacgttct   1380
actcctgcac cacagaaggg cgacaggacg gacatctttg gtgcagcaca acttcgaatt   1440
atgagcagga ccagaaatac tctttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattggag atcagtggga taagcagcat gacatggggtc   1740 acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaaccct tacagaccta ccaagctca agtggtcctg    2100 tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactccctt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatggggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
```

```
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cgggctgtcc cctggggtca    3180
cctattactt caaagtcttt gcagtgagcc atgggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggccag cccaggcagt acaatgtggg tccctctgtc tccaagtacc    3420
ccctgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccagggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagaggagc accaccccag acattactgg ttatagaatt accacaaccc    3900
ctacaaacgg ccagcaggga aattctttgg aagaagtggt ccatgctgat cagagctcct    3960
gcacttttga taacctgagt cccggcctgg agtacaatgt cagtgtttac actgtcaagg    4020
atgacaagga aagtgtccct atctctgata ccatcatccc agctgttcct cctcccactg    4080
acctgcgatt caccaacatt ggtccagaca ccatgcgtgt cacctgggct ccaccccat     4140 ccattgattt aaccaacttc ctggtgcgtt actcacctgt gaaaaatgag gaagatgttg    4200
cagagttgtc aatttctcct tcagacaatg cagtggtctt aacaaatctc ctgcctggta    4260
cagaatatgt agtgagtgtc tccagtgtct acgaacaaca tgagagcaca cctcttagag    4320
gaagacagaa aacaggtctt gattccccaa ctggcattga cttttctgat attactgcca    4380
actcttttac tgtgcactgg attgctcctc gagccaccat cactggctac aggatccgcc    4440
atcatcccga gcacttcagt gggagacctc gagaagatcg ggtgcccac tctcggaatt     4500 ccatcaccct caccaacctc actccaggca cagagtatgt ggtcagcatc gttgctctta    4560
atggcagaga ggaaagtccc ttattgattg ccaacaatc aacagtttct gatgttccga     4620
gggacctgga agttgttgct gcgaccccca ccagcctact gatcagctgg gatgctcctg    4680
ctgtcacagt gagatattac aggatacactt acggagaaac aggaggaaat agccctgtcc    4740
aggagttcac tgtgcctggg agcaagtcta cagctaccat cagcggcctt aaacctggag    4800
ttgattatac catcactgtg tatgctgtca ctggccgtgg agacagcccc gcaagcagca    4860
agccaatttc cattaattac cgaacagaaa ttgacaaacc atcccagatg caagtgaccg    4920
atgttcagga acacagcatt agtgtcaagt ggctgccttc aagttcccct gttactggtt    4980
acagagtaac caccactccc aaaaatggac caggaccaac aaaaactaaa actgcaggtc    5040
cagatcaaac agaaatgact attgaaggct tgcagcccac agtggagtat gtggttagtg    5100
tctatgctca gaatccaagc ggagagagtc agcctctggt tcagactgca gtaaccacta    5160
ttcctgcacc aactgacctg aagttcactc aggtcacacc cacaagcctg agcgcccagt    5220
ggacaccacc caatgttcag ctcactggat atcgagtgcg ggtgacccc aaggagaaga    5280 ccggaccaat gaaagaaatc aaccttgctc ctgcagctc atccgtggtt gtatcaggac    5340
ttatggtggc caccaaatat gaagtgagtg tctatgctct taaggacact ttgacaagca    5400
```

```
gaccagctca gggagttgtc accactctgg agaatgtcag cccaccaaga agggctcgtg    5460
tgacagatgc tactgagacc accatcacca ttagctggag aaccaagact gagacgatca    5520
ctggcttcca agttgatgcc gttccagcca atgccagac tccaatccag agaaccatca    5580
agccagatgt cagaagctac accatcacag gtttacaacc aggcactgac tacaagatct    5640
acctgtacac cttgaatgac aatgctcgga gctccctgt ggtcatcgac gcctccactg    5700
ccattgatgc accatccaac ctgcgtttcc tggccaccac acccaattcc ttgctggtat    5760
catggcagcc gccacgtgcc aggattaccg gctacatcat caagtatgag aagcctgggt    5820
ctcctcccag agaagtggtc cctcggcccc gccctggtgt cacagaggct actattactg    5880
gcctggaacc gggaaccgaa tatacaattt atgtcattgc cctgaagaat aatcagaaga    5940
gcgagcccct gattggaagg aaaaagacag acgagcttcc ccaactggta acccttccac    6000
accccaatct tcatggacca gagatcttgg atgttccttc cacagttcaa aagacccctt    6060
tcgtcaccca ccctgggtat gacactggaa atggtattca gcttcctggc acttctggtc    6120
agcaacccag tgttgggcaa caaatgatct ttgaggaaca tggttttagg cggaccacac    6180
cgcccacaac ggccacccccc ataaggcata ggccaagacc atacccgccg aatgtaggac    6240
aagaagctct ctctcagaca accatctcat gggccccatt ccaggacact tctgagtaca    6300
tcatttcatg tcatcctgtt ggcactgatg aagaaccctt acagttcagg gttcctggaa    6360
cttctaccag tgccactctg acaggcctca ccagaggtgc cacctacaac atcatagtgg    6420
aggcactgaa agaccagcag aggcataagg ttcgggaaga ggttgttacc gtgggcaact    6480
ctgtcaacga aggcttgaac caacctacgg atgactcgtg ctttgacccc tacacagttt    6540
cccattatgc cgttggagat gagtgggaac gaatgtctga atcaggcttt aaactgttgt    6600
gccagtgctt aggctttgga agtggtcatt tcagatgtga ttcatctaga tggtgccatg    6660
acaatggtgt gaactacaag attggagaga agtgggaccg tcaggagaa aatggccaga    6720 tgatgagctg cacatgtctt gggaacggaa aaggagaatt caagtgtgac cctcatgagg    6780
caacgtgtta cgatgatggg aagacatacc acgtaggaga acagtggcag aaggaatatc    6840
tcggtgccat ttgctcctgc acatgctttg gaggccagcg gggctggcgc tgtgacaact    6900
gccgcagacc tggggtgaa cccagtcccg aaggcactac tggccagtcc tacaaccagt    6960
attctcagag ataccatcag agaacaaaca ctaatgttaa ttgcccaatt gagtgcttca    7020
tgcctttaga tgtacaggct gacagagaag attcccgaga gtaaatcatc tttccaatcc    7080
agaggaacaa gcatgtctct ctgccaagat ccatctaaac tggagtgatg ttagcagacc    7140
cagcttagag ttcttctttc tttcttaagc cctttgctct ggaggaagtt ctccagcttc    7200
agctcaactc acagcttctc caagcatcac cctgggagtt tcctgagggt tttctcataa    7260
atgagggctg cacattgcct gttctgcttc gaagtattca ataccgctca gtattttaaa    7320
tgaagtgatt ctaagatttg gtttgggatc aataggaaag catatgcagc caaccaagat    7380
gcaaatgttt tgaaatgata tgaccaaaat tttaagtagg aaagtcaccc aaacacttct    7440
gctttcactt aagtgtctgg cccgcaatac tgtaggaaca agcatgatct tgttactgtg    7500
atattttaaa tatccacagt actcactttt tccaaatgat cctagtaatt gcctagaaat    7560
atctttctct tacctgttat ttatcaattt ttcccagtat ttttatacgg aaaaaattgt    7620
attgaaaaca cttagtatgc agttgataag aggaatttgg tataattatg gtgggtgatt    7680
attttttata ctgtatgtgc caaagcttta ctactgtgga aagacaactg ttttaataaa    7740
```
agatttacat tcc                                                    7753

<210> SEQ ID NO 2
<211> LENGTH: 2265
<212> TYPE: PRT
<213> ORGANISM: Homo sapiens

<400> SEQUENCE: 2

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65              70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

```
Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
```

-continued

```
            785                 790                 795                 800
Leu Ile Leu Ser Thr Ser Gln Thr Thr Ala Pro Asp Ala Pro Pro Asp
                    805                 810                 815
Pro Thr Val Asp Gln Val Asp Asp Thr Ser Ile Val Val Arg Trp Ser
                    820                 825                 830
Arg Pro Gln Ala Pro Ile Thr Gly Tyr Arg Ile Val Tyr Ser Pro Ser
                    835                 840                 845
Val Glu Gly Ser Ser Thr Glu Leu Asn Leu Pro Glu Thr Ala Asn Ser
                    850                 855                 860
Val Thr Leu Ser Asp Leu Gln Pro Gly Val Gln Tyr Asn Ile Thr Ile
                    865                 870                 875                 880
Tyr Ala Val Glu Glu Asn Gln Glu Ser Thr Pro Val Val Ile Gln Gln
                                885                 890                 895
Glu Thr Thr Gly Thr Pro Arg Ser Asp Thr Val Pro Ser Pro Arg Asp
                    900                 905                 910
Leu Gln Phe Val Glu Val Thr Asp Val Lys Val Thr Ile Met Trp Thr
                    915                 920                 925
Pro Pro Glu Ser Ala Val Thr Gly Tyr Arg Val Asp Val Ile Pro Val
                    930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                    965                 970                 975
Val Phe Ala Val Ser His Gly Arg Glu Ser Lys Pro Leu Thr Ala Gln
                    980                 985                 990
Gln Thr Thr Lys Leu Asp Ala Pro Thr Asn Leu Gln Phe Val Asn Glu
                    995                 1000                1005
Thr Asp Ser Thr Val Leu Val Arg Trp Thr Pro Pro Arg Ala Gln
                    1010                1015                1020
Ile Thr Gly Tyr Arg Leu Thr Val Gly Leu Thr Arg Arg Gly Gln
                    1025                1030                1035
Pro Arg Gln Tyr Asn Val Gly Pro Ser Val Ser Lys Tyr Pro Leu
                    1040                1045                1050
Arg Asn Leu Gln Pro Ala Ser Glu Tyr Thr Val Ser Leu Val Ala
                    1055                1060                1065
Ile Lys Gly Asn Gln Glu Ser Pro Lys Ala Thr Gly Val Phe Thr
                    1070                1075                1080
Thr Leu Gln Pro Gly Ser Ser Ile Pro Pro Tyr Asn Thr Glu Val
                    1085                1090                1095
Thr Glu Thr Thr Ile Val Ile Thr Trp Thr Pro Ala Pro Arg Ile
                    1100                1105                1110
Gly Phe Lys Leu Gly Val Arg Pro Ser Gln Gly Gly Glu Ala Pro
                    1115                1120                1125
Arg Glu Val Thr Ser Asp Ser Gly Ser Ile Val Val Ser Gly Leu
                    1130                1135                1140
Thr Pro Gly Val Glu Tyr Val Tyr Thr Ile Gln Val Leu Arg Asp
                    1145                1150                1155
Gly Gln Glu Arg Asp Ala Pro Ile Val Asn Lys Val Val Thr Pro
                    1160                1165                1170
Leu Ser Pro Pro Thr Asn Leu His Leu Glu Ala Asn Pro Asp Thr
                    1175                1180                1185
Gly Val Leu Thr Val Ser Trp Glu Arg Ser Thr Thr Pro Asp Ile
                    1190                1195                1200
```

Thr Gly Tyr Arg Ile Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Ala Val Pro Pro Thr Asp Leu Arg Phe Thr Asn Ile
    1265                1270                1275

Gly Pro Asp Thr Met Arg Val Thr Trp Ala Pro Pro Ser Ile
    1280                1285                1290

Asp Leu Thr Asn Phe Leu Val Arg Tyr Ser Pro Val Lys Asn Glu
    1295                1300                1305

Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560

Pro Ser Ser Ser Pro Val Thr Gly Tyr Arg Val Thr Thr Thr Pro
    1565                1570                1575

Lys Asn Gly Pro Gly Pro Thr Lys Thr Lys Thr Ala Gly Pro Asp
    1580                1585                1590

```
Gln Thr Glu Met Thr Ile Glu Gly Leu Gln Pro Thr Val Glu Tyr
1595                1600                1605

Val Val Ser Val Tyr Ala Gln Asn Pro Ser Gly Glu Ser Gln Pro
1610                1615                1620

Leu Val Gln Thr Ala Val Thr Thr Ile Pro Ala Pro Thr Asp Leu
1625                1630                1635

Lys Phe Thr Gln Val Thr Pro Thr Ser Leu Ser Ala Gln Trp Thr
1640                1645                1650

Pro Pro Asn Val Gln Leu Thr Gly Tyr Arg Val Arg Val Thr Pro
1655                1660                1665

Lys Glu Lys Thr Gly Pro Met Lys Glu Ile Asn Leu Ala Pro Asp
1670                1675                1680

Ser Ser Ser Val Val Val Ser Gly Leu Met Val Ala Thr Lys Tyr
1685                1690                1695

Glu Val Ser Val Tyr Ala Leu Lys Asp Thr Leu Thr Ser Arg Pro
1700                1705                1710

Ala Gln Gly Val Val Thr Thr Leu Glu Asn Val Ser Pro Pro Arg
1715                1720                1725

Arg Ala Arg Val Thr Asp Ala Thr Glu Thr Thr Ile Thr Ile Ser
1730                1735                1740

Trp Arg Thr Lys Thr Glu Thr Ile Thr Gly Phe Gln Val Asp Ala
1745                1750                1755

Val Pro Ala Asn Gly Gln Thr Pro Ile Gln Arg Thr Ile Lys Pro
1760                1765                1770

Asp Val Arg Ser Tyr Thr Ile Thr Gly Leu Gln Pro Gly Thr Asp
1775                1780                1785

Tyr Lys Ile Tyr Leu Tyr Thr Leu Asn Asp Asn Ala Arg Ser Ser
1790                1795                1800

Pro Val Val Ile Asp Ala Ser Thr Ala Ile Asp Ala Pro Ser Asn
1805                1810                1815

Leu Arg Phe Leu Ala Thr Thr Pro Asn Ser Leu Leu Val Ser Trp
1820                1825                1830

Gln Pro Pro Arg Ala Arg Ile Thr Gly Tyr Ile Ile Lys Tyr Glu
1835                1840                1845

Lys Pro Gly Ser Pro Pro Arg Glu Val Val Pro Arg Pro Arg Pro
1850                1855                1860

Gly Val Thr Glu Ala Thr Ile Thr Gly Leu Glu Pro Gly Thr Glu
1865                1870                1875

Tyr Thr Ile Tyr Val Ile Ala Leu Lys Asn Asn Gln Lys Ser Glu
1880                1885                1890

Pro Leu Ile Gly Arg Lys Lys Thr Asp Glu Leu Pro Gln Leu Val
1895                1900                1905

Thr Leu Pro His Pro Asn Leu His Gly Pro Glu Ile Leu Asp Val
1910                1915                1920

Pro Ser Thr Val Gln Lys Thr Pro Phe Val Thr His Pro Gly Tyr
1925                1930                1935

Asp Thr Gly Asn Gly Ile Gln Leu Pro Gly Thr Ser Gly Gln Gln
1940                1945                1950

Pro Ser Val Gly Gln Gln Met Ile Phe Glu Glu His Gly Phe Arg
1955                1960                1965

Arg Thr Thr Pro Pro Thr Thr Ala Thr Pro Ile Arg His Arg Pro
1970                1975                1980

Arg Pro Tyr Pro Pro Asn Val Gly Gln Glu Ala Leu Ser Gln Thr
```

| | | | | | | | | | | |
|---|---|---|---|---|---|---|---|---|---|---|
| | | 1985 | | | | 1990 | | | 1995 | |
| Thr | Ile | Ser | Trp | Ala | Pro | Phe | Gln | Asp | Thr | Ser | Glu | Tyr | Ile | Ile |
| 2000 | | | | | 2005 | | | | | 2010 |
| Ser | Cys | His | Pro | Val | Gly | Thr | Asp | Glu | Glu | Pro | Leu | Gln | Phe | Arg |
| 2015 | | | | | 2020 | | | | | 2025 |
| Val | Pro | Gly | Thr | Ser | Thr | Ser | Ala | Thr | Leu | Thr | Gly | Leu | Thr | Arg |
| 2030 | | | | | 2035 | | | | | 2040 |
| Gly | Ala | Thr | Tyr | Asn | Ile | Ile | Val | Glu | Ala | Leu | Lys | Asp | Gln | Gln |
| 2045 | | | | | 2050 | | | | | 2055 |
| Arg | His | Lys | Val | Arg | Glu | Glu | Val | Val | Thr | Val | Gly | Asn | Ser | Val |
| 2060 | | | | | 2065 | | | | | 2070 |
| Asn | Glu | Gly | Leu | Asn | Gln | Pro | Thr | Asp | Asp | Ser | Cys | Phe | Asp | Pro |
| 2075 | | | | | 2080 | | | | | 2085 |
| Tyr | Thr | Val | Ser | His | Tyr | Ala | Val | Gly | Asp | Glu | Trp | Glu | Arg | Met |
| 2090 | | | | | 2095 | | | | | 2100 |
| Ser | Glu | Ser | Gly | Phe | Lys | Leu | Leu | Cys | Gln | Cys | Leu | Gly | Phe | Gly |
| 2105 | | | | | 2110 | | | | | 2115 |
| Ser | Gly | His | Phe | Arg | Cys | Asp | Ser | Ser | Arg | Trp | Cys | His | Asp | Asn |
| 2120 | | | | | 2125 | | | | | 2130 |
| Gly | Val | Asn | Tyr | Lys | Ile | Gly | Glu | Lys | Trp | Asp | Arg | Gln | Gly | Glu |
| 2135 | | | | | 2140 | | | | | 2145 |
| Asn | Gly | Gln | Met | Met | Ser | Cys | Thr | Cys | Leu | Gly | Asn | Gly | Lys | Gly |
| 2150 | | | | | 2155 | | | | | 2160 |
| Glu | Phe | Lys | Cys | Asp | Pro | His | Glu | Ala | Thr | Cys | Tyr | Asp | Asp | Gly |
| 2165 | | | | | 2170 | | | | | 2175 |
| Lys | Thr | Tyr | His | Val | Gly | Glu | Gln | Trp | Gln | Lys | Glu | Tyr | Leu | Gly |
| 2180 | | | | | 2185 | | | | | 2190 |
| Ala | Ile | Cys | Ser | Cys | Thr | Cys | Phe | Gly | Gly | Gln | Arg | Gly | Trp | Arg |
| 2195 | | | | | 2200 | | | | | 2205 |
| Cys | Asp | Asn | Cys | Arg | Arg | Pro | Gly | Gly | Glu | Pro | Ser | Pro | Glu | Gly |
| 2210 | | | | | 2215 | | | | | 2220 |
| Thr | Thr | Gly | Gln | Ser | Tyr | Asn | Gln | Tyr | Ser | Gln | Arg | Tyr | His | Gln |
| 2225 | | | | | 2230 | | | | | 2235 |
| Arg | Thr | Asn | Thr | Asn | Val | Asn | Cys | Pro | Ile | Glu | Cys | Phe | Met | Pro |
| 2240 | | | | | 2245 | | | | | 2250 |
| Leu | Asp | Val | Gln | Ala | Asp | Arg | Glu | Asp | Ser | Arg | Glu |
| 2255 | | | | | 2260 | | | | | 2265 |

<210> SEQ ID NO 3
<211> LENGTH: 2192
<212> TYPE: DNA
<213> ORGANISM: Homo sapiens
<400> SEQUENCE: 3

```
caaacttggt ggcaacttgc ctcccggtgc gggcgtctct ccccaccgt ctcaacatgc      60 ttaggggtcc ggggcccggg ctgctgctgc tggccgtcca gtgcctgggg acagcggtgc    120
cctccacggg agcctcgaag agcaagaggc aggctcagca aatggttcag ccccagtccc    180
cggtggctgt cagtcaaagc aagcccggtt gttatgacaa tggaaaacac tatcagataa    240
atcaacagtg ggagcggacc tacctaggca atgcgttggt ttgtacttgt tatggaggaa    300
gccgaggttt taactgcgag agtaaacctg aagctgaaga gacttgcttt gacaagtaca    360
ctgggaacac ttaccgagtg ggtgacactt atgagcgtcc taaagactcc atgatctggg    420
actgtacctg catcggggct gggcgaggga gaataagctg taccatcgca aaccgctgcc    480
```

```
atgaagggg  tcagtcctac  aagattggtg  acacctggag  gagaccacat  gagactggtg      540
gttacatgtt  agagtgtgtg  tgtcttggta  atggaaaagg  agaatggacc  tgcaagccca      600
tagctgagaa  gtgttttgat  catgctgctg  ggacttccta  tgtggtcgga  gaaacgtggg      660
agaagcccta  ccaaggctgg  atgatggtag  attgtacttg  cctgggagaa  ggcagcggac      720
gcatcacttg  cacttctaga  aatagatgca  acgatcagga  cacaaggaca  tcctatagaa      780
ttggagacac  ctggcgcaag  aaggataatc  gaggaaacct  gctccagtgc  atctgcacag      840
gcaacggccg  aggagagtgg  aagtgtgaga  ggcacacctc  tgtgcagacc  acatcgagcg      900
gatctggccc  cttcaccgat  gttcgtgcag  ctgtttacca  accgcagcct  caccccagc       960 ctcctcccta  tggccactgt  gtcacagaca  gtggtgtggt  ctactctgtg  gggatgcagt     1020
ggctgaagac  acaaggaaat  aagcaaatgc  tttgcacgtg  cctgggcaac  ggagtcagct     1080
gccaagagac  agctgtaacc  cagacttacg  gtggcaactc  aaatggagag  ccatgtgtct     1140
taccattcac  ctacaatggc  aggacgttct  actcctgcac  cacagaaggg  cgacaggacg     1200
gacatctttg  gtgcagcaca  acttcgaatt  atgagcagga  ccagaaatac  tctttctgca     1260
cagaccacac  tgtttggtt   cagactcgag  gaggaaattc  caatggtgcc  ttgtgccact     1320
tccccttcct  atacaacaac  cacaattaca  ctgattgcac  ttctgagggc  agaagagaca     1380
acatgaagtg  gtgtgggacc  acacagaact  atgatgccga  ccagaagttt  gggttctgcc     1440
ccatggctgc  ccacgaggaa  atctgcacaa  ccaatgaagg  ggtcatgtac  cgcattggag     1500
atcagtggga  taagcagcat  gacatgggtc  acatgatgag  gtgcacgtgt  gttgggaatg     1560
gtcgtgggga  atggacatgc  attgcctact  cgcagcttcg  agatcagtgc  attgttgatg     1620
acatcactta  caatgtgaac  gacacattcc  acaagcgtca  tgaagagggg  cacatgctga     1680
actgtacatg  cttcggtcag  ggtcggggca  ggtggaagtg  tgatcccgtc  gaccaatgcc     1740
aggattcaga  gactgggacg  ttttatcaaa  ttggagattc  atgggagaag  tatgtgcatg     1800
gtgtcagata  ccagtgctac  tgctatggcc  gtggcattgg  ggagtggcat  tgccaacctt     1860
tacagaccta  tccaagctca  gtggtcctg   tcgaagtatt  tatcactgag  actccgagtc     1920
agcccaactc  ccacccccatc cagtggaatg  caccacagcc  atctcacatt  tccaagtaca     1980
ttctcaggtg  gagacctgtg  agtatcccac  ccagaaacct  tggatactga  gtctcctaat     2040
cttatcaatt  ctgatggttt  cttttttttcc  cagcttttga  gccaacaact  ctgattaact     2100
attcctatag  catttactat  atttgtttag  tgaacaaaca  atatgtggtc  aattaaattg     2160
acttgtagac  tgaaaaaaaa  aaaaaaaaaa  aa                                    2192
```

<210> SEQ ID NO 4
<211> LENGTH: 657
<212> TYPE: PRT
<213> ORGANISM: Homo sapiens

<400> SEQUENCE: 4

```
Met Leu Arg Gly Pro Gly Pro Gly Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60
```

```
Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Thr
             85                  90                  95

Cys Phe Asp Lys Tyr Thr Gly Asn Thr Tyr Arg Val Gly Asp Thr Tyr
             100                 105                 110

Glu Arg Pro Lys Asp Ser Met Ile Trp Asp Cys Thr Cys Ile Gly Ala
             115                 120                 125

Gly Arg Gly Arg Ile Ser Cys Thr Ile Ala Asn Arg Cys His Glu Gly
     130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
             165                 170                 175

Trp Thr Cys Lys Pro Ile Ala Glu Lys Cys Phe Asp His Ala Ala Gly
             180                 185                 190

Thr Ser Tyr Val Val Gly Glu Thr Trp Glu Lys Pro Tyr Gln Gly Trp
             195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Arg Lys Lys Asp Asn Arg Gly Asn Leu Leu
             245                 250                 255

Gln Cys Ile Cys Thr Gly Asn Gly Arg Gly Glu Trp Lys Cys Glu Arg
             260                 265                 270

His Thr Ser Val Gln Thr Thr Ser Ser Gly Ser Gly Pro Phe Thr Asp
             275                 280                 285

Val Arg Ala Ala Val Tyr Gln Pro Gln Pro His Pro Gln Pro Pro Pro
             290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
             325                 330                 335

Gly Asn Gly Val Ser Cys Gln Glu Thr Ala Val Thr Gln Thr Tyr Gly
             340                 345                 350

Gly Asn Ser Asn Gly Glu Pro Cys Val Leu Pro Phe Thr Tyr Asn Gly
             355                 360                 365

Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
             405                 410                 415

Gly Ala Leu Cys His Phe Pro Phe Leu Tyr Asn Asn His Asn Tyr Thr
             420                 425                 430

Asp Cys Thr Ser Glu Gly Arg Arg Asp Asn Met Lys Trp Cys Gly Thr
             435                 440                 445

Thr Gln Asn Tyr Asp Ala Asp Gln Lys Phe Gly Phe Cys Pro Met Ala
             450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
```

485                 490                 495
Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
        530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
        610                 615                 620

Ser His Pro Ile Gln Trp Asn Ala Pro Gln Pro Ser His Ile Ser Lys
625                 630                 635                 640

Tyr Ile Leu Arg Trp Arg Pro Val Ser Ile Pro Arg Asn Leu Gly
                645                 650                 655

Tyr

<210> SEQ ID NO 5
<211> LENGTH: 1374
<212> TYPE: DNA
<213> ORGANISM: Artificial Sequence
<220> FEATURE:
<223> OTHER INFORMATION: DNA sequence of 1G5.3 Heavy Chain

<400> SEQUENCE: 5

```
atgtacttgg gactgaactg tgtattcata gtttttctct taaaaggtgt ccagagtgaa      60
gtgaaaattg aggagtctgg aggaggcttg gtgcaacctg gaggatccat gaaactctcc     120
tgtgttgcct ctggattcac tttcagtaac gactggatga actgggtccg ccagtctcca     180
gagaagggc ttgagtgggt tgctgaaatt agaatgaaat ctgataatta tgcaacatat     240
tatgcggagt ctgtgaaagg gaggttcacc atctcaagag atgattccaa aatagtgtc     300
tacctgcaaa tgaacaattt aagagctgaa gacaatggca tttattactg taccagttgg     360
gactactggg gccaaggcac cactctcaca gtctcctcag ccaaaacgac ccccatctct     420
gtctatccac tggcccctgg atctgctgcc caaactaact ccatggtgac cctgggatgc     480
ctggtcaagg gctatttccc tgagccagtg acagtgacct ggaactctgg atccctgtcc     540
agcggtgtgc acaccttccc agctgtcctg cagtctgacc tctacactct gagcagctca     600
gtgactgtcc cctccagcac ctggcccagc gagaccgtca cctgcaacgt tgcccacccg     660
gccagcagca ccaaggtgga caagaaaatt gtgcccaggg attgtggttg taagccttgc     720
atatgtacag tcccagaagt atcatctgtc ttcatcttcc ccccaaagcc caaggatgtg     780
ctcaccatta ctctgactcc taaggtcacg tgtgttgtgg tagacatcag caaggatgat     840
cccgaggtcc agttcagctg gtttgtagat gatgtggagg tgcacacagc tcagacgcaa     900
ccccgggagg agcagttcaa cagcactttc cgctcagtca gtgaacttcc catcatgcac     960
caggactggc tcaatggcaa ggagttcaaa tgcagggtca acagtgcagc tttccctgcc    1020
cccatcgaga aaaccatctc caaaaccaaa ggcagaccga aggctccaca ggtgtacacc    1080
```

-continued

```
attccacctc ccaaggagca gatggccaag gataaagtca gtctgacctg catgataaca    1140
gacttcttcc ctgaagacat tactgtggag tggcagtgga atgggcagcc agcggagaac    1200
tacaagaaca ctcagcccat catggacaca gatggctctt acttcgtcta cagcaagctc    1260
aatgtgcaga gagcaactg ggaggcagga atactttca cctgctctgt gttacatgag     1320
ggcctgcaca accaccatac tgagaagagc ctctcccact ctcctggtaa atga          1374
```

<210> SEQ ID NO 6
<211> LENGTH: 457
<212> TYPE: PRT
<213> ORGANISM: Artificial Sequence
<220> FEATURE:
<223> OTHER INFORMATION: protein sequence of 1G5.3 Heavy Chain

<400> SEQUENCE: 6

```
Met Tyr Leu Gly Leu Asn Cys Val Phe Ile Val Phe Leu Leu Lys Gly
1               5                   10                  15

Val Gln Ser Glu Val Lys Ile Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Asp Trp Met Asn Trp Val Arg Gln Ser Pro Glu Lys Gly Leu
    50                  55                  60

Glu Trp Val Ala Glu Ile Arg Met Lys Ser Asp Asn Tyr Ala Thr Tyr
65                  70                  75                  80

Tyr Ala Glu Ser Val Lys Gly Arg Phe Thr Ile Ser Arg Asp Asp Ser
                85                  90                  95

Lys Asn Ser Val Tyr Leu Gln Met Asn Asn Leu Arg Ala Glu Asp Asn
            100                 105                 110

Gly Ile Tyr Tyr Cys Thr Ser Trp Asp Tyr Trp Gly Gln Gly Thr Thr
        115                 120                 125

Leu Thr Val Ser Ser Ala Lys Thr Thr Pro Pro Ser Val Tyr Pro Leu
    130                 135                 140

Ala Pro Gly Ser Ala Ala Gln Thr Asn Ser Met Val Thr Leu Gly Cys
145                 150                 155                 160

Leu Val Lys Gly Tyr Phe Pro Glu Pro Val Thr Val Thr Trp Asn Ser
                165                 170                 175

Gly Ser Leu Ser Ser Gly Val His Thr Phe Pro Ala Val Leu Gln Ser
            180                 185                 190

Asp Leu Tyr Thr Leu Ser Ser Ser Val Thr Val Pro Ser Ser Thr Trp
        195                 200                 205

Pro Ser Glu Thr Val Thr Cys Asn Val Ala His Pro Ala Ser Ser Thr
    210                 215                 220

Lys Val Asp Lys Lys Ile Val Pro Arg Asp Cys Gly Cys Lys Pro Cys
225                 230                 235                 240

Ile Cys Thr Val Pro Glu Val Ser Ser Val Phe Ile Phe Pro Pro Lys
                245                 250                 255

Pro Lys Asp Val Leu Thr Ile Thr Leu Thr Pro Lys Val Thr Cys Val
            260                 265                 270

Val Val Asp Ile Ser Lys Asp Asp Pro Glu Val Gln Phe Ser Trp Phe
        275                 280                 285

Val Asp Asp Val Glu Val His Thr Ala Gln Thr Gln Pro Arg Glu Glu
    290                 295                 300

Gln Phe Asn Ser Thr Phe Arg Ser Val Ser Glu Leu Pro Ile Met His
```

```
                305                 310                 315                 320
Gln Asp Trp Leu Asn Gly Lys Glu Phe Lys Cys Arg Val Asn Ser Ala
                325                 330                 335
Ala Phe Pro Ala Pro Ile Glu Lys Thr Ile Ser Lys Thr Lys Gly Arg
                340                 345                 350
Pro Lys Ala Pro Gln Val Tyr Thr Ile Pro Pro Lys Glu Gln Met
                355                 360                 365
Ala Lys Asp Lys Val Ser Leu Thr Cys Met Ile Thr Asp Phe Phe Pro
370                 375                 380
Glu Asp Ile Thr Val Glu Trp Gln Trp Asn Gly Gln Pro Ala Glu Asn
385                 390                 395                 400
Tyr Lys Asn Thr Gln Pro Ile Met Asp Thr Asp Gly Ser Tyr Phe Val
                405                 410                 415
Tyr Ser Lys Leu Asn Val Gln Lys Ser Asn Trp Glu Ala Gly Asn Thr
                420                 425                 430
Phe Thr Cys Ser Val Leu His Glu Gly Leu His Asn His His Thr Glu
                435                 440                 445
Lys Ser Leu Ser His Ser Pro Gly Lys
450                 455
```

<210> SEQ ID NO 7
<211> LENGTH: 720
<212> TYPE: DNA
<213> ORGANISM: Artificial Sequence
<220> FEATURE:
<223> OTHER INFORMATION: DNA sequence of 1G5.3 Light Chain

<400> SEQUENCE: 7

```
atggattcac aggcccaggt tcttatattg ctgctgctat gggtatctgg tacctgtggg    60
gacattgtga tgtcacagtc tccatcctcc ctggctgtgt caacaggaga gaaggtcact   120
atgaactgca gatccagtca ctatctgctc aacagtagaa cccgaaagaa cttcttgtct   180
tggtaccaac agaaaccagg acagtctcct caactgctga tctactgggc atccactagg   240
tattctgggg tccctgatcg cttcacaggc agtggatctg ggacagattt cactctcacc   300
atcagcagtg tgcaggctga agacctggca gtttattact gcaaacaatc ttataatctt   360
cacacgttcg gagggggac caagttggaa ataaagcggg ctgatgctgc accaactgta   420
tccatcttcc caccatccag tgagcagtta acatctggag tgcctcagt cgtgtgcttc   480
ttgaacaact ctacccccaa agacatcaat gtcaagtgga gattgatgg cagtgaacga   540
caaaatggcg tcctgaacag ttggactgat caggacagca agacagcac ctacagcatg   600
agcagcaccc tcacgttgac caaggacgag tatgaacgac ataacagcta cctgtgag    660
gccactcaca agacatcaac ttcacccatt gtcaagagct caacaggaa tgagtgttag   720
```

<210> SEQ ID NO 8
<211> LENGTH: 239
<212> TYPE: PRT
<213> ORGANISM: Artificial Sequence
<220> FEATURE:
<223> OTHER INFORMATION: protein sequence of 1G5.3 Light Chain

<400> SEQUENCE: 8

```
Met Asp Ser Gln Ala Gln Val Leu Ile Leu Leu Leu Leu Trp Val Ser
1               5                   10                  15
Gly Thr Cys Gly Asp Ile Val Met Ser Gln Ser Pro Ser Ser Leu Ala
                20                  25                  30
```

Val Ser Thr Gly Glu Lys Val Thr Met Asn Cys Arg Ser His Tyr
            35                  40                  45

Leu Leu Asn Ser Arg Thr Arg Lys Asn Phe Leu Ser Trp Tyr Gln Gln
 50                  55                  60

Lys Pro Gly Gln Ser Pro Gln Leu Leu Ile Tyr Trp Ala Ser Thr Arg
 65                  70                  75                  80

Tyr Ser Gly Val Pro Asp Arg Phe Thr Gly Ser Gly Ser Gly Thr Asp
                 85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu His Thr Phe Gly Gly Gly Thr Lys
        115                 120                 125

Leu Glu Ile Lys Arg Ala Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 9
<211> LENGTH: 11
<212> TYPE: PRT
<213> ORGANISM: Artificial Sequence
<220> FEATURE:
<223> OTHER INFORMATION: synthetic peptide

<400> SEQUENCE: 9

Val Ser Ile Pro Pro Arg Asn Leu Gly Tyr Cys
1               5                   10

<210> SEQ ID NO 10
<211> LENGTH: 123
<212> TYPE: PRT
<213> ORGANISM: Artificial Sequence
<220> FEATURE:
<223> OTHER INFORMATION: His-MSF

<400> SEQUENCE: 10

Met Gly Ser Asp Lys Ile His His His His His His His His His His
1               5                   10                  15

Gly Val Trp Lys Cys Asp Pro Val Asp Gln Cys Gln Asp Ser Glu Thr
            20                  25                  30

Gly Thr Phe Tyr Gln Ile Gly Asp Ser Trp Glu Lys Tyr Val His Gly
        35                  40                  45

Val Arg Tyr Gln Cys Tyr Cys Tyr Gly Arg Gly Ile Gly Glu Trp His
    50                  55                  60

Cys Gln Pro Leu Gln Thr Tyr Pro Ser Ser Gly Pro Val Glu Val
65                  70                  75                  80

Phe Ile Thr Glu Thr Pro Ser Gln Pro Asn Ser His Pro Ile Gln Trp
                85                  90                  95

Asn Ala Pro Gln Pro Ser His Ile Ser Lys Tyr Ile Leu Arg Trp Arg
            100                 105                 110

Pro Val Ser Ile Pro Pro Arg Asn Leu Gly Tyr
        115                 120

<210> SEQ ID NO 11
<211> LENGTH: 10
<212> TYPE: PRT
<213> ORGANISM: Artificial Sequence
<220> FEATURE:
<223> OTHER INFORMATION: synthetic peptide

<400> SEQUENCE: 11

Val Ser Ile Pro Pro Arg Asn Leu Gly Tyr
1               5                   10

<210> SEQ ID NO 12
<211> LENGTH: 3
<212> TYPE: PRT
<213> ORGANISM: Artificial Sequence
<220> FEATURE:
<223> OTHER INFORMATION: CDRH3

<400> SEQUENCE: 12

Trp Asp Tyr
1

<210> SEQ ID NO 13
<211> LENGTH: 19
<212> TYPE: PRT
<213> ORGANISM: Artificial Sequence
<220> FEATURE:
<223> OTHER INFORMATION: CDRH2

<400> SEQUENCE: 13

Glu Ile Arg Met Lys Ser Asp Asn Tyr Ala Thr Tyr Tyr Ala Glu Ser
1               5                   10                  15

Val Lys Gly

<210> SEQ ID NO 14
<211> LENGTH: 5
<212> TYPE: PRT
<213> ORGANISM: Artificial Sequence
<220> FEATURE:
<223> OTHER INFORMATION: CDRH1

<400> SEQUENCE: 14

Asn Asp Trp Met Asn
1               5

<210> SEQ ID NO 15
<211> LENGTH: 7
<212> TYPE: PRT
<213> ORGANISM: Artificial Sequence
<220> FEATURE:
<223> OTHER INFORMATION: CDRL3

<400> SEQUENCE: 15

Gln Ser Tyr Asn Leu His Thr
1               5

<210> SEQ ID NO 16
<211> LENGTH: 7
<212> TYPE: PRT
<213> ORGANISM: Artificial Sequence -continued

```
<220> FEATURE:
<223> OTHER INFORMATION: CDRL2

<400> SEQUENCE: 16

Trp Ala Ser Thr Arg Tyr Ser
1               5

<210> SEQ ID NO 17
<211> LENGTH: 17
<212> TYPE: PRT
<213> ORGANISM: Artificial Sequence
<220> FEATURE:
<223> OTHER INFORMATION: CDRL1

<400> SEQUENCE: 17

Arg Ser Ser His Tyr Leu Leu Asn Ser Arg Thr Arg Lys Asn Phe Leu
1               5                  10                  15

Ser

<210> SEQ ID NO 18
<211> LENGTH: 114
<212> TYPE: PRT
<213> ORGANISM: Artificial Sequence
<220> FEATURE:
<223> OTHER INFORMATION: variable region of the heavy chain

<400> SEQUENCE: 18

Glu Val Lys Ile Glu Glu Ser Gly Gly Gly Leu Val Gln Pro Gly Gly
1               5                  10                  15

Ser Met Lys Leu Ser Cys Val Ala Ser Gly Phe Thr Phe Ser Asn Asp
                20                  25                  30

Trp Met Asn Trp Val Arg Gln Ser Pro Glu Lys Gly Leu Glu Trp Val
            35                  40                  45

Ala Glu Ile Arg Met Lys Ser Asp Asn Tyr Ala Thr Tyr Tyr Ala Glu
        50                  55                  60

Ser Val Lys Gly Arg Phe Thr Ile Ser Arg Asp Asp Ser Lys Asn Ser
65                  70                  75                  80

Val Tyr Leu Gln Met Asn Asn Leu Arg Ala Glu Asp Asn Gly Ile Tyr
                85                  90                  95

Tyr Cys Thr Ser Trp Asp Tyr Trp Gly Gln Gly Thr Thr Leu Thr Val
            100                 105                 110

Ser Ser

<210> SEQ ID NO 19
<211> LENGTH: 112
<212> TYPE: PRT
<213> ORGANISM: Artificial Sequence
<220> FEATURE:
<223> OTHER INFORMATION: variable region of the light chain

<400> SEQUENCE: 19

Asp Ile Val Met Ser Gln Ser Pro Ser Ser Leu Ala Val Ser Thr Gly
1               5                  10                  15

Glu Lys Val Thr Met Asn Cys Arg Ser Ser His Tyr Leu Leu Asn Ser
                20                  25                  30

Arg Thr Arg Lys Asn Phe Leu Ser Trp Tyr Gln Gln Lys Pro Gly Gln
            35                  40                  45

Ser Pro Gln Leu Leu Ile Tyr Trp Ala Ser Thr Arg Tyr Ser Gly Val
        50                  55                  60

Pro Asp Arg Phe Thr Gly Ser Gly Ser Gly Thr Asp Phe Thr Leu Thr
```

```
                65                  70                  75                  80
Ile Ser Ser Val Gln Ala Glu Asp Leu Ala Val Tyr Tyr Cys Lys Gln
                    85                  90                  95

Ser Tyr Asn Leu His Thr Phe Gly Gly Gly Thr Lys Leu Glu Ile Lys
                100                 105                 110

<210> SEQ ID NO 20
<211> LENGTH: 342
<212> TYPE: DNA
<213> ORGANISM: Artificial Sequence
<220> FEATURE:
<223> OTHER INFORMATION: nucleic acid molecule encoding the antibody

<400> SEQUENCE: 20
gaagtgaaaa ttgaggagtc tggaggaggc ttggtgcaac ctggaggatc catgaaactc        60
tcctgtgttg cctctggatt cactttcagt aacgactgga tgaactgggt ccgccagtct       120
ccagagaagg ggcttgagtg ggttgctgaa attagaatga aatctgataa ttatgcaaca       180
tattatgcgg agtctgtgaa agggaggttc accatctcaa gagatgattc caaaaatagt       240
gtctacctgc aaatgaacaa tttaagagct gaagacaatg gcatttatta ctgtaccagt       300
tgggactact ggggccaagg caccactctc acagtctcct ca                          342

<210> SEQ ID NO 21
<211> LENGTH: 336
<212> TYPE: DNA
<213> ORGANISM: Artificial Sequence
<220> FEATURE:
<223> OTHER INFORMATION: nucleic acid molecule encoding the antibody

<400> SEQUENCE: 21
gacattgtga tgtcacagtc tccatcctcc ctggctgtgt caacaggaga gaaggtcact        60
atgaactgca gatccagtca ctatctgctc aacagtagaa cccgaaagaa cttcttgtct       120
tggtaccaac agaaaccagg acagtctcct caactgctga tctactgggc atccactagg       180
tattctgggg tccctgatcg cttcacaggc agtggatctg ggacagattt cactctcacc       240
atcagcagtg tgcaggctga agacctggca gtttattact gcaaacaatc ttataatctt       300
cacacgttcg gagggggggac caagttggaa ataaag                                 336
```

The invention claimed is:

1. An antibody that comprises:

a complementarity determining region 3 of the heavy chain (CDRH3) having the amino acid sequence WDY SEQ ID No: 12; and a complementarity determining region 2 of the heavy chain (CDRH2) having the amino acid sequence EIRMKSDNYATYYAESVKG (SEQ ID NO:13); and a complementarity determining region 1 of the heavy chain (CDRH1) having the amino acid sequence NDWMN (SEQ ID NO:14); and a complementarity determining region 3 of the light chain (CDRL3) having the amino acid sequence KQSYNLHT (SEQ ID NO:15); and a complementarity determining region 2 of the light chain (CDRL2) having the amino acid sequence WASTRYS (SEQ ID NO:16); and a complementarity determining region 1 of the light chain (CDRL1) having the amino acid sequence RSSHYLLNSRTRKNFLS (SEQ ID NO:17).

2. The antibody according to claim 1 wherein the antibody is able to recognize and bind to an epitope comprising the sequence VSIPPRNLGY (SEQ ID NO:11) of human Migration Stimulating Factor (MSF).

3. The antibody according to claim 1 wherein said antibody is obtained making use of the peptide of sequence VSIPPRNLGY (SEQ ID NO:11) and/or wherein said antibody is selected from the group consisting of IgG, IgM, IgA and IgE antibodies.

4. The antibody according to claim 1 wherein said antibody is able to recognize and bind MSF in an immunoassay.

5. The antibody according to claim 4 wherein the immunoassay is an enzyme-linked immunosorbent assay (ELISA).

6. The antibody according to claim 1 comprising:
the variable region of the heavy chain comprising the amino acid sequence:

(SEQ ID NO: 18)
EVKIEESGGGLVQPGGSMKLSCVASGFTFSNDWMNWVRQSPEKGLEWV

AEIRMKSDNYATYYAESVKGRFTISRDDSKNSVYLQMNNLRAEDNGIY

YCTSWDYWGQGTTLTVSS and/or
the variable region of the light chain comprising the amino acid sequence:

(SEQ ID NO: 19)
DIVMSQSPSSLAVSTGEKVTMNCRSSHYLLNSRTRKNFLSWYQQKPG

QSPQLLIYWASTRYSGVPDRFTGSGSGTDFTLTISSVQAEDLAVYYC

KQSYNLHTFGGGTKLEIK.

7. The antibody according to claim 1, wherein the antibody does not recognize and bind human Fibronectin 1 (hFn1).

8. The antibody according to claim 1, wherein said antibody is selected from the group consisting of monoclonal antibodies, chimeric antibodies, humanized antibodies, deimmunized, fully human antibody, single chain antibodies, bispecific antibodies, diabodies, scFv, Fab, F(ab)'2, and di-, oligo- or multimers thereof.

9. A pharmaceutical composition comprising the antibody as defined in claim 1 and pharmaceutical acceptable excipients.

10. The antibody according to claim 6, wherein the heavy chain consists essentially of the amino acid sequence of SEQ ID No: 6 and/or the light chain consisting essentially of the amino acid sequence of SEQ ID NO: 8.

11. An in vitro or ex-vivo method for selectively detecting and/or measuring the amount of the protein MSF or of fragments thereof comprising the step of detecting MSF or of fragments thereof in an isolated biological sample obtained from the subject by means of a specific ligand which is able to recognize and bind to an epitope comprising the sequence VSIPPRNLGY (SEQ ID NO:11) of human Migration Stimulating Factor (MSF), and that does not recognize and bind human Fibronectin 1 (hFn1), said ligand being an antibody, as defined in claim 1.

12. The in vitro or ex vivo method according to claim 11 comprising the steps of:
    a) contact and incubation of the biological sample with the antibody thereby forming a MSF-antibody complex, if MSF is present;
    b) separation of the biological sample from the MSF-antibody complex;
    c) selective detection of MSF bound to the antibody and/or quantifying the amount of MSF bound to the antibody using detecting means for the antibody;
    d) comparison of the result obtained in c) with a control result.

13. The in vitro or ex vivo method according to claim 12 wherein the antibody is immobilized on a solid support.

14. The in vitro or ex vivo method according to claim 12, wherein the detecting means comprises a detectable antibody; and
the detectable antibody is biotinylated, and the detection means is avidin or streptavidin-peroxidase and 3,3',5,5'-tetramethyl benzidine;
the detectable antibody is conjugated to peroxidase, and the detection means is 3,3',5,5'-tetramethyl benzidine;
the detectable antibody is conjugated to alkaline phosphatase, and the detection means is p-nitrophenyl phosphate and/or 4-methylumbelliferyl phosphate.

15. The in vitro or ex vivo method according to claim 11, wherein said detection and/or measurement of the amount of the protein MSF or of fragments thereof is carried out by an immunoassay.

16. A method for detecting and/or quantifying the protein MSF or fragments thereof in an isolated biological sample, comprising contacting the isolated biological sample with an antibody of claim 1.

* * * * *

UNITED STATES PATENT AND TRADEMARK OFFICE
CERTIFICATE OF CORRECTION

PATENT NO. : 11,254,739 B2
APPLICATION NO. : 16/648333
DATED : February 22, 2022
INVENTOR(S) : Alberto Mantovani et al.

It is certified that error appears in the above-identified patent and that said Letters Patent is hereby corrected as shown below:

In the Specification

In Column 4, Line 3, the paragraph should read:
-- a complementarity determining region 3 of the light chain (CDRL3) having at least 80% of identity to the amino acid sequence KQSYNLHT (SEQ ID NO: 15) (aa. 116-122 of SEQ. ID No. 8). --

In Column 4, Line 34, the paragraph should read:
-- a complementarity determining region 3 of the light chain (CDRL3) having at least 80% of identity to the amino acid sequence KQSYNLHT (SEQ ID NO: 15) (aa. 116-122 of SEQ. ID No. 8), preferably said CDRL3 comprising the sequence of SEQ. ID No. 15, and/or --

In Column 4, Line 47, the paragraph should read:
-- Said complement determining region (CDR) peptide is preferably a CDR3 peptide comprising an amino acid sequence selected from the group consisting of: WDY (SEQ ID NO: 12) (aa. 120-122 of SEQ. ID No. 6) and KQSYNLHT (SEQ ID NO: 15) (aa. 116-122 of SEQ. ID No. 8). --

In Column 4, Line 59, the paragraph should read:
-- a complementarity determining region 3 of the light chain (CDRL3) having at least 80% of identity to the amino acid sequence QSYNLHT (SEQ ID NO: 15) (aa. 116-122 of SEQ ID No. 8), preferably said CDRL3 comprising the sequence of SEQ ID No. 15. --

In Column 5, Line 4, the paragraph should read:
-- a complementarity determining region 3 of the light chain (CDRL3) having at least 80% of identity to the amino acid sequence KQSYNLHT (SEQ ID NO: 15) (aa. 116-122 of SEQ ID No. 8), preferably said CDRL3 comprising the sequence of SEQ ID No. 15. --

Signed and Sealed this
Twenty-first Day of February, 2023

Katherine Kelly Vidal
*Director of the United States Patent and Trademark Office*

CERTIFICATE OF CORRECTION (continued)
U.S. Pat. No. 11,254,739 B2

In Column 77, Line 57, the sequence listing should read:

--
<210> SEQ ID NO 15

<211> LENGTH: 7

<212> TYPE: PRT

<213> ORGANISM: Artificial Sequence

<220> FEATURE:

<223> OTHER INFORMATION: CDRL3

<400> SEQUENCE: 15

Lys Gln Ser Tyr Asn Leu His Thr
1               5   --